(12) United States Patent
McMillan et al.

(10) Patent No.: US 8,685,010 B2
(45) Date of Patent: Apr. 1, 2014

(54) PHOTOTHERMAL TREATMENT OF SOFT TISSUES

(75) Inventors: Kathleen McMillan, Concord, MA (US); Anurag Gupta, Tucson, AZ (US); James Patrick McGuire, Jr., Pasadena, CA (US)

(73) Assignee: Gradiant Research, LLC, Concord, MA (US)

( * ) Notice: Subject to any disclaimer, the term of this patent is extended or adjusted under 35 U.S.C. 154(b) by 735 days.

(21) Appl. No.: 12/625,335

(22) Filed: Nov. 24, 2009

(65) Prior Publication Data

US 2010/0160904 A1    Jun. 24, 2010

Related U.S. Application Data

(60) Provisional application No. 61/117,279, filed on Nov. 24, 2008.

(51) Int. Cl.
*A61B 18/18* (2006.01)

(52) U.S. Cl.
USPC ............. 606/15; 606/13; 606/14; 606/16; 606/17; 606/18; 606/19; 607/91; 607/92; 607/93

(58) Field of Classification Search
CPC ............. A61B 18/22; A61N 5/0625; A61N 2005/0606; A61N 2005/0644; A61N 2005/0666
USPC ............. 606/14, 15, 13, 16–19; 607/91–93
See application file for complete search history.

(56) References Cited

U.S. PATENT DOCUMENTS 4,638,436 A    1/1987    Badger et al.
(Continued)

FOREIGN PATENT DOCUMENTS

JP    2001-046396    2/2001
(Continued)

OTHER PUBLICATIONS

Supplementary European Search Report for European Application No. 09 82 8386 dated Apr. 11, 2012.
(Continued)

*Primary Examiner* — Tod T Van Roy

(57) ABSTRACT

An apparatus and a method are provided for the treatment of soft tissue. The apparatus includes a light source and at least two optical assemblies. Each of the optical assemblies includes at least one optical element and a light-transmitting contact surface configured to transmit a substantially uniform distribution of light therethrough. The apparatus further includes at least two optical transmission devices each disposed between the light source and a corresponding one of the at least two optical assemblies. The apparatus also includes a handpiece to which the at least two optical assemblies are attached, and which is adapted to bring the light-transmitting contact surfaces of the at least two optical assemblies in contact with soft tissue disposed therebetween. The method includes compressing and substantially flattening portions of the tonsil tissue between light-transmitting contact surfaces of two opposed light emitting optical assemblies, introducing light into an optical element of each of the optical assemblies; and irradiating the tonsil tissue by directing the light from the optical element through the light-transmitting contact surfaces to the tonsil tissue in a substantially uniform light distribution.

62 Claims, 42 Drawing Sheets

(56) References Cited

U.S. PATENT DOCUMENTS

| | | | |
|---|---|---|---|
| 5,328,488 A * | 7/1994 | Daikuzono | 606/16 |
| 5,445,146 A | 8/1995 | Bellinger | |
| 5,861,020 A | 1/1999 | Schwarzmaier | |
| 5,951,596 A | 9/1999 | Bellinger | |
| 6,240,925 B1 | 6/2001 | McMillan et al. | |
| 6,267,779 B1 | 7/2001 | Gerdes | |
| 6,290,713 B1 | 9/2001 | Russell | |
| 6,339,458 B1 | 1/2002 | Ohkawa | |
| 6,389,313 B1 | 5/2002 | Marchitto et al. | |
| 6,451,013 B1 * | 9/2002 | Bays et al. | 606/27 |
| 6,659,999 B1 | 12/2003 | Anderson et al. | |
| 6,682,501 B1 | 1/2004 | Nelson et al. | |
| 6,746,473 B2 | 6/2004 | Shanks et al. | |
| 2001/0025176 A1 | 9/2001 | Ellsberry et al. | |
| 2002/0058931 A1* | 5/2002 | Parker et al. | 606/16 |
| 2004/0093042 A1 | 5/2004 | Altshuler et al. | |
| 2006/0047329 A1 | 3/2006 | Krespi et al. | |
| 2006/0058712 A1 | 3/2006 | Altshuler et al. | |
| 2007/0027440 A1 | 2/2007 | Altshuler et al. | |
| 2007/0185188 A1 | 8/2007 | Mirejovsky et al. | |
| 2008/0021370 A1 | 1/2008 | Borenstein | |
| 2010/0160904 A1 | 6/2010 | McMillan et al. | |
| 2011/0190749 A1* | 8/2011 | McMillan et al. | 606/16 |
| 2012/0078160 A1 | 3/2012 | McMillan | |
| 2013/0197473 A1 | 8/2013 | McMillan | |

FOREIGN PATENT DOCUMENTS

| | | |
|---|---|---|
| JP | 2001-204831 | 7/2001 |
| JP | 2006-051388 | 2/2006 |
| WO | WO 99/01696 | 1/1999 |
| WO | WO 02/087698 A1 | 11/2002 |
| WO | WO 2008/049905 | 5/2008 |
| WO | WO 2010/102099 A1 | 9/2010 |

OTHER PUBLICATIONS

Arens, R., et al., "Linear dimensions of the upper airway structure during development," *Am. J. Respir. Crit. Care Med.*, 165: 117-122 (2002).

Arrarte, J.L.F., et al., "The effect of adenotonsillectomy on oxygen saturation in children with sleep-disordered breathing," *J. Bras. Pneumol.*, 33: 62-68 (2007).

Bhattacharyya, N., "Evaluation of post-tonsillectomy bleeding in the adult population," *ENT-Ear, Nose & Throat Journal*, 80: 544-549 (2001).

Brodsky, L., et al., "Naso- and oropharyngeal dimensions in children with obstructive sleep apnea," *Int. J. Pediatr. Otorhinolaryngol.*, 17: 1-11 (1989).

Chang, K.W., "Intracapsular versus subcapsular coblation tonsillectomy," *Otolaryngol. Head Neck Surg.*, 138: 153-157 (2008).

Chole, R.A., et al., "Anatomical evidence of microbial biofilms in tonsillar tissues," *Arch. Otolaryngol. Head Neck Surg.*, 129: 634-636 (2003).

Colen, T.Y., et al., "Effect of intracapsular tonsillectomy on quality of life for children with obstructive sleep-disordered breathing," *Arch. Otolaryngol. Head Neck Surg.*, 134: 124-127 (2008).

Derkay, C.S., et al., "Post-tonsillectomy morbidity and quality of life in pediatric patients with obstructive tonsils and adenoid: microdebrider vs electrocautery," *Otolaryngol. Head Neck Surg.*, 134: 114-120 (2006).

Galland, B.C., et al., "Changes in behavior and attentional capacity after tonsillectomy," *Pediatr. Res.*, 59: 711-716 (2006).

Notification of Transmittal of the International Search Report and Written Opinion of the International Searching Authority, or the Declaration, for International Application No. PCT/US2009/065768, mailing date Jul. 20, 2010.

Isaacson, G., et al., "Developmental anatomy of the tonsil and its implications for intra-capsular tonsillectomy," *Int. J. Pediatr. Otorhinolaryngol.*, doi:0.1016/j.ijpor1.2007.09.021 (2007).

Magdy, E.A., et al., "Coblation tonsillectomy: a prospective, double-blind, randomized, clinical and Histopathological comparison with dissection-ligation, monopolar electrocautery and laser tonsillectomies," *J. Laryngol. Otol.*, 122: 282-290 (2008).

Michel, R.G., et al., "Safety and efficacy of pressure-assisted tissue-welding tonsillectomy: a preliminary evaluation," *ENT-Ear, Nose & Throat Journal*, 87: 100-112 (2008).

Okuyucu, S., et al., "The effect of anesthetic agents on perioperative bleeding during tonsillectomy: propofol-based versus desflurane-based anesthesia," *Otolaryngol. Head Neck Surg.*, 138: 158-161 (2008).

Ozdemir, I., et al., "Measurement of tonsillar blood flow in normal and pathological conditions by the use of the 133Xe clearance technique," *Arch. Otorhinolaryngol.*, 242: 53-56 (1985).

Roth, J.A., et al., "Harmonic scalpel tonsillectomy versus monopolar diathermy tonsillectomy: a prospective study," *ENT—Ear, Nose & Throat J.*, 87: 346-349 (2008).

Salonen, A., et al., "Recovery after tonsillectomy in adults: a three-week followup study," *Laryngoscope*, 112: 94-98 (2002).

Shah, R.K., et al., "Optical-thermal simulation of tonsillar tissue irradiation," *Lasers Surg. Med.*, 28: 313-319 (2001).

Stearns, M.P., "The relationship between adenoid weight to tonsillar weight," *J. Laryngol. Otol.*, 97: 519-521 (1983).

Windfuhr, J.P., et al., "Life threatening posttonsillectomy hemorrhage," *Laryngoscope*, 118 (2008).

Young, T., et al., "Epidemiology of Obstructive Sleep Apnea," *Am. J. Respir. Crit. Care Med.*, 165: 1217-1239 (2002).

Allison, K.P., et al., "Pulsed dye laser treatment of superficial basal cell carcinoma: realistic or not?," *Lasers Med. Sci.*, 18: 125-6 (2003).

Au, J. L-S., et al., "Clinical Aspects of Drug Delivery to Tumors," *J. Control Rel.*, 78: 81-95 (2002).

Beutner, K.R., et al., "Effect of Pulsed Dye Laser on Basal Cell Carcinoma," *Lasers Surg. Med. Suppl.*, 14: 22 (2002).

Botteman, M.F., et al., "The Health Economics of Bladder Cancer," *Pharmacoeconomics*, 21(18): 1315-1330 (2003).

Campolmi, P., et al., "Vascular based non conventional dye laser treatment for basal cell carcinoma," *Dermatol. Ther.*, 21: 402-405 (2008).

Chen, D., et al., "Effect of Dimethyl Sulfoxide on Bladder Tissue Penetration of Intravesical Paclitaxel," *Clin. Cancer Res.*, 9: 363-369 (2003).

Christenson, L.J., et al., "Incidence of Basal Cell and Squamous Cell Carcinomas in a Population Younger Than 40 Years," *JAMA*, 294: 681-690 (2005).

Foley, P., et al., "Photodynamic therapy with methyl aminolevulinate for primary nodular basal cell carcinoma: results of two randomized studies," *Int. J. Dermatol.*, 48: 1236-1245 (2009).

Hallock, G.G. and Lutz, D.A., "A Prospective Study of the Accuracy of the Surgeon's Diagnosis and Significance of Positive Margins in Nonmelanoma Skin Cancers," *Plast. Reconstr. Surg.*, 107: 942-947 (2001).

Jemal, A., et al., "Cancer Statistics, 2008," *CA Cancer J. Clin.*, 58: 71-96 (2008).

Karim, M.A., et al., "Realization of a uniform circular source using a two-dimensional binary filter," *Optics Letters*, vol. 10, No. 10 (Oct. 1985).

Kretsos, K. and Kasting, G.B., "Dermal Capillary Clearance: Physiology and Modeling," *Skin Pharmacol. Physiol.*, 18: 55-74 (2005).

Lee, S-J., et al., "Bioadhesive Drug Delivery System Using Glyceryl Monooleate for the Intravesical Administration of Paclitaxel," *Chemotherapy*, 51: 311-318 (2005).

Love, W.E., et al., "Topical Imiquimod or Fluorouracil Therapy for Basal and Squamous Cell Carcinoma," *Arch. Dermatol.*, 145: 1431-1438 (2009).

Lu, Z., et al., "Paclitaxel-Loaded Gelatin Nanoparticles for Intravesical Bladder Cancer Therapy," *Clin. Cancer Res.*, 10: 7677-7684 (2004).

Overholt, B., et al., "Photodynamic Therapy for Esophageal Cancer Using a 180° Windowed Esophageal Balloon," *Lasers in Surgery and Medicine* 14:27-33 (1994).

Robinson, J.K. and Fisher, S.C., "Recurrent Basal Cell Carcinoma After Incomplete Resection," *Arch. Dermatol.*, 136: 1318-1324 (2000).

(56) References Cited

OTHER PUBLICATIONS

Shah, S.M., et al., "The Effect of 595 nm Pulsed Dye Laser on Superficial and Nodular Basal Cell Carcinomas," *Lasers Surg. Med.*, 41: 417-422 (2009).

Sukai, S.A., et al., "What Lies Beneath? A Lesson for the Clinician. Intraoperative Frozen Section Appearance of Persistent Basal Cell Carcinoma after Apparent Cure with Imiquimod 5% Cream," *Derm. Surg.*, 35: 1831-1834 (2009).

Tierney, E.P. and Hanke, C.W., "Cost Effective of Mohs Micrographic Surgery: Review of the Literature," *J. Drugs Dermatol.*, 8: 914-922 (2009).

Zijistra, W.G., et al., "Absorption Spectra of Human Fetal and Adult Oxyhemoglobin, De-Oxyhemoglobin, Carboxyhemoglobin, and Methemoglobin," *Clinical Chemistry* vol. 37, No. 9, 1633-1638 (1991).

Notification Concerning Transmittal of International Preliminary Report on Patentability for International Application No. PCT/US2009/065768 dated Jun. 3, 2011.

Office Action from U.S. Appl. No. 12/952,946, filed Nov. 23, 2010, mailed Mar. 13, 2013.

Koechner, W. Solid-State Laser Engineering, $2^{nd}$ Ed., Springer-Verlag, pp. 251-253 (1988).

Office Action from U.S. Appl. No. 12/952,946, filed Nov. 23, 2010 mailed Nov. 7, 2012.

* cited by examiner

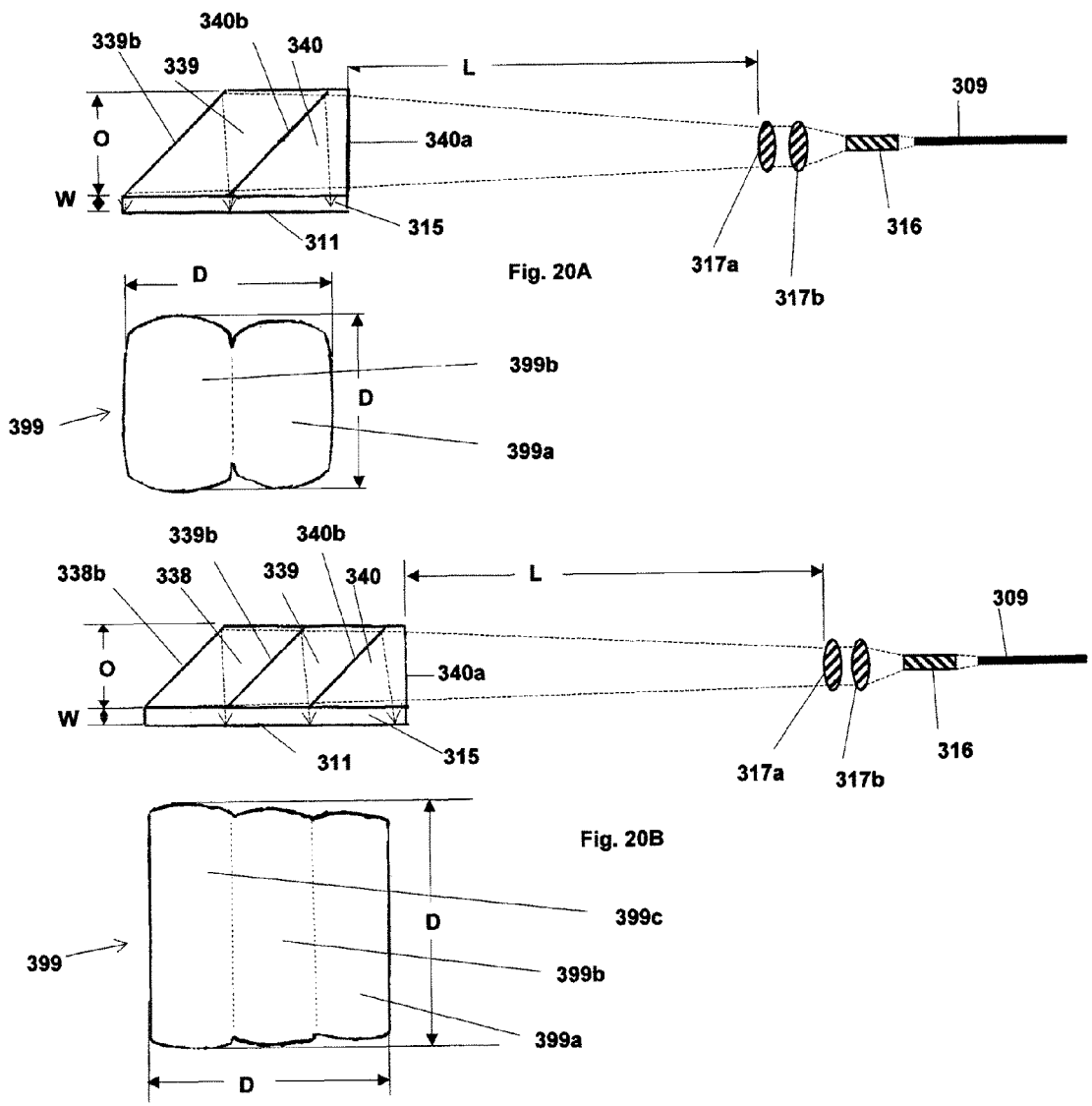

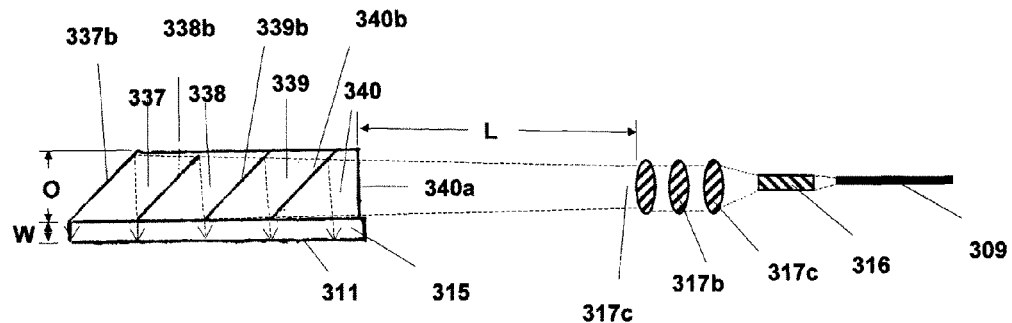
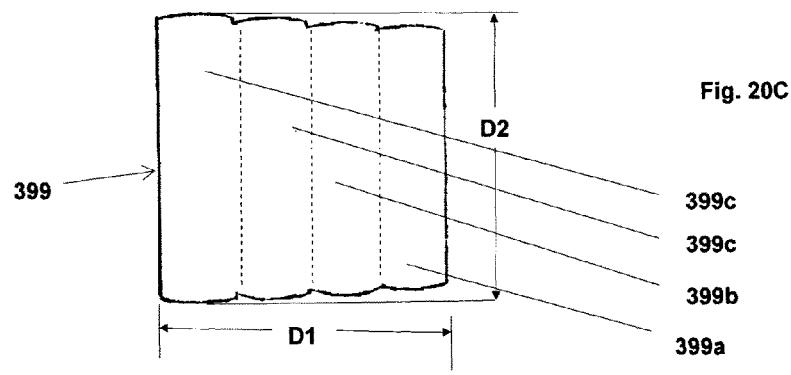
Fig. 20C
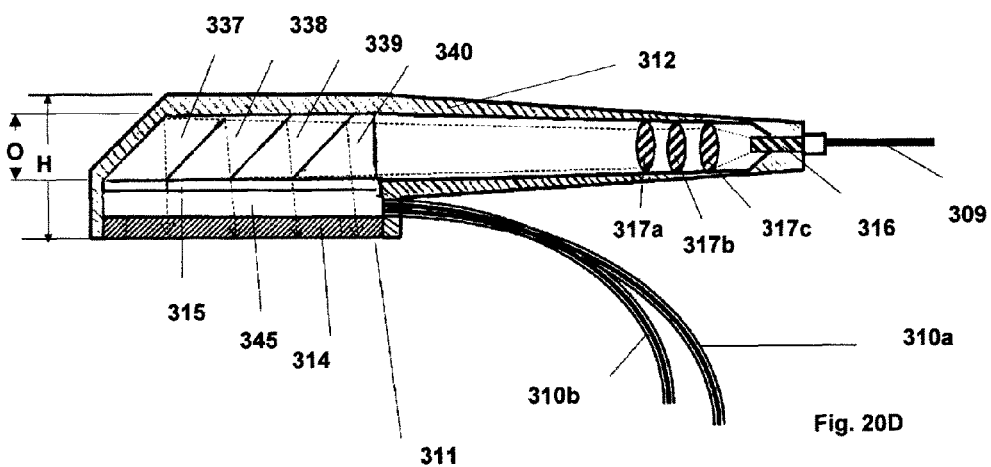
Fig. 20D

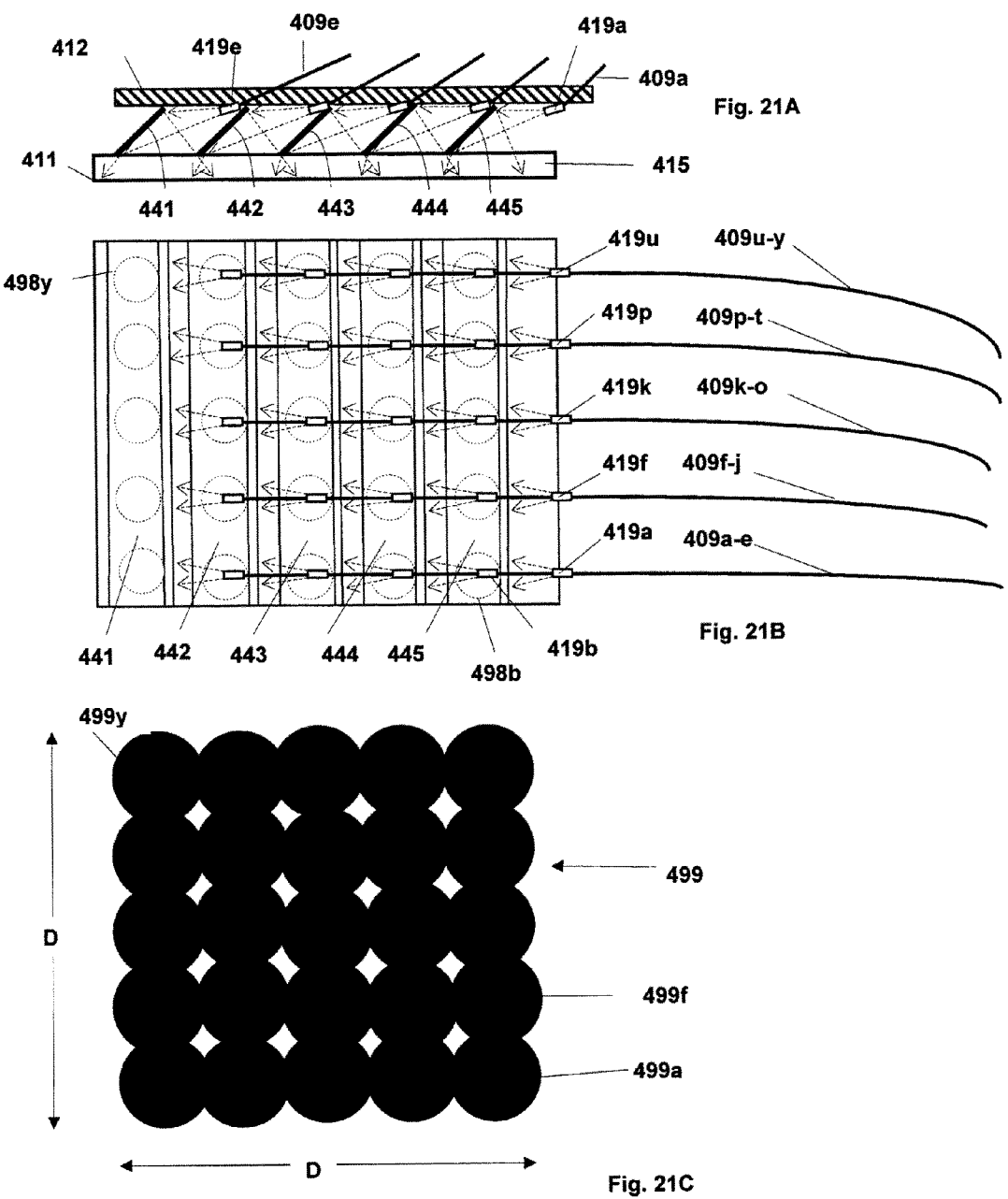

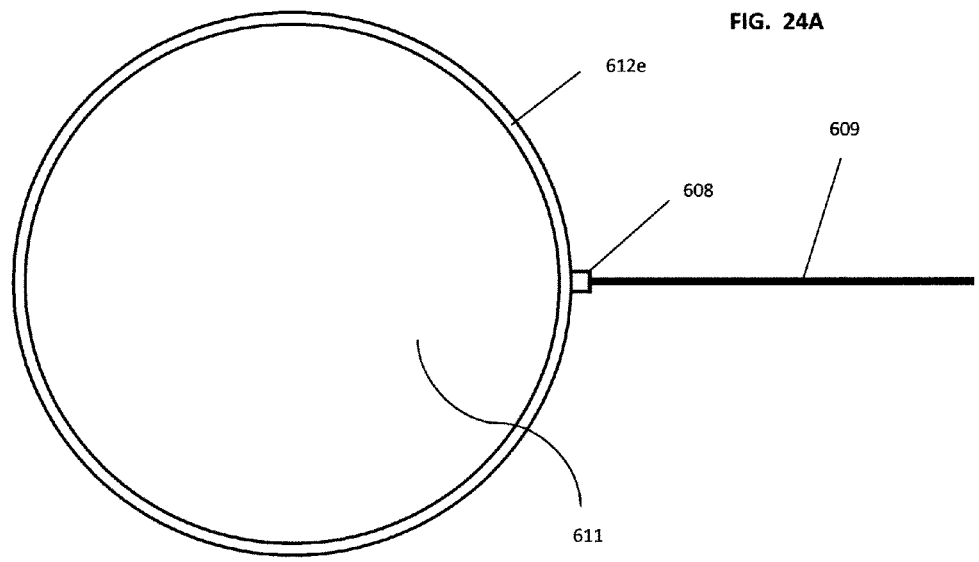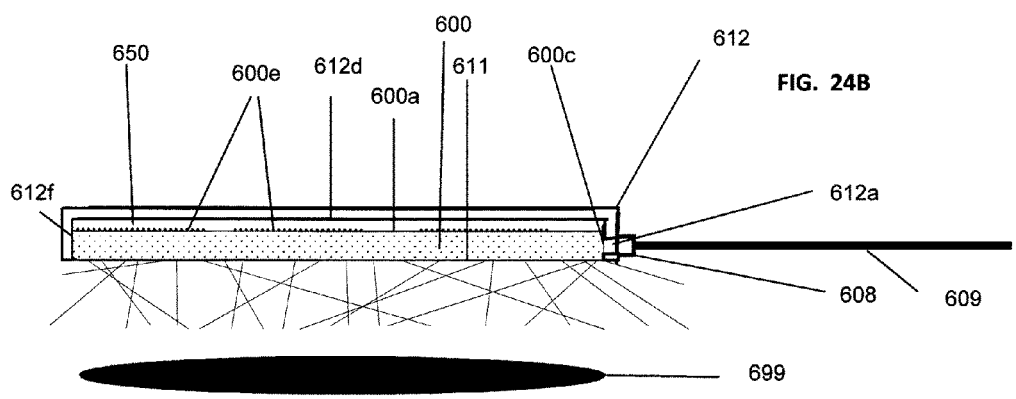

PHOTOTHERMAL TREATMENT OF SOFT TISSUES

RELATED APPLICATION(S)

This application claims the benefit of U.S. Provisional Application No. 61/117,279, filed on Nov. 24, 2008.

The entire teachings of the above application(s) are incorporated herein by reference.

BACKGROUND OF THE INVENTION

It has been stated that "the quest for the elimination of tonsillectomy-associated morbidity has vexed several generations of otolaryngologists" (Colen 2008). Indications for the excision of palatine tonsils (hereinafter referred to as "tonsils") in pediatric populations are recurrent or chronic tonsillitis, and hypertrophic tonsils with obstructive sleep-disordered breathing (OSDB). Severe OSDB with sleep apnea is associated with serious morbidity, and mild-to-moderate OSDB with significant neurobehavioral morbidity affecting memory, cognition, and school performance (Galland 2006). In recent years, tonsillar hypertrophy has surpassed tonsillitis as the primary indication for tonsillectomy in children. In adults the primary indication is tonsillitis. There are approximately 900,000 tonsillectomies yearly in the United States.

The tonsils are organs of the immune system that are located on the lateral walls of the oropharynx, where in health they may be seen as a pair of roughly ellipsoid structures. The tonsillar capsule, a thin, dense layer of connective tissue covering the lateral surface of the tonsil, is an important anatomical reference point. Immediately under the capsule is a loose connective tissue layer, and under that layer are muscles of the pharynx used in swallowing. These muscles adjacent to the capsule form the tonsillar bed. The capsule does not extend to the exposed medial surfaces of the tonsils, instead, like the rest of the oropharynx, the exposed surface of the tonsil is a mucosal layer consisting of epithelium with an underlying lamina propria. However, the surface of the tonsil is distinguished by many diverticula ("crypts"), which vary in size but which extend in depth to the capsule. The capsule in turn extends into the tonsil parenchyma to form fibrovascular septa that divide the tonsil into multiple lymphatic tissue lobes.

At birth there is only an incipient tonsil, but soon thereafter there is rapid proliferation of lymphoid cells and commensurate expansion of the size of the tonsils. The immune activity of the tonsils is greatest in early childhood. By the second decade of life the lymphoid component of the tonsil begins to involute, and the fibrovascular tissue of the capsule and septa increases in proportion, such that the tonsil atrophies as a person ages, becoming smaller once again but also more fibrotic (Isaacson 2007).

An MRI study (Arens 2002) of children aged 1 to 11 years without tonsil disease showed that the average intertonsillar distance along a line across the airway passing through the center of both tonsils is approximately 7 mm, regardless of age. The combined width of both tonsils along this line increases from about 33 mm to 42 mm, with increasing age in this population. Thus, even with normal growth, the tonsils of young children are very large relative to the airway. Tonsillar hypertrophy involves an abnormal expansion of the lymphoid component of the tonsil such that the airway is compromised. Although adults commonly have tonsils removed as part of a uvulopalatopharyngoplasty (UPPP) procedure for obstructive sleep apnea, tonsillar hypertrophy (with or without adenoidal hypertrophy) as the cause of OSDB is a pediatric condition. The minimum prevalence of childhood obstructive sleep apnea has been estimated as approximately 2 to 3% (Young 2002). In the United States alone, based on most recent census data and considering only the population of 40 million children aged 9 years and younger, this prevalence corresponds to 800,000 to 1,200,000 children with OSDS. The American Academy of Pediatrics has recently recommended screening of all children over one year old for snoring.

Tonsillitis occurs in both adult and pediatric populations when the immune cells of the tonsils are overwhelmed by a pathogen. Antibiotics are frequently ineffective in preventing acute tonsillitis in patients with recurrent tonsillitis. The reason for this lack of efficacy may be the formation of biofilms by bacteria in the tonsillar crypts (Chole 2003). Inflammation leads to fibrosis or scar tissue production in the tonsils of patients with recurrent or chronic tonsillitis.

The pathophysiology of hypertrophic tonsils differs from tonsils with recurrent, chronic tonsillitis. Blood flow to hypertrophic tonsils is significantly greater than blood flow to normal control tonsil, whereas in chronic tonsillitis the blood flow is reduced (Ozdemir 1985). Data from a morphologic study of the oropharynx of children undergoing tonsillectomy indicate that hypertrophic tonsils are less dense than tonsils from tonsillitis patients (Brodsky 1989).

Tonsils in patients with either recurrent, chronic tonsillitis or tonsillar hypertrophy show a wide range in size. Tonsils removed from 31 children treated for OSDB ranged in volume from 5 ml to 18 ml with mean 10.18 ml (Arrarte 2007). This range is similar to the range of tonsil mass (3 to 18.2 g, mean 8.8 g) in 45 children with recurrent tonsillitis (Stearns 1983). In a recent study of patients with tonsillar hypertrophy, or recurrent or chronic tonsillitis, 50 patients aged 2 to 12 years had tonsil weight ranging from 4.0 to 17.6 g (mean 8.7 g), and in 50 patients aged 12 to 47 years, the range was 4.8 to 19.8 g (mean 9.4 g) (Michel 2008).

The tonsillectomy procedure is essentially the same regardless of indication, patient age, or size of tonsils. The tonsils are excised with a surgical plane in the loose connective tissue between the tonsillar capsule and the pharyngeal muscle of the tonsillar bed. In this way, the lymphoid tissue of the tonsil is removed completely, and damage to the muscle in minimized.

A number of different cutting tools can be used to excise the tonsils, for example "cold steel" instruments (knife, scissors, snare, or scalpel), with ligation or electrocautery to control bleeding, or "hot" instruments such as monopolar or bipolar electrocautery, and laser (CO2 or frequency doubled Nd:YAG). Differences between these methods depend on the amount of residual thermal damage produced in the tonsillar bed: cold techniques are associated with little or no residual damage and less postoperative pain, while electrocautery produces more residual damage but also provides the best intraoperative hemostasis. In recent years newer technologies have been developed and used for tonsillectomy; these include ultrasonic dissection (Harmonic Scalpel, Ethicon Endo-Surgery, Cincinnati, Ohio), plasma-assisted radiofrequency ablation (Coblation, ArthroCare Corporation, Sunnyvale, Calif.), argon plasma coagulation (Erbe Elektromedizin GmbH, Tubingen, Germany), and pressure assisted tissue-welding (ENTceps, Starion Instruments Corporation, Sunnyvale, Calif.). Regardless of technology used and the care taken to minimize injury, the end result of excision of the tonsils is an open wound at the tonsillar bed that heals by secondary intention over a period of several days. Pain during healing from tonsillectomy is attributable to nerve irritation, inflammation, and muscle spasm in the pharyngeal wall and is a substantial morbidity that can also lead to decreased oral intake, dehydration, and infection. A recent study in adults has shown a mean duration of significant post-tonsillectomy pain of 11 days, and that pain remained relatively unchanged for the first 5 days after surgery (Salonen 2002). Adults frequently require 2 weeks of recovery after tonsillectomy before returning to work (Magdy 2008). Many adults with chronic or recurrent tonsil disease forgo treatment because of an unwillingness or inability to undergo the prolonged and painful recovery. Children have moderate to severe pain for at least 2 days after tonsillectomy despite pain medication, and typically require several days to resume normal activities. Pain upon swallowing during recovery can lead to dehydration and readmission to hospital. Post-tonsillectomy childcare involves missed work for parents and additional economic costs of treatment. The increased importance of hypertrophic tonsils as an indication for tonsillectomy has led to more very young patients in recent years. The risks of dehydration and bleeding are more serious in small children, and have been an additional motivation for finding a procedure that minimizes postoperative pain and risk of bleeding (Derkay 2006).

In both children and adults, most serious complication of tonsillectomy is bleeding. The incidence of post-operative bleeding is approximately 5%, and is classified as primary when it occurs within 24 hours of surgery and secondary when later. Secondary bleeding is caused when sloughing of the surgical eschar exposes the stumps of tonsillar vessels, and most often occurs between 4 and 7 days after surgery (Windfuhr 2008). Secondary bleeding can be life-threatening and is particularly dangerous because it occurs when the patient is away from immediate medical care. Children are particularly at risk of the consequences of secondary bleeding due to their smaller hemodynamic reserve (Okuyucu 2008). The incidence of secondary post-operative bleeding has remained constant at 1 to 3% regardless of developments in tonsillectomy technique (Colen 2008, Windfuhr 2008). Approximately half of all patients with bleeding return to the operating room (Bhattacharyya 2001).

Adenoidectomy is frequently performed with tonsillectomy in children however adenoidectomy has a low risk of pain and bleeding. Morbidities following tonsillectomy with adenoidectomy are attributable to the tonsillectomy portion of the procedure.

As a consequence of the inherent morbidities of excisional tonsillectomy, there has been recent interest in the alternative of partial tonsillectomy (also known as intracapsular tonsillectomy, or tonsillotomy), in which the surgeon removes a large portion of the tonsils but leaves a barrier of tissue over the capsule. Over the past 15 years various techniques have been used to debulk the tonsils in a partial tonsillectomy, including CO2 laser, Coblation and powered microdebrider (Straightshot, Medtronic Xomed, Jacksonville, Fla.). However, when compared with standard excisional tonsillectomy, partial tonsillectomy has shown a reduction in postoperative pain only after the first two postoperative days (Chang 2008). While partial tonsillectomy preserves tissue that acts as a "biological dressing" and may reduce pharyngeal muscle inflammation and irritation, there is still an open wound at the tonsillar bed that must heal by secondary intention after surgery. Partial tonsillectomy does not eliminate the problem of secondary post-operative bleeding.

The recent tonsillectomy literature states that "despite significant refinements in surgical technique, instrumentation and anesthesia delivery, postoperative complications and relatively slow return to normal diet and activities remain significant challenges for surgeons and patients alike" (Roth 2008). The morbidities and socioeconomic burden of this very common procedure remain significant. The present invention is directed at providing an apparatus and method for treatment of tonsillar disease that has the following benefits: no postoperative bleeding, greatly reduced postoperative pain, minimal or no intraoperative bleeding, more rapid postoperative return to normal activity, ease of use and brief learning curve, shorter procedure time, reduced costs and economic burden, and ability to be performed under local anesthesia in older children and adults.

SUMMARY OF THE INVENTION

In one aspect, the invention is directed to an apparatus for treatment of soft tissue. The apparatus includes a light source and at least two optical assemblies. Each of the optical assemblies includes at least one optical element and a light-transmitting contact surface configured to transmit a substantially uniform distribution of light therethrough. The apparatus further includes at least two optical transmission devices each disposed between the light source and a corresponding one of the at least two optical assemblies. The apparatus also includes a handpiece to which the at least two optical assemblies are attached, and which is adapted to bring the light-transmitting contact surfaces of the at least two optical assemblies in contact with soft tissue disposed therebetween.

In another aspect of the invention, the apparatus that includes at least two opposed optical assemblies, each configured to produce a substantially uniform distribution of light. The optical assemblies each are coupled by an optical transmission device to a light source. The optical assemblies include an optical element adapted to receive light from the optical transmission device and a light-transmitting contact surface adapted to transmit the light to the soft tissue.

In yet another aspect, the apparatus for irradiating a surface of a tissue. The apparatus includes a housing, a substantially rigid light guide plate having extraction features, and a contact element having a light-transmitting contact surface. The apparatus also includes a cooling layer adjacent to the contact element, such that fluid directed into the cooling layer removes heat from the contact surface before, during, or after light emission. Light directed into the housing of the device and impinging on a lateral edge of the light guide plate propagates through the light guide plate in a direction that is substantially parallel to the tissue surface and is emitted at said contact surface with irradiance that is substantially uniform.

In yet another aspect, the apparatus includes a housing and a substantially rigid light guide plate having extraction features and a contact surface. The apparatus also includes a cooling layer adjacent to the light guide plate, such that fluid directed into the cooling layer removes heat from said contact surface of the light guide plate before, during or after light emission. Light directed into the housing and impinging on the light guide plate propagates through the light guide plate in a direction that is substantially parallel to the tissue surface and is emitted at the contact surface with irradiance that is substantially uniform.

In yet another aspect, the apparatus includes a light source, at least one optical assembly having at least one optical element and a light-transmitting contact surface configured to transmit a substantially uniform distribution of radiation therethrough. The apparatus also includes at least one optical transmission device connected between the light source and the optical assembly and a handpiece having least two distal portions. The distal portions are adapted to grasp the soft tissue therebetween and bring the light-transmitting contact surface of the optical assembly in contact with the soft tissue. The optical assembly is attached to one of the distal portions, the distal portions In one aspect of the invention, the method includes compressing and substantially flattening portions of the tonsil tissue between light-transmitting contact surfaces of two opposed light emitting optical assemblies, introducing light into an optical element of each of the optical assemblies; and irradiating the tonsil tissue by directing the light from the optical element through the light-transmitting contact surfaces to the tonsil tissue in a substantially uniform light distribution.

In another aspect, the method includes compressing and substantially flattening portions of the tonsil tissue between a light-transmitting contact surface and a non-light-emitting surface, introducing light into an optical element; and irradiating the tonsil tissue by directing the light from the optical element through the light-transmitting contact surface to the tonsil tissue in a substantially uniform distribution.

Thus provided is a method and apparatus for treatment of tonsils, using a handpiece with opposing light-transmitting cooled surfaces, such that a tonsil may be held between the surfaces, gently compressed, and irradiated with light from the surfaces, such that the tonsil parenchyma is heated and a biological response that includes immediate and delayed necrotic cell death and delayed tissue involution is induced, and such that the mucosal layer of the tonsil is substantially unheated and thermal injury to the mucosal layer is substantially avoided

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 20 A-D depict optical assemblies comprising a plurality of prisms with reflecting surfaces;

FIGS. 21A-C depict an optical assembly comprising a plurality of elongated mirrors;

FIGS. 24 A and B depict an optical assembly comprising a light guide plate with extraction features;

DETAILED DESCRIPTION OF THE INVENTION

A description of example embodiments of the invention follows.

The present invention provides a method and apparatus for treatment of tonsils, using a handpiece with opposing light-transmitting cooled surfaces, such that a tonsil may be held between the surfaces, gently compressed, and irradiated with light from the surfaces, such that the tonsil parenchyma is heated and a biological response that includes immediate and delayed necrotic cell death and delayed tissue involution is induced, and such that the mucosal layer of the tonsil is substantially unheated and thermal injury to the mucosal layer is substantially avoided.

Figure 1:
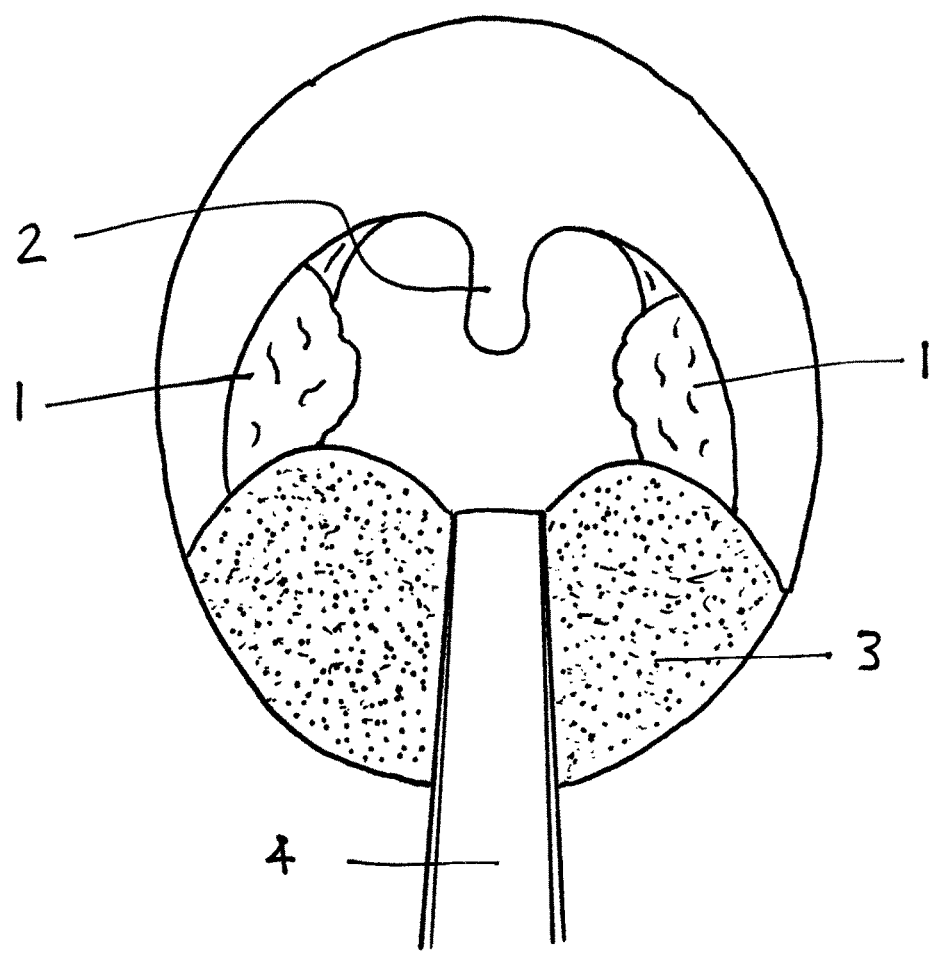
FIG. 1 is a schematic diagram of the oropharynx.

Another objective of the invention is to provide an apparatus and method for heating the tonsils to injure or disrupt the biofilm associated with the tonsil. Specifically, heating of the tonsils may heat a biofilm, bacteria or other infectious matter within the crypts of the tonsils, within the tonsil parenchyma, or at or near the surface of the tonsil, to damage or eliminate a potential source of recurrent infection and/or inflammation of the tonsil The invention may be used to cause shrinkage of the tonsil with concurrent reduction in at least a portion of an existing bio film or infectious matter including bacteria. Alternatively the invention may be used to treat tonsils to induce a reduction in the amount or activity of at least a portion of an existing biofilm or infectious matter including bacteria, with or without concurrently inducing partial or complete shrinkage of the tonsils The tonsils can be observed as a pair of structures on the lateral pharyngeal walls. FIG. 1 is a schematic diagram of the oropharynx including uvula 2 and tongue 3 with a tongue depressor 4 used to visualize the tonsils 1. Tonsils requiring treatment as a result of chronic or recurrent tonsillitis or hypertrophy exhibit a large range in size, from about 3 cm$^3$ to about 18 cm$^3$ per tonsil. Assuming for simplicity a spherical shape, tonsils will range from about 1.8 cm to 3.3 cm in diameter. When a spheroid tonsil is held and compressed between parallel planar contact surfaces, the tonsil will take on an approximately cylindrical shape. If the tonsil has a size of 18 cm$^3$, i.e. is very large, and is compressed to 75% of its spherical diameter, the contact surfaces of the handpiece will be 2.4 cm apart. The two contacting surfaces must each be at least 3.1 cm in diameter, to maximally cover the compressed tonsil surface area. If the same tonsil is compressed to 60% of its spherical diameter the contact elements will be 2.0 cm apart, and the contacting surfaces of the handpiece must be at least 3.4 cm in diameter. If a 3 cm$^3$ small tonsil is compressed to 75% or 60% of its spherical diameter, the separation of the planar contact elements will be 1.3 cm or 1.1 cm, respectively, and the contact elements must have diameter of at least 1.7 and 1.9 cm, respectively. Although it is recognized that actual tonsils deviate from a spherical shape and may be outside the range of 3 cm$^3$ to 18 cm$^3$, and the contact surfaces of the handpiece of the present invention are not necessarily planar or parallel, tonsils held and gently compressed by the contact elements of the present invention can, on the basis of this estimation, be expected to have a thickness of up to about 3 cm, and a diameter of up to about 4 cm.

Therefore, according to the present invention, handpieces with light-transmitting contact surfaces of up to about 4 cm in diameter may be used to transmit light to irradiate and heat tonsil tissue with thickness of up to about 3 cm disposed between those surfaces.

Figure 2:
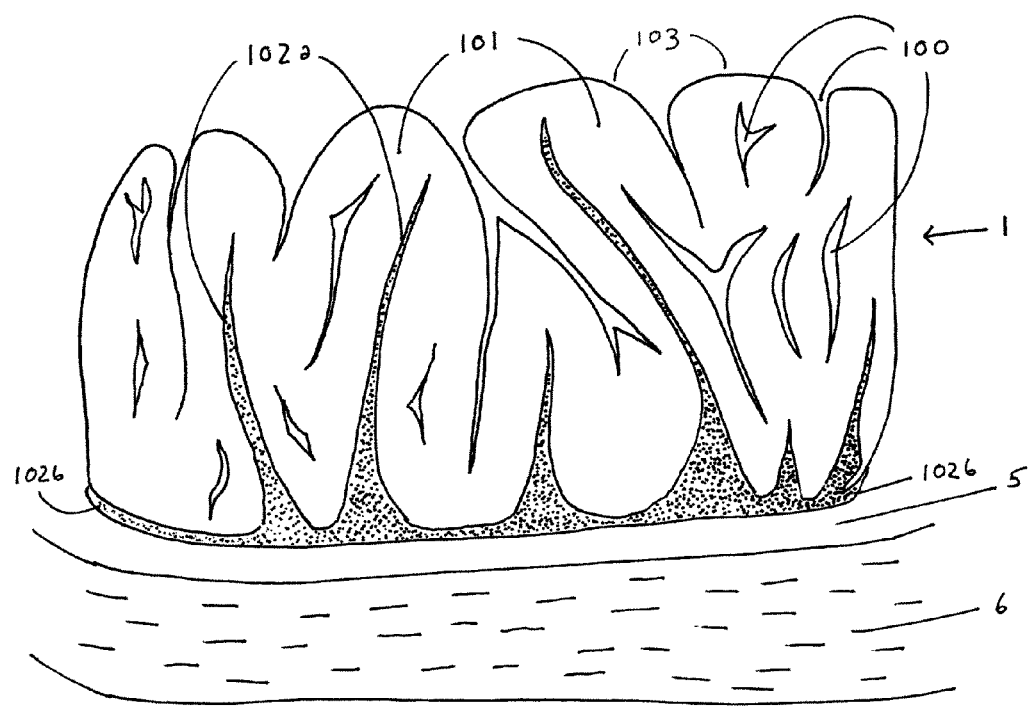
FIG. 2 is a schematic diagram of the anatomy of a tonsil.

Heterogeneity of tonsil tissue composition is also taken into consideration in the present invention. FIG. 2 is a schematic diagram of the anatomy of a tonsil 1, including crypts 100 extending into and branching off in the tonsil. The fibrovascular septa 102a extend from the capsule 102b that lies between the tonsil and the underlying loose connective tissue 5 and the muscle layers 6 of the pharyngeal wall. The mucosal layer 103 covers the entire exposed surface of the tonsil. The tonsil parenchyma 101 is defined herein as the tonsil tissue (including lymphoid cells and tissue, connective or fibrous cells and tissue, and blood vessels and blood vessel cells in the tonsil) excluding the underlying capsule and the mucosal layer of the tonsil surface. Tonsils show great variability in vascularity, size, and relative amount of lymphoid and fibrous tissue as a consequence of the type of tonsillar disease, disease state or severity of the condition, the patient's age, and individual patient variability. The present invention provides methods, devices, and systems that enable the photothermal treatment of heterogeneous and variable tonsils over the wide spectrum of tonsillar disease.

Optical Properties of Tonsil Tissue

Photothermal treatment involves the interaction of biological tissue with light (defined herein as electromagnetic radiation of any wavelength). Light is directed to the tissue such that endogenous (native) or exogenous (added) chromophores within the tissue absorb some or all of the light, thereby generating heat in the tissue to affect a desired physical and/or biological response. The tissue response may be immediate and/or delayed. The principles underlying photothermal treatment are known to those skilled in the art, and these principles have been implemented for treatment of many organs, tissue types and medical conditions. Knowledge of the biological and optical (absorption and scattering) properties of the tissue or tissues involved in the treatment is required for an application of the principles of photothermal treatment to a specific medical problem. In addition to matching the absorption spectrum of the tissue chromophores, the wavelength or wavelengths of light used in the treatment must also be chosen on the basis of its depth of penetration within the tissue, which both scatters and absorbs light. Furthermore, the amount of light delivered to the tissue must be chosen based on the physical dimensions and thermal characteristics of the tissue, such that the absorption of that light leads to the desired temperature increase in the tissue. Still furthermore, knowledge of the biological response of the tissue to elevated temperatures is needed. Yet furthermore, the effect of blood perfusion on the interaction of light with living tissue may need to be taken into account.

Therefore, while the general principles underlying photothermal treatment are generally known by those skilled in the art, knowledge of the optical, thermal, and biological properties of tissue required for application of those general principles to a particular medical problem may be unavailable. For the problem of treating tonsils, data on the optical properties are substantially lacking, and in important wavelength regions are unknown. The biological response of tonsil tissue as a function of heating to specific temperatures for specific times is also unknown. Without these data the response of tonsil tissue to irradiation with light cannot be predicted, and the best parameter ranges for photothermal treatment of tonsils cannot be determined. Herein, as a first step to developing a method and apparatus for treatment of tonsils with light, the optical properties of tonsil tissue over a wide range of wavelengths have been found. Furthermore, the expected variability of those optical properties with tonsil pathology has been found.

For optimal results in photothermal treatment, the penetration depth of the light should be of the same order of magnitude as the thickness of the tissue to be heated. As has been described above, the thickness of a tonsil requiring treatment may in general be expected to be in the range of about 1 cm to about 3 cm, and a surface area of diameter of up to approximately 4 cm, when held between contact surfaces according to the present invention. When intrinsic optical constants (absorption coefficient $\mu_a$, scattering coefficient $\mu_s$, and anisotropy factor g) are known as a function of wavelength for a specific tissue type, the depth of penetration of light in that tissue can be calculated. Optical constants have been experimentally determined for tonsil tissue at only two single wavelengths (1064 nm and 805 nm) in the near infrared (NIR) (Shah 2001). Those wavelengths correspond to the output of two of the most commonly available surgical lasers (neodymium YAG and semiconductor diode), not necessarily to optimal wavelengths for photothermal treatment of tonsils.

Figure 3:
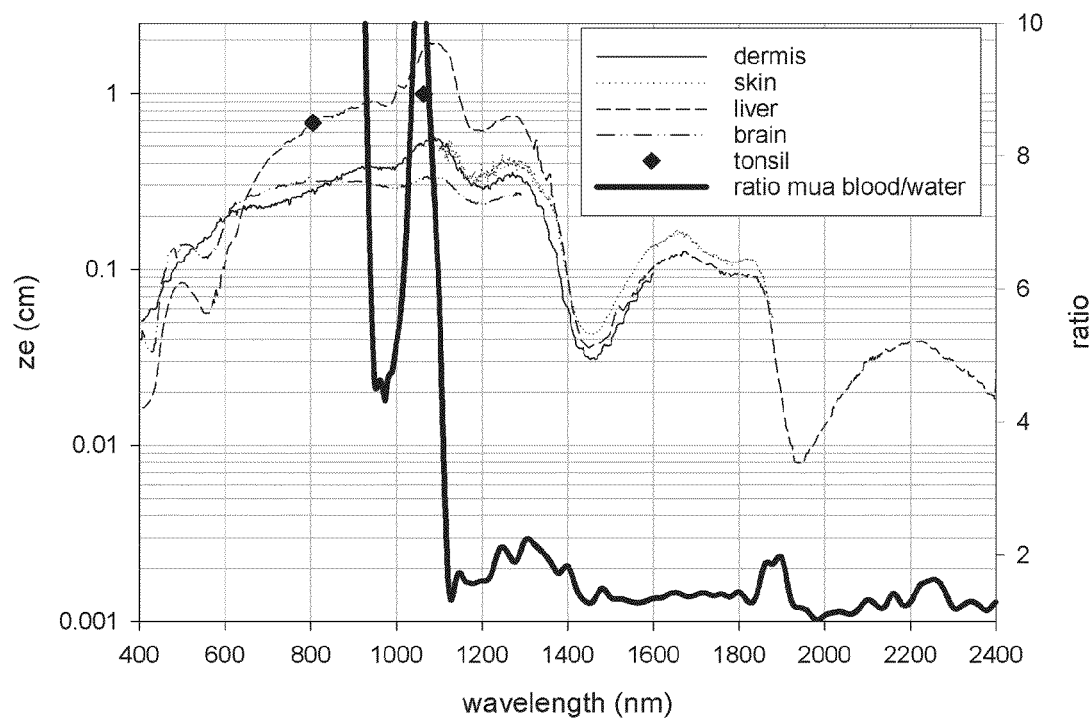
FIG. 3 shows the calculated 1/e depth of penetration of light for various types of soft tissues and the ratio of the absorption coefficient of diluted blood to water.

Herein, as a starting point for solving the problem of tonsil treatment, published data for other soft tissues were examined to find the range of wavelengths most likely to be useful in penetrating and heating tissue to a depth of approximately a centimeter or more. A number of soft tissue types such human dermis, human skin (epidermis and dermis), porcine liver, and human brain have been the subject of past determinations of optical properties over wide wavelength ranges. Herein, graphical data from such reports were digitized using commercially available software (DigitizeIT Version 1.5, Ingo Bormann, Rablstrasse 18, 81669, Munich, Germany) and the penetration depth $z_e$ calculated from the resultant numerical data for each tissue type, to obtain a consistent set of $z_e$ values as a function of wavelength from the data of the different reports. Specifically, the depth $z_e$ where the fluence rate in the tissue falls to a value of 1/e (approximately 37%) of the incident irradiance $\Phi_0$ was calculated using the expression $z_e=\delta(1+\ln(k))$, where $\delta=(3\mu_a(\mu_a+\mu_s(1-g)))^{-1/2}$, and k is the backscatter term which is in turn obtained using the expression $k=3+5.1R_d-2\exp(-9.7R_d)$, with diffuse reflectance $R_d=\exp(-7\delta\mu_a)$. Results of these calculations are shown in FIG. 3, along with results based on the optical constants that had been reported for tonsil tissue at 1064 nm and 805 nm. It can be seen that while the absolute magnitudes of $z_e$ for the various soft tissue types differ, for each type the maximum values are broadly located within the range of approximately 700 nm to approximately 1350 nm. This computational result is consistent with the concept widely known in the art that there is a "therapeutic window" in biological tissue, variously reported as 600 nm to 1200 nm, 600 nm to 1000 nm, 600 nm to 1100 nm, 600 nm to 1400 nm, and so on. More importantly, in said region, the 1/e penetration depths $z_e$ are seen in FIG. 3 to have maximum values ranging from several millimeters to 2 cm, in the region from about 700 nm to 1350 nm. Therefore, it is apparent that for photothermal treatment of soft tissue having thickness of several millimeters to 3 cm, including tonsil tissue being treated according to the present invention, wavelengths of light within the range of approximately 700 nm to approximately 1350 nm are preferred.

Vascularity is another important consideration because the vascular architecture and hence the volume of blood contained within the tonsil and the rate of blood flow to and from the tonsil will vary from patient to patient. The vascularity also depends on the pathologic state of the tonsil. Variability in blood content of the tonsils will introduce a variability in treatment response, if the treatment mechanism is dependent on or influenced by blood. A laser or other light source operating at a wavelength that is strongly absorbed by blood will produce a larger temperature increase in a more highly vascular tonsil. The temperature increase may be localized to the blood vessels of the tonsils and coagulate those structures, or the heat may diffuse out of the tonsillar vessels to heat the surrounding tonsillar parenchyma. Treating the tonsils with light that is highly absorbed by blood will therefore lead to difficulty in controlling the outcome of the procedure.

Another difficulty related to the vascular nature of tonsils is the control of heat transfer. Blood perfusing the tonsils will carry heat out of the organ. If the treatment modality involves heating of the tonsils using light or other energy, blood flow may limit the temperature increase that can be achieved in all or part the organ, thereby limiting treatment response in an unpredictable manner.

FIG. 3 compares the absorption of light by blood to that of absorption by water, throughout the visible and NIR spectral regions. Water is the primary constituent of most soft tissue, including tonsils. The blood absorption coefficients plotted in this figure were obtained by digitizing a published spectrum of fully oxygenated diluted blood (hematocrit 5%) over a large wavelength range. The ratio of the absorption coefficients of the diluted blood to those of water are calculated and plotted as a solid line in FIG. 3. It can be seen that from approximately 1100 nm to approximately 2500 nm, the ratio of the absorption of diluted blood to water is relatively low (less than approximately 2), whereas at wavelengths shorter than approximately 1100 nm, this ratio is substantially greater. The high ratio at shorter wavelengths is due to the presence of the chromophore oxyhemoglobin in blood, which absorbs visible and NIR light much more strongly than does water. At the longer NIR wavelengths greater than approximately 1100 nm, blood and water have similar absorption characteristics. The ratios of absorption coefficients may be higher in the case of whole undiluted blood, but can still be divided into a region consisting of visible and NIR wavelengths up to approximately 1100 nm where the ratio is very high, and a region from approximately 1100 nm to at least approximately 2500 nm in the NIR where the ratio is substantially lower and relatively constant.

The calculated ratios of absorption coefficients in FIG. 3 indicate that when exposed to wavelengths of light shorter than approximately 1100 nm, blood vessels in tonsils will absorb much more strongly than the surrounding nonvascular tonsillar tissue. At wavelengths longer than approximately 1100 nm, absorption by vascular and nonvascular tissue is more similar. Therefore, vascular and nonvascular tissue will react more consistently and predictably to irradiation at wavelengths of approximately 1100 nm to at least approximately 2500 nm, than it will at shorter wavelengths. A substantially consistent reaction to vascular and nonvascular tissue is highly desirable when the vascular component of the tissue being treated varies between patients and with disease condition.

The range of wavelengths corresponding to deep penetration of light (approximately 700 nm to 1350 nm) overlaps with the range (approximately 1100 nm and longer) where the ratio of absorption by blood to water is relatively low and constant. The overlapping range is approximately 1100 nm to 1350 nm. Therefore, according to a more preferred embodiment of the invention, NIR wavelengths in the range of approximately 1100 nm to approximately 1350 nm are used for photothermal treatment of tonsils.

Although the exemplary soft tissues of FIG. 1 show similar trends in depth of penetration as a function of wavelength, there are very large differences in the actual $z_e$ values between tissue types for any given wavelength. Therefore, to further characterize the effect of NIR light in the 1100 nm to 1350 nm range on tonsils and to determine the most preferred wavelengths within this range, as well as delivered powers, irradiation times, and other parameters for photothermal treatment of tonsils, wavelength-specific optical constants for tonsillar tissue are required. As noted previously, however, the intrinsic optical constants for tonsils have been measured at only two wavelengths, 1064 nm and 805 nm. Both of these wavelengths are outside the preferred range of about 1100 nm to 1350 nm as has been determined herein. Thus, in order to predict the effect of photothermal treatment within the preferred range, optical constants for tonsils in the unknown range are found herein based on an approach that uses available properties of tonsil tissue constituents and chromophores. As described previously, tonsil tissue comprises lymphoid, mucosal, and fibrovascular elements, therefore the relevant tissue chromophores are taken herein to be cellular and extracellular water, blood (or more specifically oxygenated and deoxygenated hemoglobins), and proteins including primarily collagen of the connective tissue.

Figure 4:
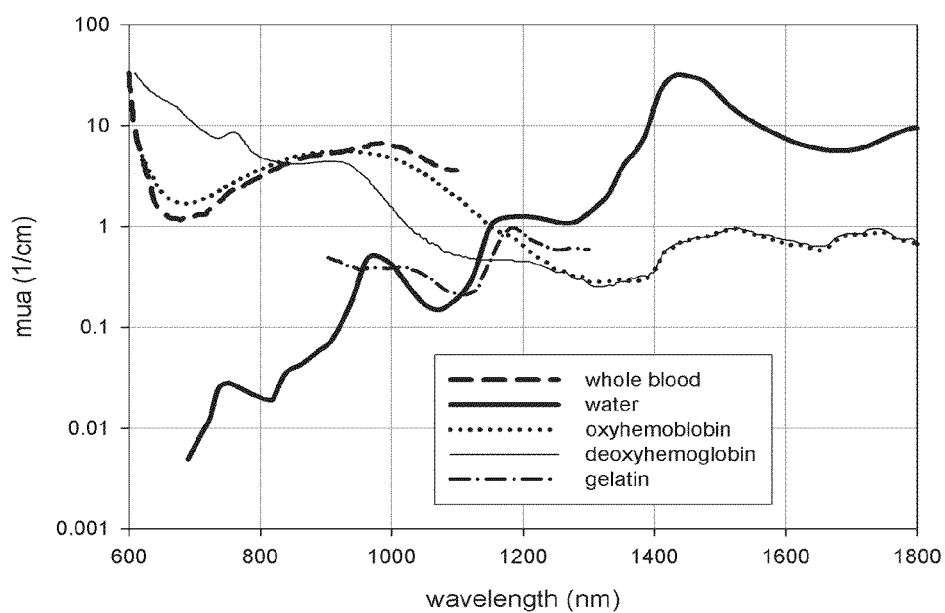
FIG. 4 shows the absorption spectra of oxyhemoglobin, deoxyhemoglobin, water, whole blood, and dry gelatin.

To determine the spectral contribution of blood in the NIR wavelength range at any oxygenation level, NIR absorption of oxyhemoglobin and deoxyhemoglobin for hemoglobin concentrations corresponding to 42.1% hematocrit were calculated. Results are in good agreement with whole blood data in the region of overlap less than about 1100 nm where water absorption in low (FIG. 4). Measurements reported for soft tissue water content do not distinguish between the water present in blood vessels and in non-vascular tissue. For this reason it is appropriate to combine the hemoglobin content with the total water content to represent the combination of blood and water in soft tissue.

The absorption coefficient of the appropriate mixture of oxy- and deoxyhemoglobin as a function of wavelength, calculated as described above for blood content of a specified oxygen saturation and hematocrit, is then used to construct the absorption coefficient of tonsillar tissue, based on its components of blood, water, and collagen. The fractional mass of total water in non-adipose soft tissue is about 0.80. Blood content is highly variable but values of 2 to 6% are typical for normal tissue. Blood hematocrit of 42.1 percent is normal and oxygen saturation of 0.8 is within the typical range for well-oxygenated tissue. It is assumed herein that the remainder of the tissue is collagen. The absorption coefficient of the tissue may then be calculated from the absorption coefficients of the constituents, weighted by their percentage of the total tissue. For collagen, gelatin data were used (shown in FIG. 4). Results of this calculation are shown in FIG. 5, for the entire spectral region (900 nm to 1300 nm) for which the collagen (gelatin) data are available.

Figure 5:
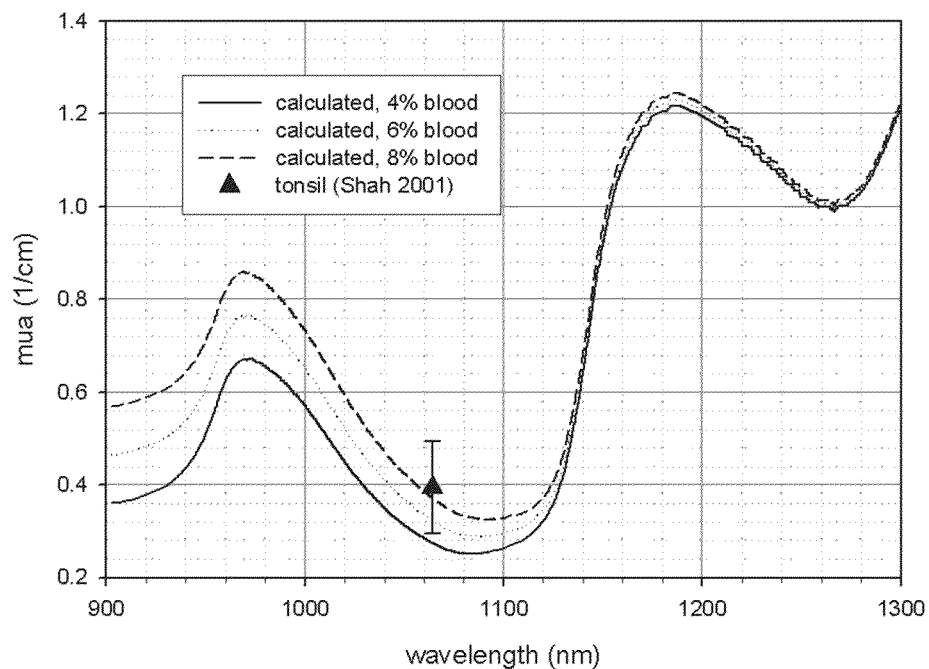
FIG. 5 depicts the calculated absorption spectra of tonsil tissue in the 900 to 1300 nm region.

The calculated spectra are found to be in excellent agreement with the one experimental value for tonsil tissue available from the literature within this range, at 1064 nm, as shown in FIG. 5, confirming the validity and accuracy of the theoretical approach developed herein to find the previously unknown optical properties of tonsil tissue. The literature value was reported as an average of measurements from tonsil specimens excised in tonsillectomy (Shah 2001), and can be assumed to correspond to a typical human tonsil requiring tonsillectomy. The mean experimental value for the absorption coefficient for human tonsil at 1064 nm is closest to the calculated value for tissue with a blood content of 6%, however, within the preferred region from approximately 1100 nm to 1350 nm, it can be seen from FIG. 5 that the calculated tonsil tissue absorption coefficient is substantially invariant with respect to blood content. Thus in calculating the absorption coefficient of tonsil tissue, the results are nearly independent of tonsil vascularity within that wavelength range, in accordance with an objective of a preferred embodiment of present invention to provide a treatment that is not affected by variations in tonsil vascularity.

Based on the above findings, the absorption coefficients $\mu_a$ as a function of wavelength, found as described above, will be used herein for the previously unknown tonsil tissue values within the optimal wavelength range of approximately 1100 nm to approximately 1350 nm.

Figure 6:
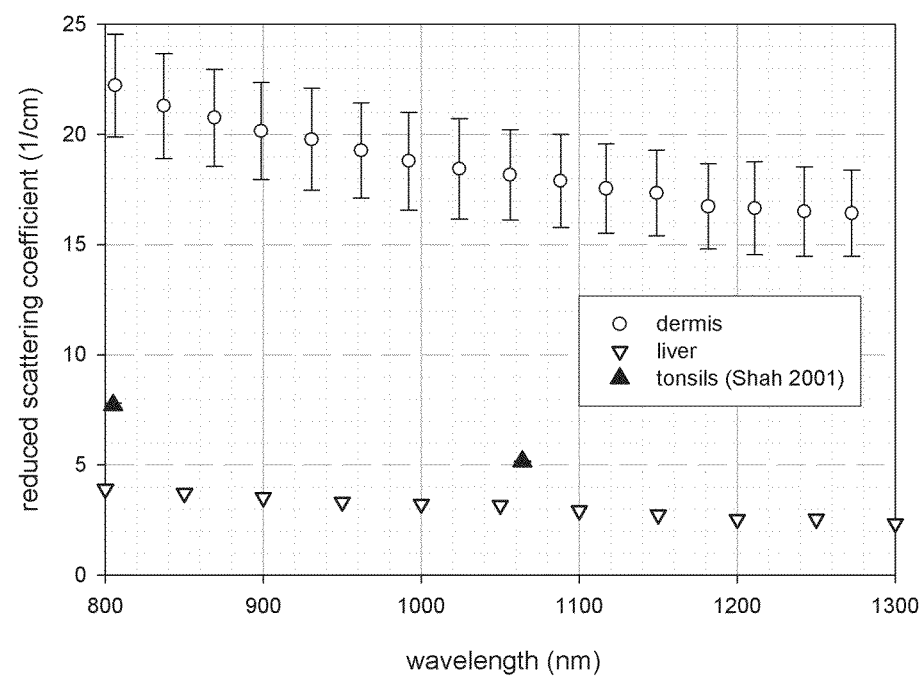
FIG. 6 depicts reduced scattering coefficients for tissue.

Experimental measurements of scattering coefficients $\mu_s$ (or reduced scattering coefficient $\mu_s'=\mu_s(1-g)$) reported in the literature for a wide variety of soft tissues show a continuous decrease with increasing wavelength. The available data for tonsils are $\mu_s=72.7\pm1.7$ cm$^{-1}$, g=0.894±0.003 at 805 nm, and $\mu_s=52.0\pm0.65$ cm$^{-1}$, g=0.901±0.005 at 1064 nm (Shah 2001). These data are consistent with decreased scattering at longer wavelengths. The reduced scattering coefficient $\mu_s'$ for tonsil tissue is shown in FIG. 6 along with literature values for $\mu_s'$ for dermis and liver. Dermis is selected because it is mainly connective tissue and highly scattering, while liver parenchyma is primarily cellular and less scattering; however values for both tissue types are seen to be approximately linear over the 800 nm to 1300 nm range. Tonsils, which are primarily composed of cellular lymphoid tissue but with a lesser component of connective tissue in the mucosal layer and fibrovascular septa, have scattering coefficients that are slightly larger than those of cellular liver. Based on this reasoning, for wavelengths in the 1100 nm to 1300 nm region the values of $\mu_s$ for tonsils are estimated herein by a linear extrapolation from the Shah data points; a value of 0.9 will be used for the anisotropy factor g.

The table below summarizes the complete set of intrinsic optical constants for tonsil tissue at selected wavelengths within the 1100 nm to 1350 nm region, as found here according to the methods described above. Also given is the 1/e depth of penetration $z_e$ calculated from these intrinsic optical constants.

TABLE

| wavelength (nm) | $\mu_a$ (cm$^1$) | $\mu_s$ (cm$^{-1}$) | g | $z_e$ (cm) |
| --- | --- | --- | --- | --- |
| 1100 | 0.33 | 49.1 | 0.90 | 1.13 |
| 1110 | 0.34 | 48.3 | 0.90 | 1.11 |
| 1120 | 0.37 | 47.5 | 0.90 | 1.06 |
| 1130 | 0.47 | 46.7 | 0.90 | 0.92 |
| 1140 | 0.68 | 45.9 | 0.90 | 0.72 |
| 1150 | 0.95 | 45.1 | 0.90 | 0.58 |
| 1200 | 1.22 | 41.1 | 0.90 | 0.49 |
| 1250 | 1.04 | 37.1 | 0.90 | 0.57 |
| 1300 | 1.21 | 33.1 | 0.90 | 0.52 |

The most deeply penetrating wavelengths are between 1100 nm to 1130 nm, where $z_e$ is approximately 1 cm; other wavelengths within the range of 1150 nm to 1350 nm have $z_e$ values of several millimeters. Therefore, the most preferred wavelength range for tonsil phototherapy according to the present invention is approximately 1100 nm to approximately 1140 nm.

Biological Response of Tonsil Tissue to Heat

A correlation between temperature increase and cell death, which varies with tissue type, has also previously been unknown for tonsil tissue. This information is needed to determine the target temperature for photothermal treatment of tonsils.

Tonsil samples were obtained from a hospital tissue bank, from a total of five patients aged 3 to 13 yrs (mean 5.4 yrs), preconsented by tissue bank personnel, and de-identified. The tonsils were received fresh within one hour of completion of tonsillectomy, and were serially sectioned in 1.5 mm increments perpendicular to the long axis. After tissue slices needed for patient care were taken, the remaining tissue was used for the study. Slices were representative central cross sections of the tonsils, and were maintained on saline-soaked gauze at room temperature prior to heating. Twenty-eight tonsil cross sections were exposed to temperatures of 40 to 70° C., at 5° C. intervals, for periods of 1, 3, 5, and 7 minutes, using a 2 liter thermostat-controlled saline bath. The bath was stabilized at the aforementioned temperatures for 5 minutes prior to tissue heating, using two NIST calibrated thermometers. Exposure to each of the seven temperatures was performed using tissue from a single patient. Tissue from two of the five patients was sufficient to be used for two different temperatures.

After removal from the saline bath, the cross sections were immediately submerged in 1 liter of saline at 4 to 10° C. for a period of 5 minutes, and then maintained at room temperature on saline-soaked gauze for 2 hours to allow for inactivation of cellular enzymes in the devitalized cells. Each of the 28 cross sections was frozen to −25° C. in OCT embedding media and cryosectioned at 7 microns onto labeled charge-coated slides. All sections were taken within 100 microns of the surface of the tissue. (At the surface, the tissue will have equilibrated most rapidly with the saline bath.) The cryosections were subsequently stained with nitroblue tetrazolium chloride (NBTC) for microscopic analysis. Blue staining with NBTC is indicative of mitochondrial enzyme NADPH diaphorase activity; pale yellow color correlates with cell death.

Figure 7:
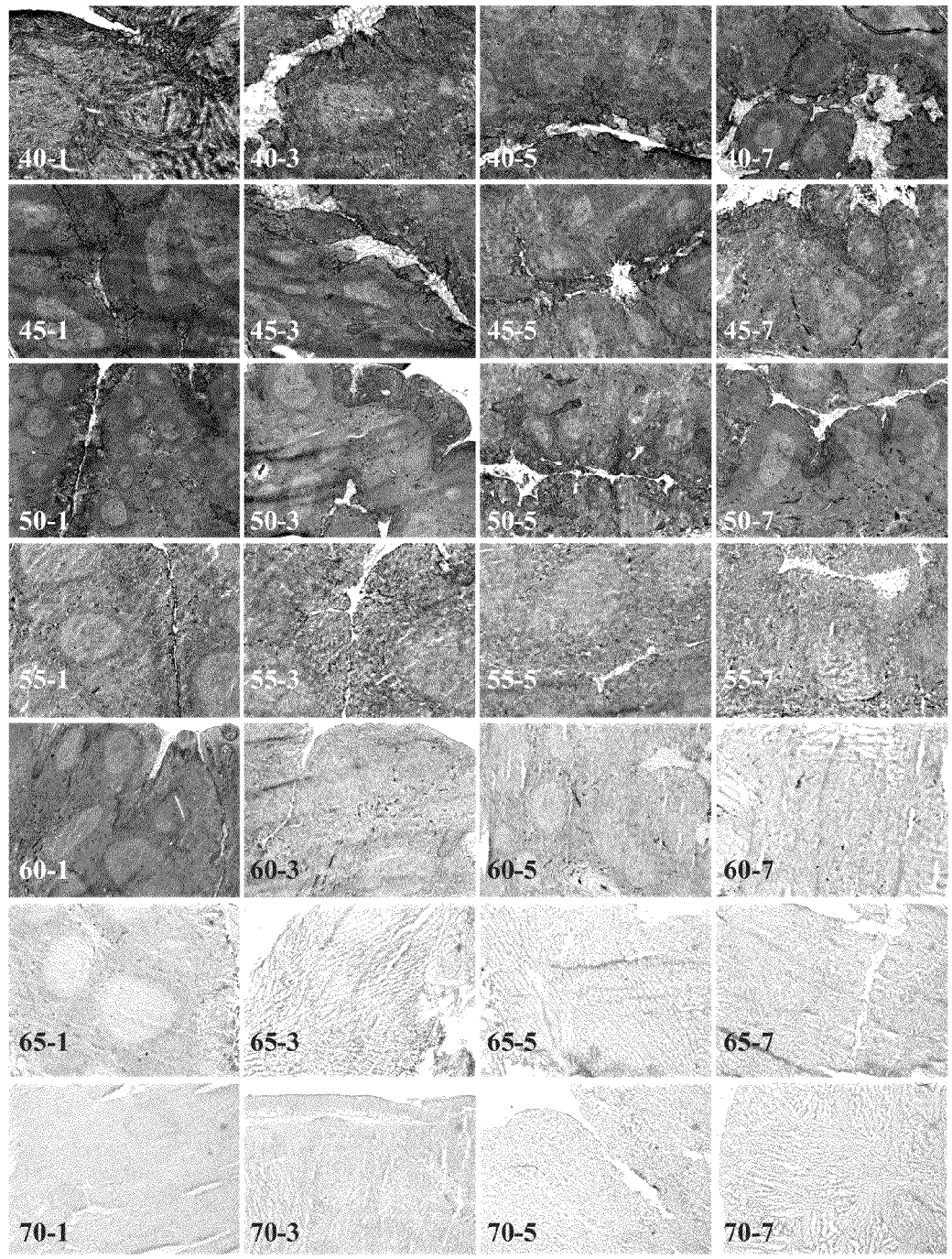
FIG. 7 shows histological results of human tonsil tissue heated at 40 to 70° C., for 1 to 7 minutes.

FIG. 7 provides the results of the tonsil samples described above. The figure includes eight rows each having four photographs of cross sections. Each row contains cross sections of samples exposed at a particular temperature. For example, the top row depicts samples exposed at 40° C., while the second row shows samples exposed at 45° C. Each column indicates the exposure time. For example, the far left column includes cross sections of samples exposed for 1 minute, while the far right column includes cross sections of samples exposed for 7 minutes.

At temperatures of 40 and 45° C., the tissue has the dark blue color characteristic of complete viability at all four time exposures. At 50° C., there is possible, very slight yellowing at the longest time exposures. Tissues exposed to temperatures of 55 to 65° C. are bluish-yellow, corresponding to a transitioning between viable and dead, with decreasing viability with increasing exposure times. At a 7 min exposure at 60° C., and at a 1 min exposure at 65° C. there some blue staining remaining within pale yellow areas. At 70° C., and at 65° C. for longer exposures, the tissue is uniformly yellow, indicating that the tissue is completely devitalized.

This preliminary in vitro experiment characterizes direct necrotic cell kill, which may be augmented in vivo by secondary mechanisms including vascular stasis and ischemia. Inflammation is also likely to occur as cytokines and chemokines are produced in response to cell necrosis. Therefore, according to the invention, temperature/time combinations may be employed that correspond to transitioning tissue, that is, tissue that comprises at least some viable cells and at least some necrotic cells immediately after completion of irradiation, with the expectation that further necrosis, complete devitalization and involution of parenchymal tissue of the tonsil will occur in vivo over time after the photothermal irradiation is complete. Reduction in tonsil size is not expected in the immediate postoperative period, following photothermal treatment. Reduction in size will occur during a period of days to weeks after the treatment, as cellular material from directly killed cells is absorbed, and more tonsil cells are killed by secondary mechanisms and their material is subsequently broken down and removed by a wound healing response.

An undesirable result of heating tonsil tissue would be immediate complete cell death with thermal fixation. Such tissue would be coagulated and slightly shrunken, but resistant to tissue breakdown and removal because of the lack of functional vessels. A foreign body reaction may result. According to the invention, the photothermal treatment of tonsils should avoid higher temperatures and/or longer irradiation times that result in thermal fixation of tonsil parenchyma.

For heating periods of at least one and not more than 7 minutes, this experiment indicates that tonsil tissue should be maintained in the range of 50 to 65° C., to induce subtotal direct cell death and transitioning tissue. For periods of less than one minute, temperatures higher than 60 to 65° C. may be appropriate. These findings obtained from water bath experiments, in which the tissue temperature rise time is negligible compared to the total heat exposure time, are expected to differ in the case of photothermal treatment using the apparatus of the invention, wherein absorption by the tonsil tissue of light emitted from the contact surfaces will lead to a more gradual temperature rise within the tissue. Thus, a 1 min exposure which includes a significant rise time and leads to a maximum temperature of 65° C. will produce less cell death than a 65° C. exposure for 1 min. Consequently, the experiments herein indicate that for the method and apparatus of the invention, when irradiation times of between 1 and 7 min are used, the target temperature of the tonsil parenchyma should be at least approximately 50 to 65° C. When irradiation times of substantially less than 1 min are used, the target temperature of the parenchymal tissue should be least approximately 60 to 65° C. As defined here, target temperature is the parenchymal temperature required during at least a portion of the time of irradiation of the tonsil, to induce substantial postoperative involution of the tonsil as a result of immediate direct death of a at least some tonsillar parenchymal cells and delayed death of a substantial part of the remaining parenchymal cells.

Parameters for Tonsil Treatment Using Light

With the optical constants found herein as described previously, it is possible to perform model calculations for the interaction of light with tonsils of various sizes and conditions, to determine requirements for achieving the temperatures identified above as corresponding to a transition between completely viable tissue and completely necrotic tissue at a point in time when irradiation is complete.

The constants in the Table correspond generally to tissue of tonsils requiring tonsillectomy. It is known that in hypertrophy tonsils expand in size by increasing the size of the lymphoid component, whereas sclerotic tonsils found in some patients after repeated tonsillar infections may have a relative increase in the connective tissue component. Sclerotic tonsils may therefore be expected to be more highly scattering so that light of a given wavelength will penetrate less deeply. Therefore, model calculations can be performed for more or less sclerotic tonsils by varying the scattering coefficient from the value in the table.

Herein, the approximate practical upper limit of the irradiation time for a single tonsil in an operating room environment is assumed to be 10 min. Preferably, the irradiation time is less than 5 min. More preferably the irradiation time is less than 3 min. Most preferably, the irradiation time in the operating room environment is less than 1 min. It is recognized however, that in a clinic or office setting somewhat longer irradiation times may be acceptable, due to the many other advantages of treatment under local anesthesia rather than in an operating room.

The experiments using tonsil tissue and vital stain, described previously, indicate that tonsil cell viability is highly dependent on temperature. Therefore, for a uniform, complete, and predictable clinical outcome from a photothermal treatment, heating of substantially all of the tonsil parenchyma to a target temperature is required.

This objective is achieved with the method and apparatus of the present invention by irradiating the tonsil tissue from two opposing light-transmitting surfaces, and by using light with deeply penetrating wavelengths, preferably using a wavelength or wavelengths that is between about 1100 nm and 1350 nm. Preferably, the tonsil is heated symmetrically over substantially its full width, to a target temperature corresponding to transitioning tissue, defined as tissue that comprises at least some viable cells and at least some necrotic cells, at some point in time during irradiation.

Figure 8:
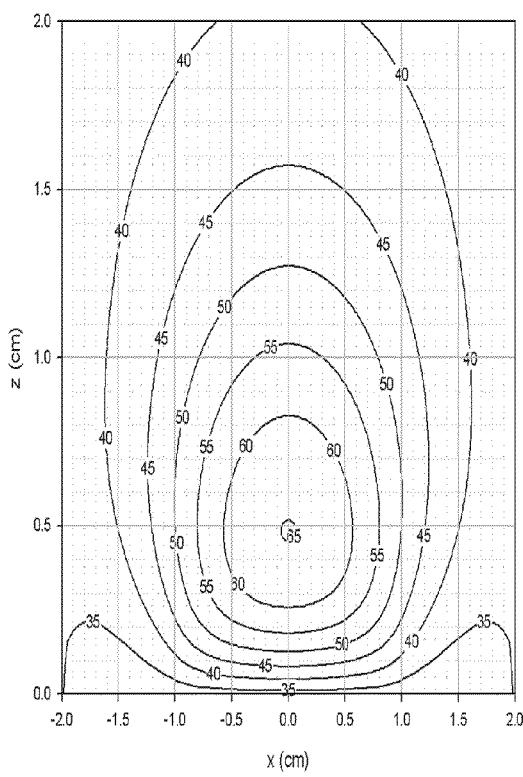
FIG. 8 shows the results of model calculations for an irradiation of tonsils with 1120 nm light in a 20 mm diameter, collimated beam at a power of 10 W, for 2 min through a cooled sapphire element.
Figure 9:
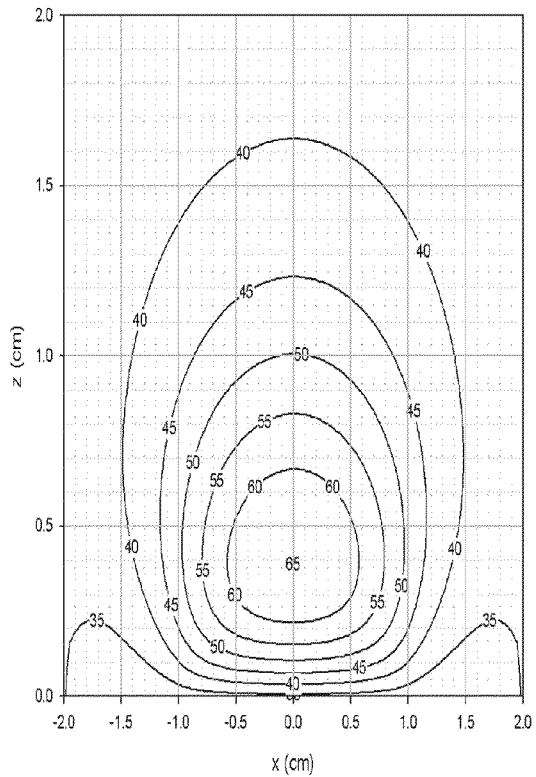
FIG. 9 shows the results of model calculations for an irradiation of tonsils with 1120 nm light in a 20 mm diameter, collimated beam at a power of 7.5 W, for 6 min through a cooled sapphire element.

In an initial calculation of the interaction of light with tonsil tissue, a simple model was implemented in which a slab of tonsil tissue of arbitrary thickness was located under a sapphire window. Collimated light at 1120 nm was directed to the tonsil tissue through the window. The incident beam diameter on the tissue surface was 20 mm. The tissue was given an initial physiologic temperature of 37° C., and for its thermal properties the values for another lymphoid tissue, human spleen, were used. The sapphire window was held at a constant temperature of 30° C. Monte Carlo calculations of photon propagation and heat transfer calculations were performed over the interaction volume, varying the incident laser power and the total irradiation time, and the resultant tissue temperature was plotted, as in FIGS. 8 and 9. It was found that with a 10 W incident beam, a temperature of 60 to 65° C. is reached over a region of the tonsil tissue centered at about 4 mm under the sapphire surface after 2 minutes of irradiation (FIG. 8). With a 7.5 W beam, it requires 6 minutes for the 60 to 65° C. region to form, but that heated region extends more deeply into the tissue (FIG. 9). With a 5 W beam, calculations indicate that it is not possible to achieve a 60° C. heated region under the window with irradiation times of 10 minutes or less.

Considering the case of a tonsil with size that is approximately average for those removed in tonsillectomy procedures, 9 cm³, and compressed to a thickness of about 75% of its spherical diameter when held between two flat contact elements separated by 2 cm, the above initial calculations indicate that with emission of 1120 nm radiation in a 20 mm circular spot from only one contact surface there can be, with proper choice of laser power and irradiation time, some heating throughout the full 2 cm thickness of the tonsil tissue, but that the heating will be substantially uneven over the full thickness, and the irradiation time will be relatively long. The maximum temperature at the end of the laser irradiation time is located at a point 5 mm or closer to the light-transmitting contact element.

To demonstrate the effect of irradiation from two opposing contact surfaces in producing a more symmetrical heat distribution of the full thickness of the tonsil, model calculations were performed for exemplary cases of tonsils of small, average, and large sizes, in a cylindrical geometry representative of the form taken by the tonsil when held between two flat light-transmitting contact surfaces.

Figure 10:
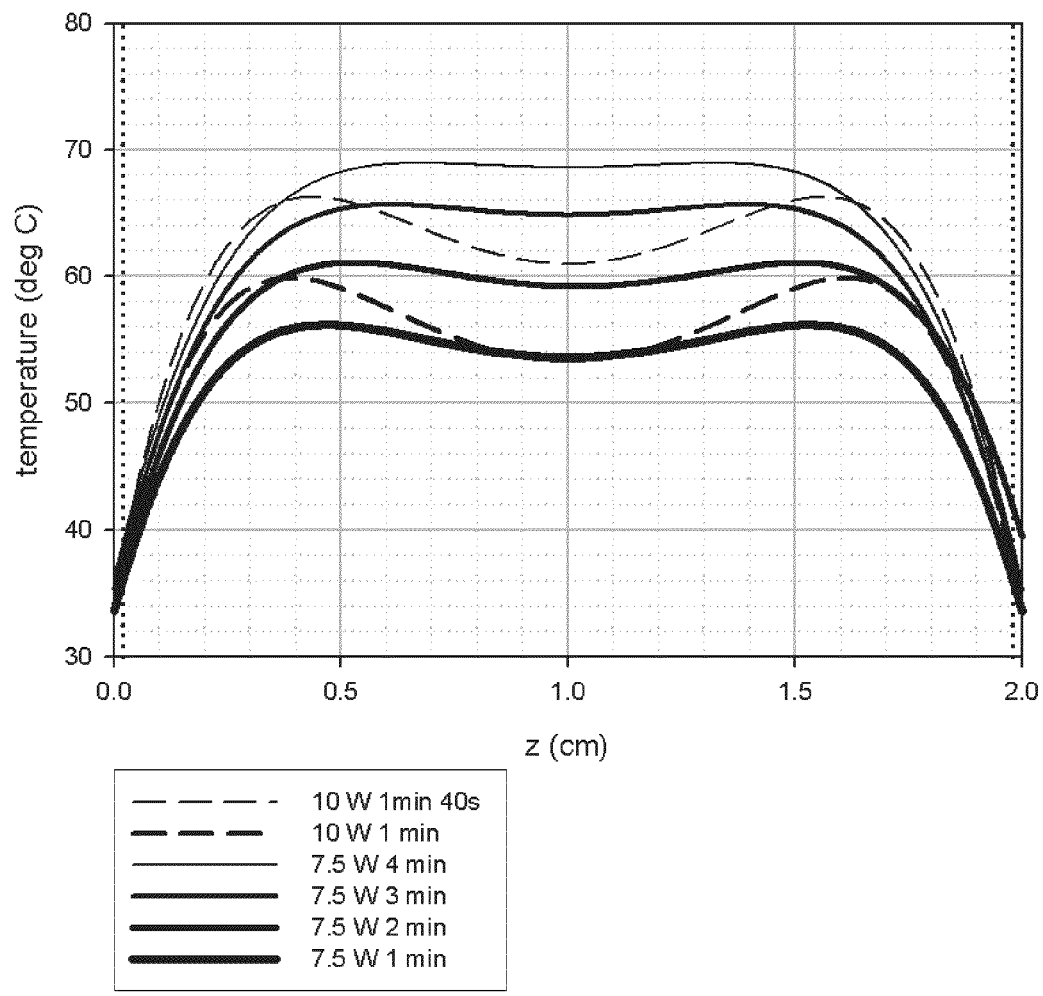
FIG. 10 shows the results of model calculations for the case of a tonsil of approximately average size, with thickness 2 cm between two light-emitting sapphire contact elements.

FIG. 10 shows model calculation results for an exemplary average sized tonsil that is 2 cm in thickness when held between two parallel light-transmitting windows made of sapphire. This thickness corresponds to about 75% of the spherical diameter of 2.6 cm for a 9 g tonsil. Results are given as the temperature at the end of the light exposure time along an axis through the center of the tonsil between the two contact elements, which are maintained at a temperature of 30° C., that is, slightly cooled relative to physiologic temperature but still above room temperature. It is found that a collimated 20 mm diameter, 7.5 W 1120 nm beam from each contact element produces a region of substantially constant temperature in the central portion of the tonsil, with the temperature after exposures of 1 to 4 minutes ranging from about 54° C. to about 69° C. Using a 10 W beam from each surface to achieve temperatures within this range, the temperature distribution is symmetrical but less even across the full thickness. Longer irradiation times (lower incident irradiances) increase relative heating at depth for a more even distribution, for a given amount of total delivered light energy. These calculations indicate that at 1120 nm with total laser power on the order of 20 watts or less (10 watts or less per light-transmitting element, when 2 light emitting elements are used), a tonsil of the size that is typically removed in tonsillectomy may be substantially heated to a temperature of about 55 to about 70° C. in a time period that is sufficiently short to be advantageous in a clinical or operative setting. The approximate location of the mucosal layer is delineated in FIG. 10 by the dotted vertical lines. It is found that the first 200 microns of tissue adjacent to the cooled sapphire surface, corresponding to the location of the mucosal layer of the tonsil surface, including epithelium and lamina propria, are maintained at a low enough temperature that this layer may be expected to be substantially uninjured by the radiation.

Figure 11:
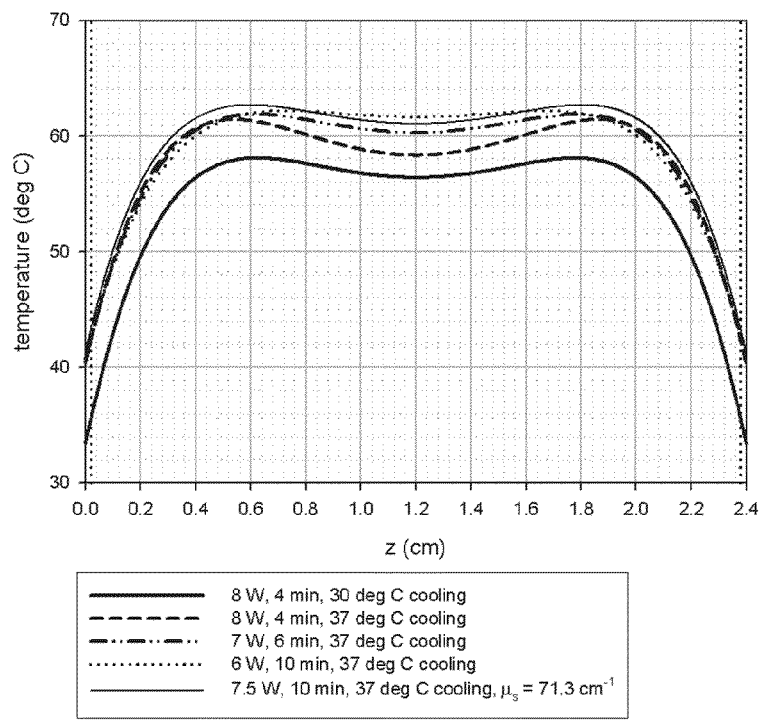
FIG. 11 shows the results of model calculations for the case of a large tonsil, with thickness 2.4 cm between two light-emitting sapphire contact elements.

FIG. 11 shows the results of a calculation for an exemplary large tonsil, with size 18 cm³. The sapphire contact elements are 2.4 cm apart (tonsil compression to about 75% of spherical diameter). Here, the collimated beam has been expanded to 26 mm diameter, to better match the diameter of the tonsil tissue compressed between the two light-transmitting contact elements. Exposure times of 10 minutes or less produce tonsil temperatures of about 60° C. with powers of 6 to 8 W from each contact element. It is found that the mucosal layer remains at a temperature well below the threshold for thermal injury when the sapphire contact elements are maintained at 37° C. (physiological tissue temperature) during irradiation. When the sapphire temperature is maintained at 30° C. rather than 37° C., the calculations indicate that both the tonsil mucosal surface and the interior parenchyma are heated less during exposure with identical irradiation parameters.

Figure 12:
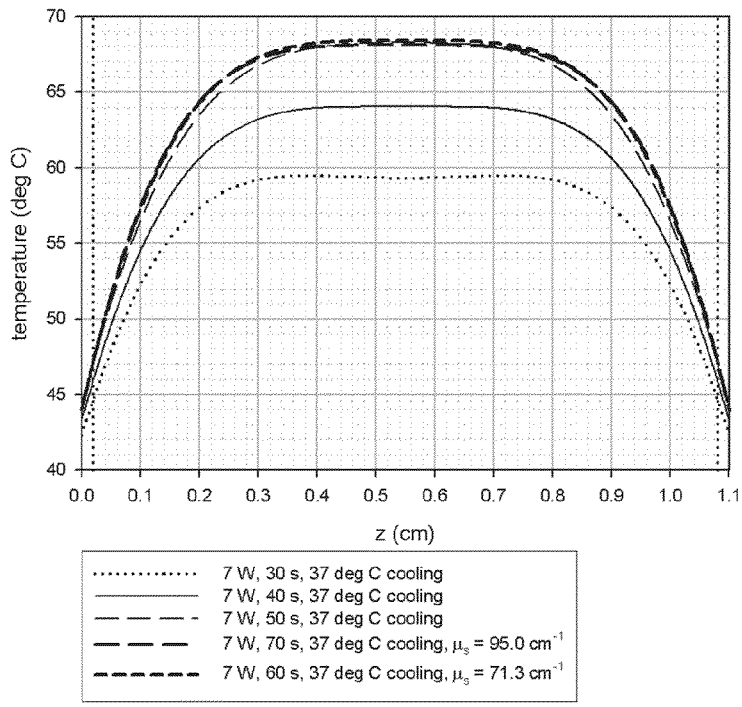
FIG. 12 shows the results of model calculations for the case of a small tonsil, with thickness 1.1 cm between two light-emitting sapphire contact elements.

FIG. 12 shows the results for an exemplary small tonsil, with size 3 cm³. In the model calculation performed in this case, the tonsil was held between sapphire surfaces 1.1 cm apart (compression of tonsil to approximately 60% spherical diameter). Matching collimated beams 1.6 cm in diameter were used to irradiate the tonsil from each contact element. It can be seen that the temperature at the center of the tonsil increases by approximately 0.5° C. per second of irradiation, at a power of 7 W from each element. Thus, with these model calculations it is found that while total irradiation times required to reach at least target temperatures in the tonsil are advantageously short—less than one minute—the rate of temperature increase is slow enough that it may be easily monitored.

As noted previously, tonsils that require treatment are highly variable not only in size but also in vascularity and the relative amount of lymphoid and fibrovascular or fibrotic tissue. Tonsil vascularity as a treatment variable is minimized in the present invention by the aspect of gently compressing the tonsil to substantially reduce both blood flow and blood volume. However, fibrotic or sclerotic tonsils, or tonsils with especially many and/or thickened fibrovascular septa, are by the nature of their composition characterized by a relatively large connective tissue component. This connective tissue component will cause increased scattering of light within the tonsil. To determine how this variability in tonsil composition will affect treatment, model calculations were performed for the exemplary small, average, and large tonsils using a scattering coefficient $\mu_s$ that is 1.5 or 2.0 times greater than the value used in the above calculations for typical tonsils. Results for the small tonsils are included in FIG. 12, where it can be seen that if the scattering coefficient is increased by 50 percent (100 percent) the irradiation time required for equivalent heating with 7 W power is 20 percent (40 percent) greater. For very large tonsils (FIG. 11), which are less likely than small tonsils to be highly fibrotic, nearly equivalent heating can be achieved with a 50 percent increase in scattering coefficient by increasing the power at the same exposure time. These calculations indicate that substantially the same heating effect can be produced in more fibrotic tonsils, with the present invention, by increasing the irradiation time, laser power, or both.

In the models used in the above calculations, the contact elements serve to cool the tonsil surface during irradiation and prevent thermal injury to the mucosal layer. An objective of the present invention is to heat the mucosal layer of the tonsil less than tissue in the interior of the tonsil. The mucosal layer, consisting of the epithelium and the underlying lamina propria, is approximately 200 microns in thickness. According to the invention, all or most of the epithelium is maintained at a temperature less than about 50° C. during irradiation to avoid substantial thermal injury. Preferably, all or most of the mucosal layer is maintained at a temperature less than about 50° C. during laser irradiation to avoid substantial thermal injury. The above model calculations indicate that use of light-transmitting contact elements made of sapphire, a material with large heat transfer coefficient, allows the full thickness of the mucosal layer to be maintained at a temperature of less than about 50° C. during irradiation, when said sapphire element is maintained at moderate temperature of 37° C. or below. The ability to protect the epithelium and/or mucosal layer of the tonsil with only moderate cooling temperature is an important advantage of using deeply penetrating wavelengths in the 1100 to 1350 nm range, including 1120 nm as in the mathematical model here. When more superficially absorbing wavelengths are used, more aggressive cooling may be required to prevent thermal injury to the mucosal surface layer or epithelium of the tonsil. More aggressive cooling would include contact cooling with sapphire or other surface materials maintained at temperatures approximately at or below the freezing point of tissue, or application of cryogenic fluids or cold gases directly to the tonsil tissue surface. Imbalances between superficial heating and aggressive cooling of the tissue or failures of the cooling system can rapidly lead to unintended tissue injury. More aggressive cooling also increases power consumption, device complexity, and costs. According to the present invention, the contact surface has a temperature sufficient to cool and protect the mucosal layer of the tonsil during irradiation. The contact surface may passively or actively cool the mucosal layer. A passively cooling contact surface may be a window made of a thermally conductive material, that is at room temperature before being brought into contact with a tonsil, or that has been precooled by placement in a cold environment prior to contacting the tonsil. An actively cooling contact surface may be in thermal contact with a cooling fluid before, during, and/or after irradiation. Preferably, the cooling of the contact surface is sufficient to protect the mucosal layer, but not sufficient to substantially increase the amount of irradiation required to heat the tonsil parenchyma.

Another objective of the invention is to provide an apparatus and method for heating the tonsils to injure or disrupt the biofilm within the tonsil. Specifically, heating of the tonsils may heat a biofilm or bacteria or other infectious matter within the crypts of the tonsils, to damage or eliminate a potential source of recurrent infection and/or inflammation of the tonsil The invention may be used to cause involution of the tonsil with concurrent reduction in at least a portion of an existing biofilm or infectious matter including bacteria. Alternatively the invention may be used to treat tonsils to induce a reduction in the amount or activity of at least a portion of an existing biofilm or infectious matter including bacteria, with or without concurrently inducing partial or complete involution of the tonsils.

A very important aspect of the present invention is that the light is transmitted to the tonsil in an advantageous direction using the two opposing light-transmitting surfaces. This direction may most conveniently be anterior to posterior, although superior to inferior or any other direction in which light passes through the tonsil, from one tonsillar exterior mucosal surface to another other, rather than through the tonsil into underlying tissue, can be used according to the present invention. Consequently, the risk of heating or otherwise affecting the tonsillar bed and critical blood vessels and nerves under the tonsillar bed is minimal, and light is used most efficiently in treating the parenchymal cells of the tonsil.

It is recognized that model calculations involve simplifications and approximations of actual laser-tissue interactions, and results of the model calculations herein are estimates. In particular these model calculations do not take into account changes in tissue optical constants with temperature, or inhomogeneities in tissue optical or thermal properties. However, blood perfusion, which is normally a significant complicating factor in performing laser-tissue model calculations especially with relatively long irradiation times of tens of seconds or minutes, is of lesser importance as a consequence of tissue compression in the present invention.

In addition to controlling the heating of the tissue during irradiation, it is desirable to control the temperature of the tissue after irradiation is complete. If a tonsil is irradiated and heated while being compressed between two contact elements, as described above, and at the end of irradiation the tonsil is released, blood perfusion can be expected to be restored and the tonsil, in contact with air and adjacent tissues, will cool by a combination of conductive and convective processes. The time required for a tonsil to cool in this way will vary substantially due not only to differences in vascular supply but also in size. Large tonsils will cool more slowly than small tonsils, and tonsils with greater blood perfusion will cool faster than more poorly perfused tonsils. Heat diffusion from the interior of the tonsil can cause thermal injury to the tissue surface after irradiation is complete. Therefore, according to a preferred embodiment of the present invention, the tonsils will be held in compression with at least two cooled contact elements after irradiation is complete, to reduce post-irradiation tissue temperature. Specifically, according to an aspect of the preferred embodiment, the tonsil will be held with the cooled contact elements until substantially the entire tonsil is cooled to a temperature of approximately 50° C. or less. Controlled cooling of the irradiated tonsil parenchyma will limit the progression of thermal injury, produce a more predictable biological response, and minimize damage to the mucosal tissue surface layers. Controlled cooling of the irradiated tonsil parenchyma to a temperature between approximately 37° C. and approximately 5° C. will also minimize the risk of post-operative swelling and pain. Most preferably, according to the present invention, substantially the entire tonsil is cooled to a temperature below the normal physiologic temperature of 37° C. but not to a temperature that is so low as to cause irreversible cold injury, for example by freezing the tonsil parenchyma.

To summarize, it has been found that tonsils can be heated substantially over their full thickness when held and compressed between at least two light transmitting contact surfaces. Using an exemplary wavelength of 1120 nm, light emitted from each of the contact surfaces will produce temperatures in the tonsil corresponding to transitioning temperatures, within approximately 30 seconds to approximately 10 minutes, depending on the size of the tonsil and the power used. With power of 8 W from each light-transmitting contact surface, a very large tonsil can be heated to temperature of approximately 60° C. in only 4 min. This time/temperature combination is expected to be effective in treating the tonsil, based on the vital stain experiments described in the previous section. A tonsil of average size for tonsillectomy can be heated to a temperature of about 65° C. in 3 min using a power of 7.5 W, or in less than 2 min using 10 W. These irradiation times are short compared to time required to excise a tonsil in tonsillectomy procedures, and are therefore a highly advantageous aspect of the invention. The tonsil mucosal surface can be protected from thermal injury by moderate cooling of the light transmitting contact elements. Tonsils of various tissue composition and size can be heated symmetrically over the entire thickness. Post-irradiation cooling of the tonsils using the contact surfaces can provide further control of the tissue temperature, limit thermal injury, and further reduce post-operative pain and swelling.

It may be appreciated that while model calculations have as their output the temperature at any point within the irradiated tissue, at any time during or after irradiation, in actual photothermal treatment of tonsils it is advantageous to use a sensor or measurement device to follow or monitor the tissue temperature as a function of time. Therefore when treating tonsils according to the invention it is preferable to measure the temperature of tissue in at least one location within the tonsil during and after photothermal treatment. Preferably, the temperature is monitored and irradiation is continued until a target temperature is reached in at least one location within the tonsil parenchyma. Most preferably, temperature is measured in at least one location within the tonsil parenchyma, and in at least one location in, on, or adjacent the tonsil mucosa. Most preferably, the temperature in at least one location in the tonsil parenchyma is monitored during irradiation until a target temperature is reached in the parenchyma, and the temperature in at least one location on or in the tonsil mucosa is monitored during irradiation to ensure that the mucosal temperature does not increase above approximately 50° C. during irradiation. Most preferably, the contact surface actively cools the tonsil after irradiation is complete, and the temperature in at least one location in the tonsil parenchyma is monitored to ensure that post-irradiation cooling is sufficient to reduce the parenchymal temperature to less than approximately 37° C.

It is recognized that for very small tonsils, or if multiple sequential treatments are performed, heating of the tonsil using a single light-transmitting surface may be used. The tonsil may be held between two opposing surfaces, only one of which is light-transmitting. In that case, as in the case of using two opposing light-transmitting surfaces described in detail above, the light is transmitted to the tonsil in an advantageously anterior to posterior direction, through only the tonsil, such that the risk of heating the tonsillar bed and critical blood vessels and nerves under the tonsillar bed is minimal. The non-transmitting surface may be cooled, and it may be reflective of the wavelength or wavelengths transmitted by the opposing surface. Another alternative is to use two light-transmitting surfaces, and alternate their activation during treatment. Yet another alternative is to use a single light-transmitting surface, and reverse the orientation of the handpiece to irradiate opposing sides of the tonsil. Those approaches are less advantageous because of the additional procedural time requirements. Alternatively, the tonsil may be irradiated using a single light-transmitting surface in contact with the medial surface of the tonsil. Such treatment is not preferred, since light is directed through the tonsil and into the tonsillar bed.

According to an aspect of the present invention, the tonsils are held between at least two contact surfaces. At least two regions of the tonsil surface adjacent to said contact surfaces are substantially flattened, and the maximum thickness of the tonsil tissue between said contact elements is reduced, compared to the tissue of a tonsil in its normal position within the oropharynx. When the tonsil is held between said contact surfaces and light is transmitted from at least one of said surfaces the tonsil can be heated more evenly because of its flattened, more uniform shape and reduced thickness. In one embodiment of the invention, the tonsil is held between at least two contact surfaces with sufficient applied pressure to reduce the perfusion of blood in the tonsil tissue, during the time that light is being applied to the tonsils. Applied pressure will reduce both the volume of blood and the flow of blood within the tonsils, to mitigate the effects of tonsil vascularity on photothermal treatment. In an aspect of the embodiment, the pressure is sufficient to reduce the perfusion of blood but not great enough to cause substantial cell rupture or other mechanical damage or trauma to the tonsil tissue.

As previously described, the effects of tonsil vascularity can be substantially reduced by selection of wavelength within the about 1100 nm to about 1350 nm range.

In one embodiment of the invention, both said range of wavelength and pressure application reduce the effects of tonsil vascularity and blood perfusion.

Description of Apparatus

In one aspect, the invention is directed to an apparatus for treatment of soft tissue. In one embodiment, the apparatus includes a light source and at least two optical assemblies. Each of the at least two optical assemblies include at least one optical element and a light-transmitting contact surface. The light transmitting contact surface is configured to transmit a substantially uniform distribution of light therethrough. The apparatus further includes at least two optical transmission devices each disposed between the light source and a corresponding one of the at least two optical assemblies. The apparatus still further comprises a handpiece to which the at least two optical assemblies are attached. The handpiece is adapted to bring the light-transmitting contact surfaces of the at least two optical assemblies in contact with soft tissue disposed therebetween. The optical assemblies of the apparatus each may also include a housing to contain and protect the optical elements.

Figure 13:
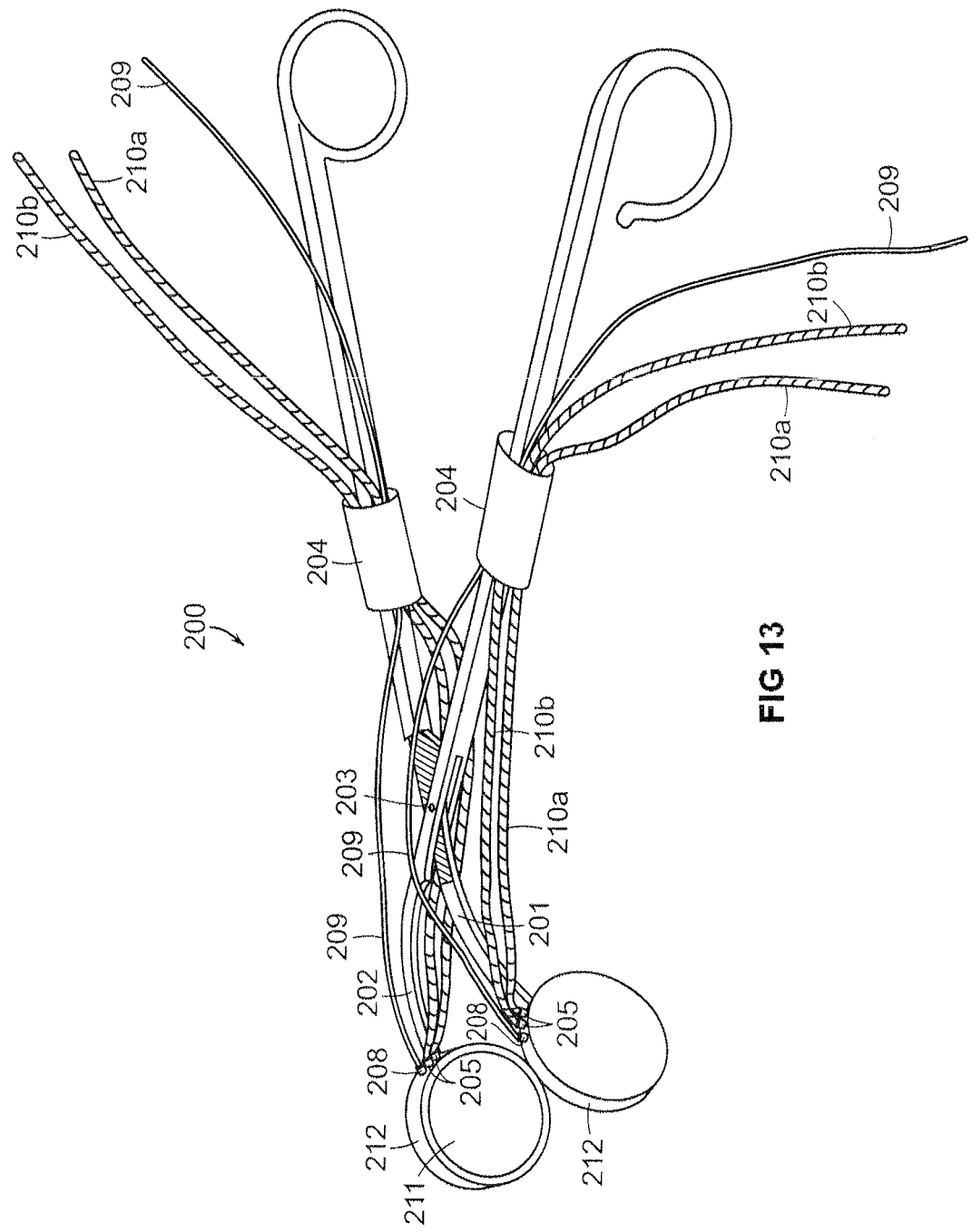
FIG. 13 is a semi-schematic drawing of a handpiece of the invention with attached optical assemblies.

FIG. 13 is a schematic depiction of a very simple embodiment of the present invention. Shown is a handpiece 200, having first distal portion 201 and second distal portion 202 attached at a pivot point 203. Handpiece distal portions 201 and/or 202 may be curved or straight, and of any size, diameter, or length that is convenient for accessing the tonsils within the confines of the oropharynx. Distal portions 201 and 202 move relative to each other about the pivot point 203 to increase or decrease the distance between the light-transmitting contact surfaces 211, and to bring said light-transmitting surfaces into contact with tissue disposed between said surfaces. Attached to the distal end of each of the two distal portions 201 and 202 of the handpiece are optical assemblies, each having housings 212 that at least partially contain and protect at least one optical element. Light-transmitting contact surface 211 is a surface of the optical assembly. Housings 212 are connected to the handpiece distal portions 201 and 202. The housings 212 have connections 208 to the distal ends of flexible optical fibers 209, and connections 205 to distal ends of inlet coolant lines 210a and outlet coolant lines 210b. Coolant lines 210a and 210b are flexible tubes. Proximal ends of lines 210a and 210b are connected to a cooling device (not shown), which provides coolant fluid to the optical assemblies. The proximal ends of optical fibers 209 are connected to a light source (not shown). According to the invention, the light-transmitting contact surfaces 211 are made of a biocompatible material that is substantially transparent to light of the wavelength or wavelengths transmitted from the light source through the optical fiber. In one embodiment, the contact elements are made of a material with high thermal conductivity and/or large heat transfer coefficient. The light-transmitting contact surfaces 211 may be substantially flat as shown in this figure, may have multiple flat surface segments arranged with angles relative to one another, or may have curvature over all or part of their area. The angles or curvature may give the contact surfaces a concave shape. In other embodiment, the contact surface may have a flat central region with a curvature on one or more edges to facilitate holding or retracting the tonsils. The coolant fluid transported by lines 210a and 210b is in thermal contact with the light-transmitting surfaces 211.

It may be appreciated that the handpiece 200 may have many different styles and configurations, such that its manual manipulation allows the optical assemblies to be positioned within the oropharynx and positioned relative to each other and to the tonsil. The handpiece 200 is any handheld device that allows a user to bring light-transmitting surfaces 211 into contact with a tonsil. In some embodiments one light-transmitting surface will remain in a fixed position in the handpiece and the other light-transmitting surface will be movable. In other embodiments both surfaces may be moved separately and in relation to the other. The handpiece 200 may be used to grasp the tonsil and retract it in a medial direction away from the tonsillar bed and away from the wall of the oropharynx, while applying gentle pressure with the light-transmitting contact surfaces 211. Alternatively, or in some instances, a forceps, tenaculum, or any grasping or retracting instrument may be used to first retract the tonsil in a medial direction before the handpiece 200 is used to contact said tonsil. In such instances, after the handpiece of the invention has been brought into contact with the tonsil, the tenaculum or other standard instrument may be disengaged from said tonsil and removed, prior to activation of the light source or cooling device.

For accessing the tonsils, the handpiece should be configured so that housings 212 can be positioned in the space adjacent the mucosal surface of the tonsil. When the tonsil is in its normal, unretracted position in the oropharynx, the anterior and posterior tonsillar pillars (glossopalatine muscle and pharyngopalatine muscle, respectively) are adjacent to the tonsil. Therefore it is advantageous for the housings 212 attached to the distal portions of the handpiece to be sufficiently thin that said housings can be inserted between the mucosal surface of the tonsil and the adjacent anterior and posterior pillars, so that a substantial portion of the parenchymal tissue of the tonsils is disposed between the two light-transmitting contact surfaces 211 when the tonsil is held and irradiated between said surfaces. The opposing light-transmitting surfaces 211 are positioned so that during irradiation of the tonsil, light passes through the tonsil parenchyma. Light may be passed in, for example, a substantially anterior (in relation to anterior pillar) to posterior (in relation to posterior pillar) direction, or, for example, in a substantially inferior (in relation to base of tongue) to superior (in relation to soft palate) direction using surfaces 211. In all embodiments of the invention, the handpiece is configured to pass light through across the tonsil t, and to not substantially transmit light through the tonsil tissue towards the wall of the oropharynx. The thickness of housing 212, which contains at least one optical element, one surface of which is the light-transmitting contact surface, is defined as the maximum thickness perpendicular to the light-transmitting contact surface, from the light-transmitting contact surface 211 to the outer surface of the housing 212. Said thickness is sufficiently small that a substantial portion of the tonsil parenchyma can be disposed between light-transmitting surfaces 211 when the tonsil is held by said light-transmitting contact surfaces of the optical assemblies. For example, the thickness is small enough that the housing can be positioned adjacent to the tonsil such that a lateral edge of said housing is adjacent to or in proximity to the wall of the oropharynx, when the tonsil is in contact with the light-transmitting contact surface. Or, for example, the thickness may be approximately 6 mm or less. Also, for example, about 20 to 100 percent of the volume of the tonsil parenchyma should be directly between the opposing contact surfaces, and no more than about 80 percent of the parenchyma should extend outside of the region directly between the contact surfaces. In one embodiment, said thickness is sufficiently small that substantially all of the tonsil parenchyma can be disposed between light-transmitting surfaces 211 when the tonsil is held by said light-transmitting contact surfaces of the optical assemblies. Preferably, about 50 to 100 percent of the volume of the tonsil parenchyma should be directly between the opposing contact surfaces, and no more than about 50 percent of the parenchyma should extend outside of the region directly between the contact surfaces. Most preferably, about 75 to 100 percent of the volume of the tonsil parenchyma should be directly between the opposing contact surfaces, and no more than about 25 percent of the parenchyma should extend outside of the region directly between the contact surfaces. In one embodiment, said thickness is less than about 6 mm.

The surface area of each of the light-transmitting contact surfaces 211 is sufficiently large that said light transmitted from said surfaces irradiates a substantial portion of a tonsil gently compressed between the surfaces. For example, about 20 to 100 percent of the tonsil should be directly between the opposing contact surfaces, and no more than about 80 percent of the tonsil should extend outside of the region directly between the contact surfaces. For example, the surface area of each of the light-transmitting surfaces is at least about 20 mm$^3$ and up to about 1250 mm$^3$. In one embodiment, the surface area of each of the light-transmitting surfaces is between about 100 mm$^3$ and 1250 mm$^3$. The contact surface may be circular, oval, elongated, or any other geometric or nongeometric shape.

Figure 14:
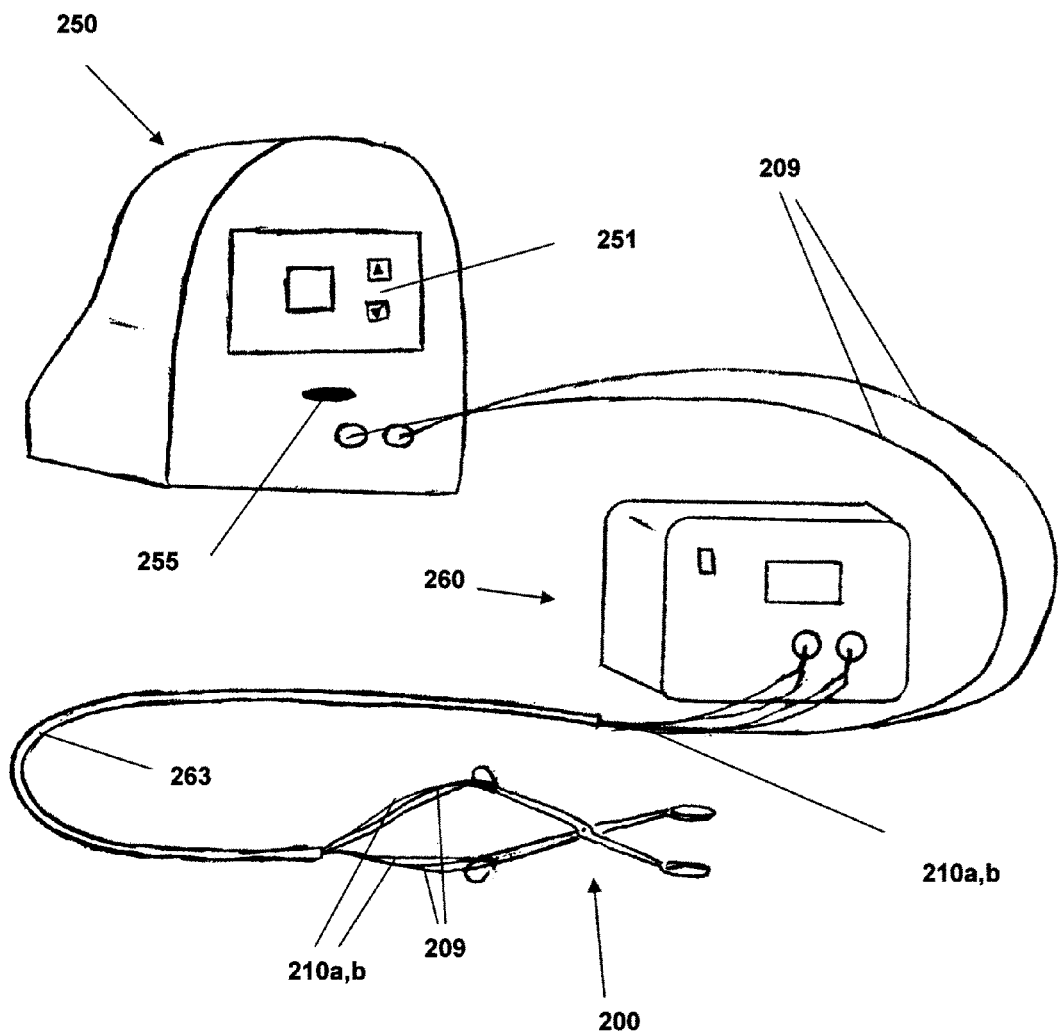
FIG. 14 is a depiction of an apparatus of the invention.

The proximal ends of the optical transmission elements are connected to a light source. In one embodiment, the handpiece comprises coolant lines that are connected at their proximal ends to a cooling device. The cooling device may be, for example, a recirculating chiller or a device that produces a flow of chilled air. The lights source comprises control and power electronics, switches, user interface and display, and may include a calibration port for measuring the light output of the optical assemblies. An apparatus of the invention may comprise a light source, at least one transmission optical transmission device, and a handpiece. A very simple embodiment of an apparatus of the invention is depicted schematically in FIG. 14. A light source 250 is connected by optical fibers 209 to a handpiece 200. The light source 250 comprises a user interface display 251 and a calibration port 255. A cooling device 260 is connected to the handpiece 200 by coolant lines 210a and 210b. The coolant lines and the optical fibers may be contained within an umbilical cord 263 over a portion of their length. In embodiments of the invention which comprise a cooling device, the cooling device and the light source may be combined in a single unit, or may be separate devices.

According to an embodiment of the invention, a cooling device 260 connected to the handpiece 200 is activated and cooling fluid with temperature of no more than about 37° C. is circulated within the housings 212 of the optical assemblies, such that the fluid is in thermal contact with the light-transmitting contact surface 211 of the at least one optical element of the housing. Before, during or after activation of the cooling device, the handpiece is manipulated to bring the light-transmitting surfaces into contact with a tonsil, for example, with gentle compression of the tonsil between said surfaces. The light source is then activated to irradiate the tonsil. After irradiation is complete, the handpiece may be manipulated to remove the light-transmitting surfaces from contact with the tissue. In an advantageous embodiment, there is a delay between the completion of irradiation and removal of the contact surfaces from the tonsils, during which time the tonsils are substantially cooled by contact with said surfaces to a physiologic temperature or below. The temperature of the cooling fluid transmitted by the cooling device may be further reduced to a temperature not less than about 3° C. after the irradiation is complete and until the tonsils are substantially cooled. For example, the tonsils may be cooled until they reach 37° C. Or, for example, the tonsils may be cooled until they reach 10° C.

Figure 15:
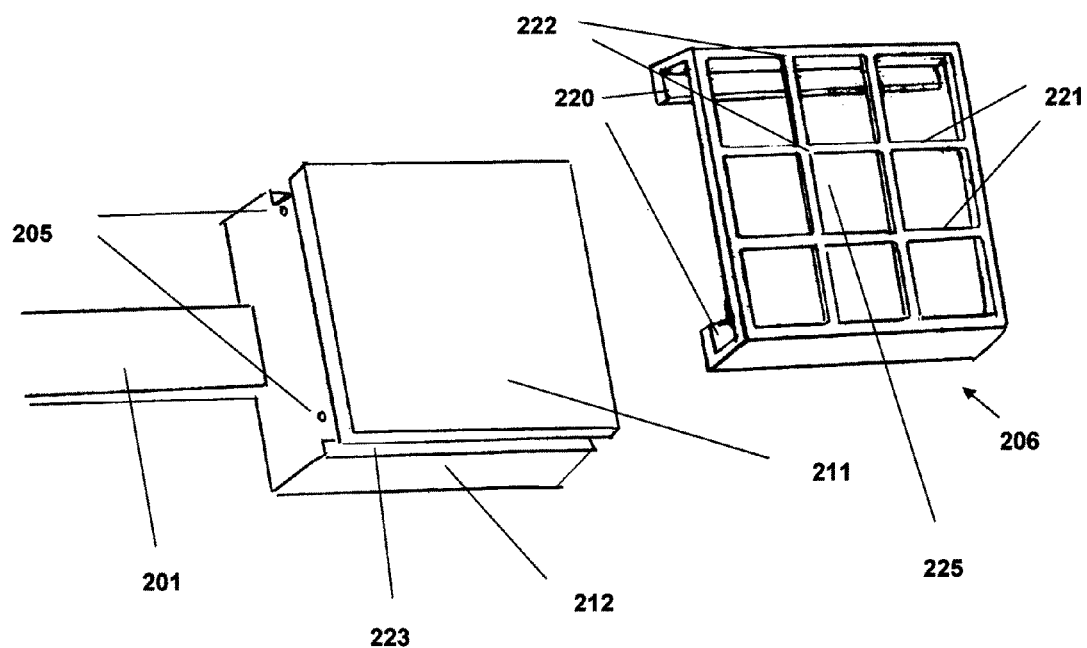
FIG. 15 is a depiction of a handpiece distal portion with optical assembly, and a grid element.

In one embodiment, disposable elements are attachable to the apparatus of the invention These disposable elements may be grid elements 206 attachable to the optical assemblies via attachment to the housings or contact surfaces. Alternatively, the disposable element may be attachable to the handpiece via a disposable sleeve, which will be described later in further detail. A grid element is shown in FIG. 15. The grid elements are a solid or open component that may be attached and detached from the housings 212 or contact surfaces 211, for example by sliding in and out of a groove 223 on the housing 212. In one embodiment, the grid element has open areas 225, such that when tonsil tissue is held by the handpiece, said tissue is touching the light-transmitting contact surfaces within the open areas of the grid. The grid element may include grid sections in the form of spline sections 221 that meet at intersecting sections 222. As will be obvious, many other designs and patterns may be used for the shape of the spline sections, intersecting sections, and open areas of the grid. For example the grid may be a plate-shaped element with holes of constant or various sizes, placed at regular or irregular intervals. If the grid element is attached by sliding into a groove 223 on the housing, it may have an angled edge 220 as shown in FIG. 15. Other means of attachment to the contact elements may include press fitting and snap fitting, with attachment points located on the housing, on the contact surface, or both. Although in FIGS. 15 and 16 the grid element depicted is composed of straight or planar sections, in other embodiments of the invention all or part of the grid element has a shape that conforms to a non-planar light-transmitting contact surface of the optical assembly, for example, a portion of a grid that comes in contact with a curved contact surface may be curved.

Figure 16:
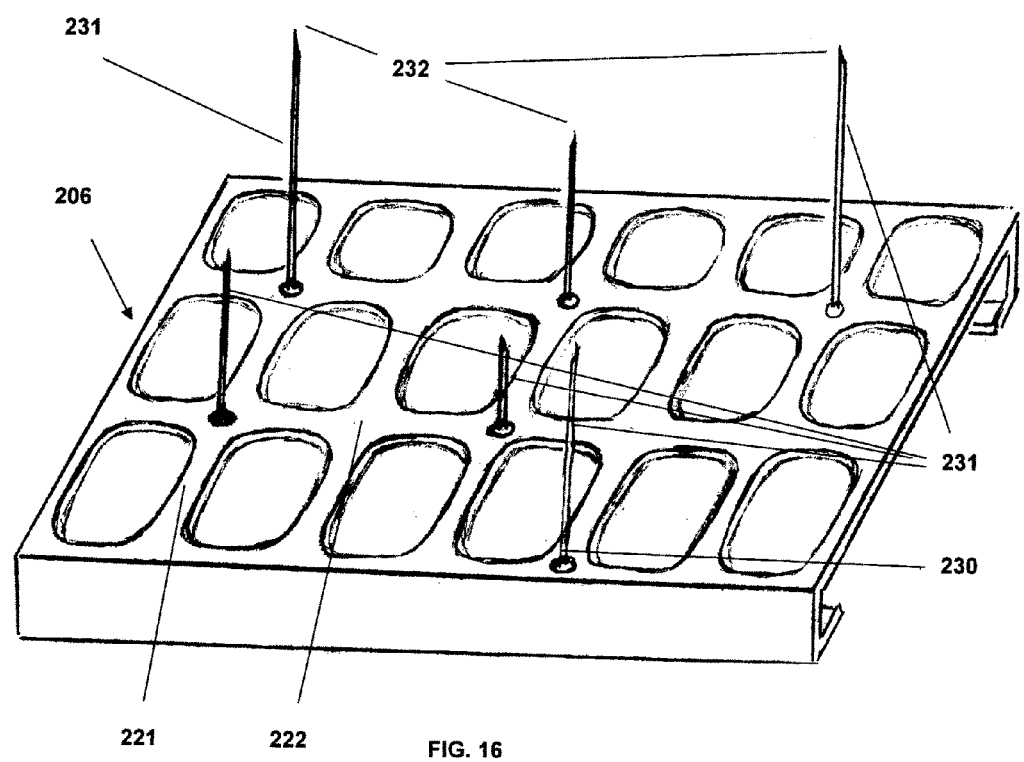
FIG. 16 is a depiction of a grid element with attached sensor needles.

FIG. 16 depicts a grid element 206 to which multiple temperature sensors housed in sensor needles 231 may be attached. The sensor needles have distal tips 232 that are pointed, beveled, or angled so as to penetrate the tonsil with minimal tissue trauma. The proximal ends 230 of the sensor needles 231 are inserted in the grid element, for example by press fitting into holes in the grid elements and/or by use of a biocompatible epoxy or other adhesive. The lengths of the sensor needles are about 1.5 cm or less. In one embodiment, when multiple sensor needles are attached to the grid, individual needles have different length in order to sense the temperature at different depths within the tonsil tissue. In an aspect of the embodiment, one or more grid elements with at least one affixed temperature sensor may be attached to the handpiece distal portions prior to a tonsil treatment procedure, and detached after the procedure is completed. In this aspect of the embodiment, the grid elements with sensor needles are disposable. In an aspect of the embodiment, the grid elements with affixed sensors are packaged before the procedure in a sterile or sterilizable container.

According to the present invention, the grid element serves as a novel mechanism for placing temperature sensors at fixed locations in the tissue relative to the optical components of the optical assemblies including the light-transmitting contact surface, while also allowing said sensors to be an element of a detachable and/or disposable component of the device. The design of the grid element allows substantially all or most of the light emitted from a contact element to reach the surface of a tonsil through the open areas of the grid and, if the grid is made of a material that is transparent or partially transparent, also through the grid sections.

In the absence of attached needles, the grid element also may serve to enhance the gripping action of a contact surface, either by the irregularities of the open areas within the grid sections, or by a surface treatment of the grid element to provide roughness or surface texture.

In some embodiments, to be discussed in further detail below, a grid element may advantageously modify the optical output of a device of the invention.

In one embodiment, the grid element is made of a plastic material that substantially transmits light of the wavelength or wavelengths emitted by the light source of the apparatus. In a specific embodiment, the grid element is made of polyetherimide resin, e.g. Ultem® (SABIC Innovative Plastics). In another specific embodiment, the grid element is made of a polycarbonate resin, e.g. Makrolon® (Bayer Material Science). The portion of the tonsil tissue surface touching the light-transmitting contact surface within the open areas of the grid can be directly cooled by said contact surface, and the portion of tonsil tissue surface touching a portion of the grid element can be cooled by contact with said grid element which in turn is in contact with the light-transmitting contact element and/or by heat transfer from adjacent tonsil tissue directly cooled by the contact surface. Thus, the grid element of the invention provides for the insertion of one or more temperature sensors at predefined distances in the tissue from the light-transmitting contact surfaces of the optical assemblies and/or at predefined locations in the tissue relative to said surfaces, by a means that does not interfere substantially with either delivery of light to the tissue or to the effective cooling of the tissue. In FIG. 16 the attached needles are depicted as extending in a direction perpendicular to the contact surface, an arrangement that allows the needles to be inserted as the contact surfaces are brought into contact with and gently compress the tonsils. Alternative embodiments of a grid element can be envisioned, for example, the needles may have a U-shaped proximal end, and attach at said proximal end to channels located on a portion of a grid element that is at a lateral location on the attached optical assembly. The long axis of the needle is parallel to the contact surface, and by pushing or otherwise moving the needle at its U-shaped bend so that it inserts into the channel, after the tonsil is grasped by the contact surfaces, the needle is inserted into the tonsil tissue from a lateral direction.

The grid element may be attachable to the optical assembly such that the grid element is in contact with and/or adjacent to one of the light-transmitting contact surfaces, and the grid element is adapted to be brought into contact with soft tissue disposed between the optical assemblies. The grid element with affixed sensors can be attached to the housing and/or contact surface of the optical assemblies before the procedure and detached after the procedure, for disposal. It is advantageous to separate the optical assembly with its at least one optical component from the affixed sensor needles or other components for which reuse in patients is impractical. Said optical components are expensive and may require precise relative alignment. According to the present invention, optical components of the optical assemblies can be kept substantially intact and reused, while the grid elements with needles that are inserted in the tissue can be disposed of after use so that the procedure is convenient, practical, and economically advantageous.

Figure 17:
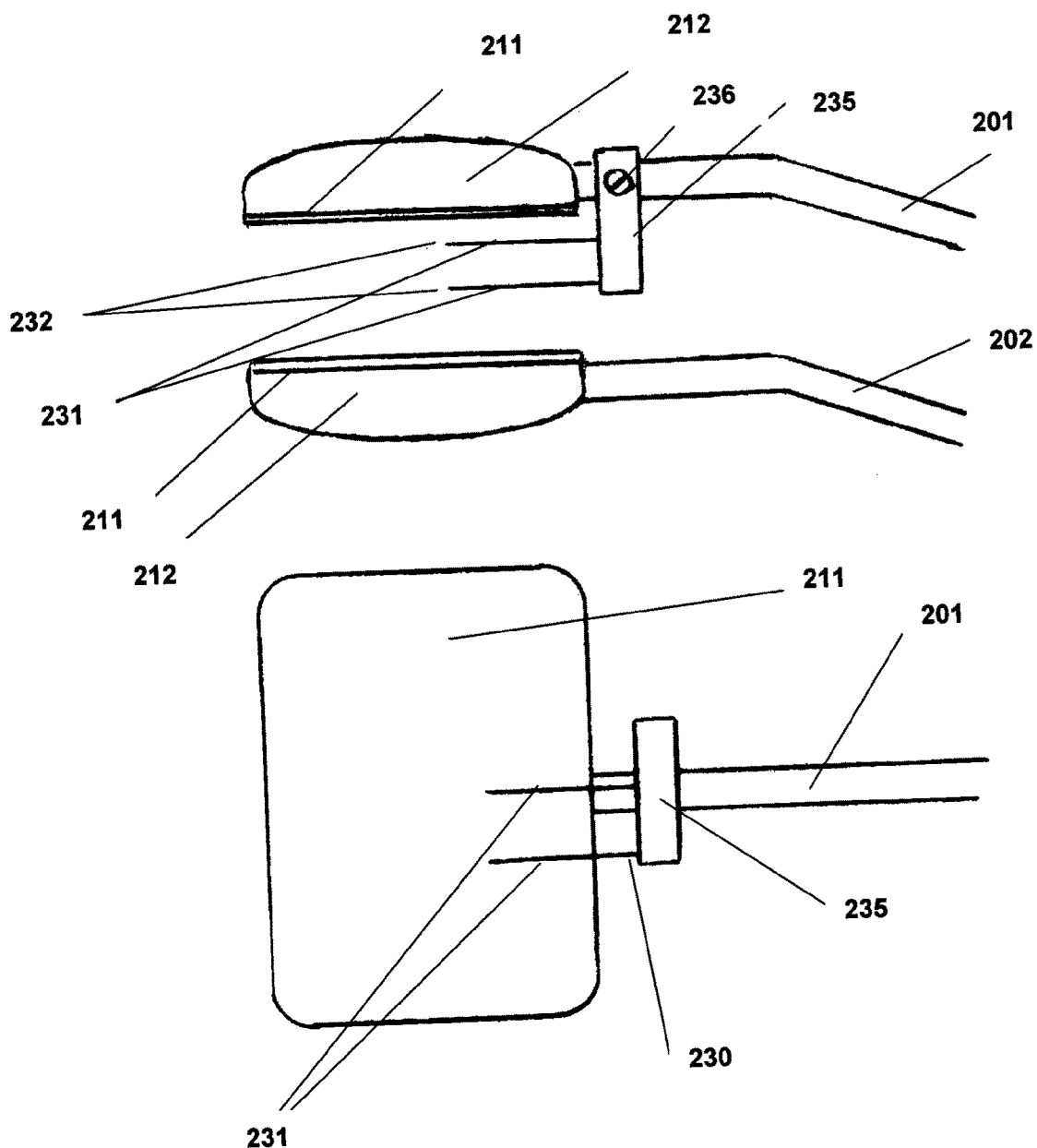
FIG. 17 is a depiction of a handpiece distal portion with attached optical assembly and attached collar element with sensor needles.

Alternatively, the disposable elements may be collar elements, for attachment to at least one of the handpiece distal portions 201 and 202, as shown in FIGS. 17A and 17B. In this embodiment, at least one sensor needle 231 is attached to a collar element 235 that is attached to the distal portion of the handpiece such that the sensor need can be brought into contact with soft tissue disposed between the optical assemblies of the apparatus by, for example, moving the collar relative to the handpiece. The collar element of the example of FIG. 17 is movable on the distal portion of the handpiece until tightened by a set screw 236. Sensor needles 231 are positioned with their long axis substantially parallel to the direction of collar movement. As can be seen in FIG. 17A, the distance between a sensor needle distal tip 232 and the light-transmitting surface 211 is constant as the collar slides, and is determined by the size of the collar element and the attachment point of the needle proximal end 230 to the collar. As can be seen in FIG. 17B, the length of a needle 231 and the position of the collar 235 will determine the location of the needle distal tip 232 in tissue held between two light-transmitting surfaces 211. The collar element is adaptable for use with optical assemblies having flat or curve surfaces. The collar may be made of any biocompatible plastic or metal material. In one embodiment, the collar is made of a biocompatible laser-resistant moldable or machinable material, such as Ultem. The collar element and the grid element are both alternative means for providing temperature measurements at known locations or depths within the tonsil tissue before, during, and after irradiation. The collar and the grid element are adapted for attachment to the handpiece and the optical assembly of the invention, respectively.

A temperature sensor that is suitable for use in a sensor needle according to the present invention includes a thermocouple or a thermistor. Thermocouples housed in small diameter hypodermic needles are commercially available. Type T thermocouples are available in stainless steel hypodermic needle probes as small as 200 micron diameter from a commercial source (HYPO Mini-Hypodermic probe, Omega Engineering). Other examples of a temperature sensor in a stainless steel needle is the MLT1406 Needle Microbe Thermocouple (ADInstruments), and the MT-23 635 micron diameter needle probe (Physitemp Instruments, Clifton, N.J.). The time constant of such needle probes is on the order of 0.1 s, making them suitable for temperature monitoring and control. In the present invention, sensor needles are of a diameter about 200 microns to about 700 microns. In one embodiment, the sensor needle diameter is about 200 microns to about 500 microns. In one embodiment of present invention, the sensor needles are made of medical grade stainless steel (316, 316L or vacuum melted type 316L). In another embodiment, the sensor needles are made of medical grade titanium (unalloyed commercially pure CP grades 1-4) or titanium alloys (including Ti-6Al-4V ELI, Ti-6Al-4V, Ti-6Al-7Nb, Ti-3Al-2.5V, Ti-13Nb-13Zr, Ti-12Mo-6Zr-2Fe, Ti-15Mo) Other metallic materials that can be used to make the sensor needles include silver, platinum, tantalum, niobium, zirconium and zirconium alloys, shape memory alloys based on the nickel-titanium binary system, tungsten and tungsten bronzes, and cobalt alloys (Elgiloy and MP35N). Needle probes made of many metallic materials, including stainless steel, will absorb light including NIR light of the range of about 1100 nm to 1350 nm to be directly heated. Therefore, in one embodiment, the needle is made of a metal that substantially reflects NIR light, and in another embodiment, made of gold, which is highly reflective of NIR light. In another embodiment, a coating that substantially reflects NIR light is applied to the exterior surface or exterior and interior surface of a sensor needle. For example, a gold coating is applied to the surface of the sensor needle. Use of a gold needle or a gold-coated needle will reduce measurement artifacts due to direct absorption of light by the sensor needle, and will allow the tissue temperature to be measured simultaneously with tissue irradiation, for the most precise and rapid control of the irradiation process. In the absence of a reflective coating, the irradiation process can be intermittently halted to measure temperature after the needle probe equilibrates with the surrounding tissue. Halting the irradiation will allow accurate temperature measurements to be made with, for example, a standard stainless steel needle probe, although the total treatment time will be slightly longer as a result. Alternatively, according to the present invention, accurate temperature measurements may be made with a probe made of stainless steel or other material that absorbs light, if the signal is processed to separate out the exponential artifact signal.

The grid sections of grid elements provide structures for containing and routing lead wires of the temperature sensors of the sensor needles away from the optical assembly and the handpiece. These structures may be closed or open channels or grooves in the spline sections and intersections of the grid sections. Preferably, these channels or grooves are coated with or comprise a substantially reflecting material to prevent absorption of light by the lead wires. Alternatively, the lead wires themselves may be coated or shielded with a reflecting material.

Figure 18:
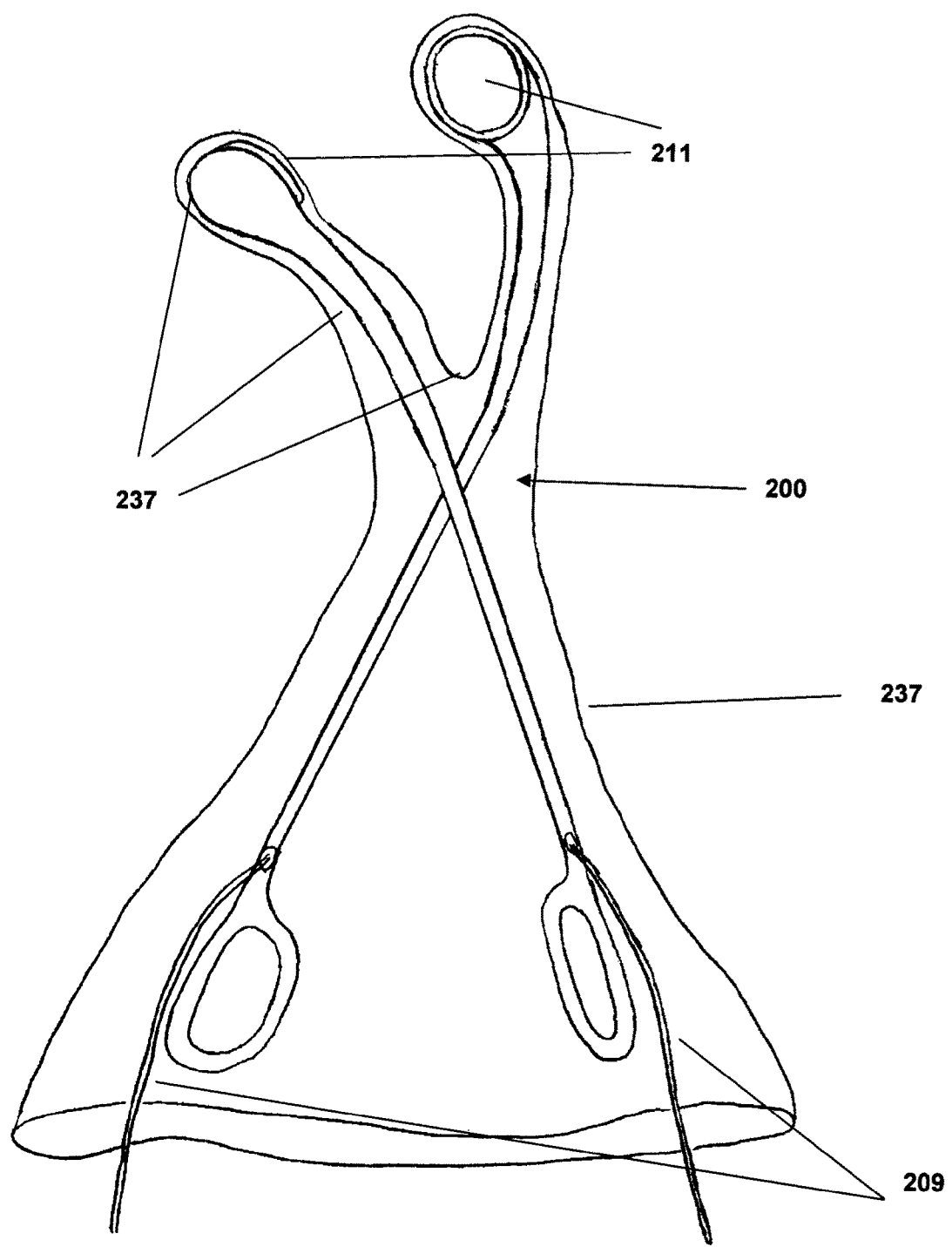
FIG. 18 is a depiction of a handpiece with attached optical assemblies and covered with a disposable sleeve.
Figure 19A:
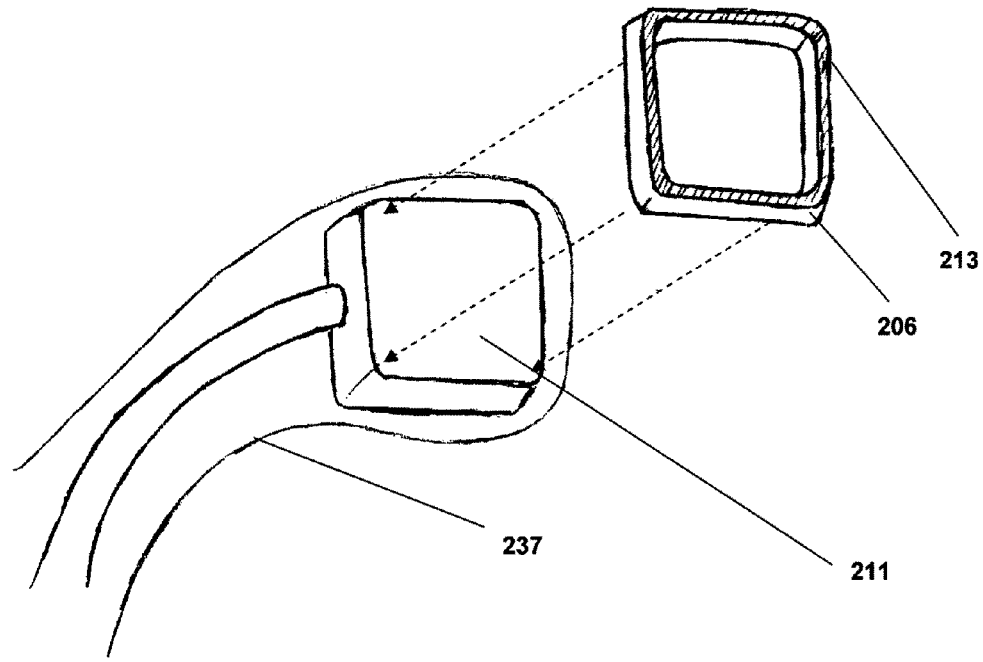
FIGS. 19A and B depict a handpiece distal portion with attached optical assembly covered with a disposable sleeve, and a grid element that attaches to the optical assembly.
Figure 19B:
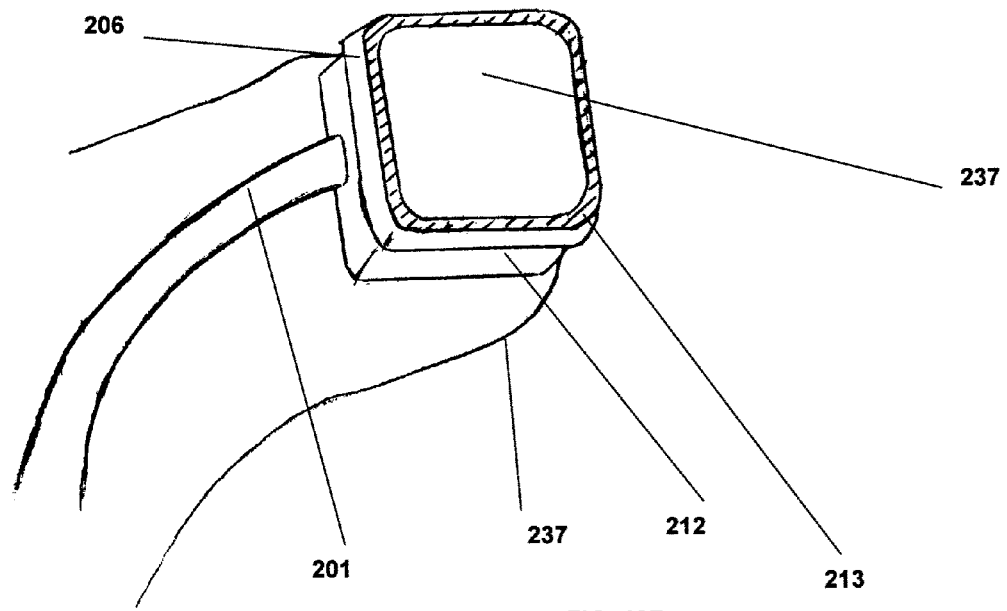

In some embodiments of the invention, the handpiece is autoclavable. In one embodiment of the invention, the handpiece is covered with a sterile disposable sleeve prior to use, as depicted in FIG. 18. Said sleeve 237 comprises a flexible polymeric material. Sleeve 237 may be made substantially entirely of polymeric material with substantial transparency to the wavelength or wavelengths of the light source of the apparatus. For example the sleeve may have 75% transmission, or 90% transmission. More advantageously, the sleeve has a transmission of over 90%. Or, Sleeve 237 may comprise non-transparent flexible polymeric material and substantially transparent window portions that are adapted to be aligned with and to come in contact with the light-transmitting contact surfaces 211 of the optical assemblies. The substantially transparent window portions of the sleeve 237 may be flexible transparent plastic, such as but not limited to polyethylene, polyimide, polyurethane, latex, polyolefin, fluorocarbon polymer, or the window areas may be rigid or semi-rigid plastic, such but not limited to as acrylic, polyvinyl chloride, or polycarbonate. In one embodiment, the substantially transparent window portions of the sterile disposable sleeve are made of a rigid or semirigid transparent polymeric material such as acrylic or polycarbonate that is not substantially thicker than is necessary to provide mechanical strength and sterile protection. The sleeve 237 may have a bifurcated shape with distal ends to cover the handpiece distal ends, and a loose proximal portion adapted to allow the handpiece to be manipulated.

For a flexible sleeve made of a particular polymeric material, that portion of the sleeve that covers the light-transmitting contact surfaces may be as thin as necessary for adequate strength and maintenance of its barrier function, for that particular material. Transmission may be enhanced advantageously by the use of thinner sleeves. Notably, effective cooling of the tissue from a cooled light transmitting contact surface is achieved through a flexible disposable sterile sleeve of thicknesses commonly employed in medical devices.

In one embodiment, a grid element 206 is attached to the housing or contact surface after a sterile sleeve 237 has been placed over the handpiece. An aspect of this embodiment is that the attachment of the grid fixes the position of a substantially transparent area of a sterile sleeve over the light transmitting contact surface 211 of the optical assembly. The grid element is attachable to the handpiece such that the grid element is in contact with a window portion of the disposable sleeve covering the light-transmitting contact surface 211 and such that the grid element is brought in contact with soft tissue disposed between the optical assemblies. A grid element 206 may be attached to a housing or contact surface over a sterile sleeve by press fitting or snapping, for example.

In one embodiment, a grid element 206 with or without needles is preattached to the sterile sleeve 237 and the sterile sleeve is adapted to cover at least the distal ends of the handpiece so that the preattached grid element is in contact with the disposable sleeve before it is attached to the optical assembly. In another embodiment, a grid element 206 is pre-attached to the sterile sleeve at a transparent window portion of the disposable sleeve. In some embodiments, a grid element is permanently attached to the sterile sleeve. In such embodiments, a sleeve with at least one grid element permanently attached or preattached is placed over the distal portions of the handpiece and the grid element is press fitted or snap fitted, for example, onto the housing or contact surface.

In some embodiments where the disposable element is a collar, the collar may be attachable to the handpiece distal portion after the distal portion is covered by the sterile sleeve. The collar may also be preattached or permanently attached to the disposable sleeve.

Light sources to implement the present invention are available. Considering first the most wavelength region of about 1100 nm to 1350 nm, choices of laser technologies that can produce multiwatt output include the ytterbium-doped fiber laser, and the quantum dot semiconductor laser. Ytterbium fiber lasers producing multi-kilowatt powers have been introduced for use in materials working and automobile manufacturing, and lower-power models suitable for the present application are commercially available. For example, IPG Photonics (Oxford, Mass.) produces a benchtop 20 W air-cooled Yb fiber with a 3 meter delivery cable, center wavelength 1120 nm, bandwidth 2 nm (fwhm), and visible aiming beam. The system can be operated in CW mode or with externally controlled pump modulation. Because fiber lasers have a broad gain bandwidth there is the possibility of developing a medical laser that operates over multiple wavelengths or is tunable, for example within the wavelengths of 1050 nm to 1120 nm in the case of Yb-doped fiber lasers, such that the laser could be operated at 1120 nm for the present tonsils application, or at 1064 nm for applications that the Nd:YAG laser is commonly used in otolaryngology and other medical fields. With frequency doubling of polarized output from a Yb fiber laser, 532 nm operation is possible such that the device could also be used for KTP laser applications for a highly versatile medical system.

Wavelengths shorter than 1100 nm, and longer than about 1280 nm can be obtained using GaAs and InP diode lasers, respectively, but until recently the intervening region was not readily available from a diode source. In the past few years, however, efficient, high power semiconductor lasers based on quantum dot (QD) nanotechnology have been developed. QD lasers have advantages of enhanced gain for low operating current, high spectral purity (very narrow bandwidth), and minimal temperature effects. Innolume, Inc. (Santa Clara, Calif. and Dortmund, Germany) has recently commercialized QD lasers based on InAs quantum dots in GaAs with AlGaAs barriers, all on GaAs substrates. Fiber coupled quantum dot laser modules from this source producing 30 W at a center wavelength of 1120 with bandwidth 3 nm fwhm are available.

In addition to lasers, incoherent light sources may be used. One such incoherent source is the tungsten halogen lamp. Because the halogen lamp has a broad emission in the visible and NIR, filters should be used to block the emission of light outside the 700 nm to 1350 nm range, or more preferably outside the 1100 nm to 1350 nm range. In addition, superluminescent diodes emitting in the 1100 nm to 1350 nm range have been demonstrated and may be used.

Although it is outside the wavelength range of about 1100 nm to 1350 nm, the neodymium YAG laser operating at 1064 nm has a long history of medical use and may be used according to the invention. As described above it is desirable to limit the effect of tonsil vascularity by both compression of the tonsil by the light transmitting contact surfaces of the optical assemblies and by the use of wavelengths that are less well absorbed by blood (about 1100 nm to 1350 nm), however compression alone by contact irradiation using the handpiece of the invention may suffice to reduce the effect of blood and may allow wavelengths in the about 800 nm to 1100 nm range to be used. The 1064 nm YAG laser readily produces output powers in the range that would be necessary for it to be used as the light source in the current invention, and it is a reliable and relatively inexpensive laser well suited to fiber optic delivery. Similarly, high power diode lasers at NIR wavelengths of 810 nm, 940 nm, 980 nm and other wavelengths between 700 nm and 1100 nm are readily available, of relatively low cost, and are familiar light sources for medical and surgical applications that may also be used according to the present invention.

The light source of the invention is connected to an optical transmission element. The optical transmission element is substantially flexible, and may be an optical fiber, optical fiber bundle, or light guide. A single optical fiber may be connected to a light source, and the distal end of said fiber connected to a fiberoptic beamsplitter to two other optical fibers, which are in turn connected to the handpiece of the invention.

An important aspect of the present invention is that the handpiece is configured so that a tonsil can be disposed between the two contact surfaces of the handpiece. Accessing the oropharynx and space adjacent to the tonsil is facilitated by making handpiece distal ends and, particularly, all elements attached to the handpiece distal end including housing and optical components, thin enough to be manipulated and inserted within said space. It is most advantageous if all such elements are about 6 mm or less in thickness. At the same time, for advantageously rapid phototherapy of tonsils, the opposing contact surfaces should be sufficiently large that a substantial portion of the tonsil is disposed directly between said surfaces when the tonsil is irradiated. For example, about 20 to 100 percent of the volume of the tonsil parenchyma should be directly between the opposing contact surfaces, and no more than about 80 percent of the parenchyma should extend outside of the region directly between the contact surfaces. More advantageously, about 50 to 100 percent of the volume of the tonsil parenchyma should be directly between the opposing contact surfaces, and no more than about 50 percent of the parenchyma should extend outside of the region directly between the contact surfaces. Most advantageously, about 75 to 100 percent of the volume of the tonsil parenchyma should be directly between the opposing contact surfaces, and no more than about 25 percent of the parenchyma should extend outside of the region directly between the contact surfaces. For very large tonsils, the area of a single light-transmitting contact surface corresponding to irradiation of 100 percent of the compressed parenchymal volume may be as large as approximately 1250 $mm^2$. Furthermore, light transmitted by the contact surface should be evenly distributed for complete and consistent heating of tonsil parenchyma, and to avoid hot spots that may lead to mucosal surface damage. Yet furthermore, in preferred embodiments, the contact surface should be actively cooled. These concurrent objectives of thinness, large area, surface cooling, and uniformity of irradiance require novel optical design for implementation. As is shown herein, there are two approaches which have been found to meet these objectives: (1) a reflective optics design, and (2) a diffusive optic design. Both approaches have advantages and may be used to implement the present invention.

Reflective Optics Design

In this section, for simplicity, the optical design is depicted in drawings showing optical components that may be connected to a single distal portion of a handpiece with the understanding that a apparatus of the invention will comprise two such optical assemblies.

The embodiments described below employ at least one reflecting device within the optical assembly of the apparatus. The reflecting device may be one or more prisms or mirrors.

In one embodiment, the apparatus includes a plurality of reflecting devices, where each reflecting device corresponds to a segment area of light distributed at the light-transmitting contact surface. In another embodiment, each reflecting device corresponds to a plurality of segment areas of light distributed at the light-transmitting contact surface. These corresponding segment areas of are further described below. In certain embodiments, the apparatus includes a cooling device configured to provide coolant fluid to the optical assembly to remove heat from the light transmitting contact surface of at least one of the opposed optical assemblies. In one embodiment, the coolant is brought in direct contact with the plurality of reflecting devices. In a further embodiment, the apparatus includes at least one channel for cooling fluid flow in direct contact with the reflecting devices.

FIG. 20A is a semi-schematic drawing of an optical design comprising a window element 315 and an optical fiber 309. Optical elements transmit and distribute light from the optical fiber to the window element. Surface 311 is the light-transmitting contact surface. In FIG. 20A, the window 315 is square with edge length of approximately 10 mm. Light from the distal end of an optical fiber is transmitted to a 2:1 anamorphic beamshaper 316 and two collimating lenses 317a and 317b, to a first 340 and second 339 prism disposed on the proximal surface of the contact window 315. Prism surfaces 340b and 339b are coated to provide 50% and 100% reflection, respectively. The beamshaper and collimating lenses are selected so that light from the optical fiber substantially fills the proximal face 340a of the first prism. The prisms have a height O of approximately 5 mm, and the window a thickness W of 1 mm. At the light-transmitting contact surface 311, the light is distributed over an approximately square total area 399 with edge length D approximately 10 mm. Light passing through prism 340 is transmitted in segment area 399a and light passing through prism 339 is transmitted in segment area 399b. The distance L from the second collimating lens 317a to the proximal face 340a of the first prism 340 is approximately 20 mm.

In FIG. 20B, the effect of increasing the number of prisms from two to three is shown. Prism surfaces 340b, 339b, and 338b are coated to provide 33%, 50%, and 100% reflection, respectively. Again, the distance from the second collimating lens to the proximal face 340a of the first prism 340 is approximately 20 mm. The light is distributed over an approximately square total area 399 with edge length (D) approximately 10 mm, at the light-transmitting contact surface 311, as in FIG. 20A. Light passing through prisms 340, 339, and 338 are transmitted in segment area 399a, 399b, and 399c, respectively. However, the prism height O is reduced to approximately 3.5 mm, allowing for a significantly thinner optical assembly. With a 1 mm sapphire window, and a 1 mm thick housing, the total thickness is 5.5 mm.

The distance L in FIGS. 20A and 20B is greater than the dimension D of the irradiated area on the contact surface 311. In practice, this will require a straight, rigid section of the handpiece between the fiber exit face and the first prism of over 2 cm. This distance L may be advantageously reduced by adding another collimating lens, as in FIG. 20C. With 3 lenses 317a, 317b, and 317c, L is reduced to approximately 10 mm. Also in FIG. 20C, the number of prisms is increased to four, with surfaces 340b, 339b, 338b, and 337b having reflectivity of 25%, 33%, 50%, and 100%, respectively. Here, the prism height O is reduced to approximately 2.5 mm, while D is maintained at approximately 10 mm. With a 1 mm sapphire window, and a 1 mm thick housing, the total thickness is 4.5 mm.

Cooling capability may be added to a device of FIGS. 20A-C by adding a second window to create a space through which cooling fluid may be introduced, as shown in FIG. 20D. Window 314 is parallel to window 315, such that a coolant layer 345 is formed. Cooling fluid inlet 310a and outlet 310b lines are connected at their proximal ends to a cooling device such as a recirculating chiller (not shown) and at their distal ends with a connector (not shown) at openings in the housing 312 to coolant layer 345. A housing 312 contains prisms 340, 339, 338, and 337, windows 314 and 315, collimating lenses 317a-c, and anamorphic lens 316. Windows 315, the coolant layer 345, and the housing 312 are each about 1 mm thick. Window 315, in a protected position behind window 314, may be thinner than window 314. With windows made of sapphire, the total window thickness may be about 1.5 mm. The prisms may be made of quartz, fused silica, glass, or any other transparent optical material. The total thickness H of the housing and optical components is only 6 mm.

Still further reductions in total thickness can be achieved by increasing the number of reflecting surfaces, as shown in FIGS. 21A-C. Reflecting surfaces can be, for example, surfaces of either solid optical elements such as prisms, or they can be surfaces of mirrors. In this embodiment, the elongated prisms are replaced by elongated mirrors, and light is delivered to the mirror surfaces using individual fibers from a fiber bundle. As used herein, the term elongated is used to describe reflecting devices that have a length sufficient to span across much of the length of the optical assembly. To produce an irradiated square area with edge length 10 mm, five elongated mirrors 441, 442, 443, 444, and 445 are disposed on a contact window 415.

A total of twenty five individual fibers 409a-y are positioned to irradiate twenty five circular areas 498a-y on the angled reflecting surfaces of the mirrors. The proximal ends of the fibers 409a-y are combined in a fiber bundle attached to a light source (not shown). The distal ends 419a-y of fibers 409a-y are disposed in channels within the housing 412, so that light from each fiber is directed towards the elongated mirrors, to form an array of circular irradiated segment areas 498a-y on the mirrors. Reflection from the mirrors then creates an array 499 with D of 10 mm, from the individual segment areas 499a-y on the light transmitting contact surface 411. In FIGS. 21A and B, the fiber distal ends 419a-y are shown as small cylinders, for clarity, whereas in actuality the distal ends may be a simple cleaved or polished surface of the fiber. The size of areas 499a-y may be varied by changing the distance between fiber distal ends 419a-y and the mirrors, for example.

Figure 22A:
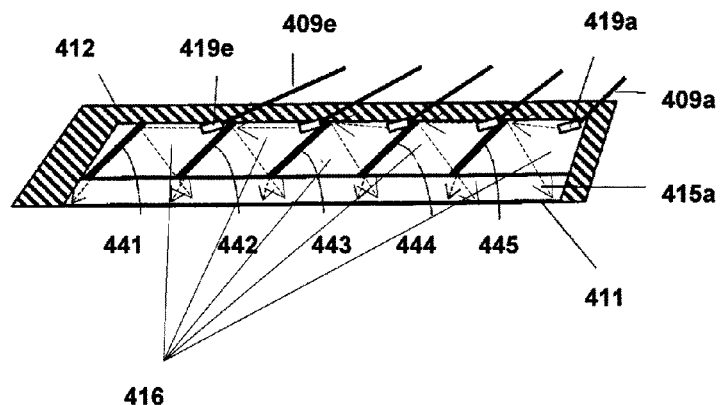
FIGS. 22A and B depict an optical assembly comprising a plurality of elongated mirrors and a cooling channel.
Figure 22B:
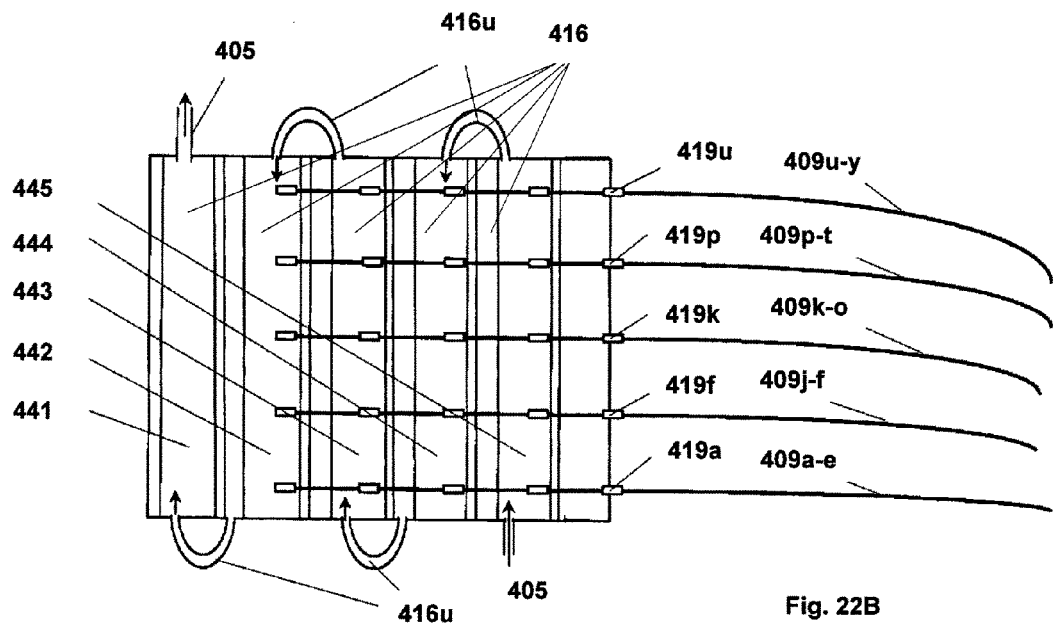

Cooling ability can be added to the device of FIG. 21 by adding a second window in parallel to the first, to provide a cooling layer in between, as in the device of FIG. 20D. However, it is recognized here that the space adjacent to or surrounding the mirrors may be used to cool the optical assembly, with an advantageous reduction in total thickness of the handpiece. The concept is shown schematically in FIGS. 22A and 22B, for the same optical layout as in FIG. 21A-C. For brevity, elements with the same numbers are not described again. Space between the rows of elongated mirrors provides channels 416 for fluid flow. By adding coolant flow redirecting channels 416u at the edge of the optical assembly, a single continuous channel for coolant between inlet 410a and outlet 410b coolant lines can be obtained, that routes fluid evenly over the window and minimizes turbulence or the possibility of air pockets if the fluid is a liquid. A fluid suitable for use in this embodiment is any liquid or gas that is substantially transparent to the wavelength or wavelengths of the light source, and which is nontoxic and biocompatible. Depending on the light source, advantageous choices include cold air, water, and saline. Another advantageous choice is a perfluorocarbon such as Fluorinert™ (3M, Minneapolis, Minn.). Suitable Fluorinerts™ include FC-70 and FC-43, among others. The total thickness of a device as shown in FIG. 22, including housing, is about 4.5 mm, which is very advantageously thin.

Figure 23A:
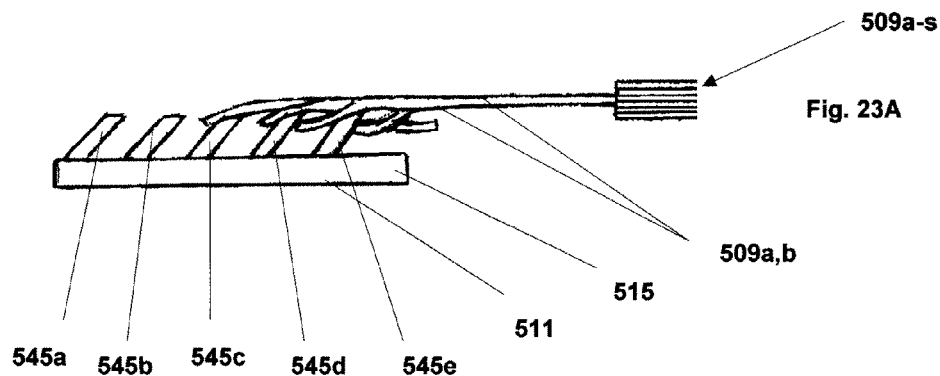
FIG. 23 A-C depict an optical assembly comprising a plurality of mirrors.
Figure 23B:
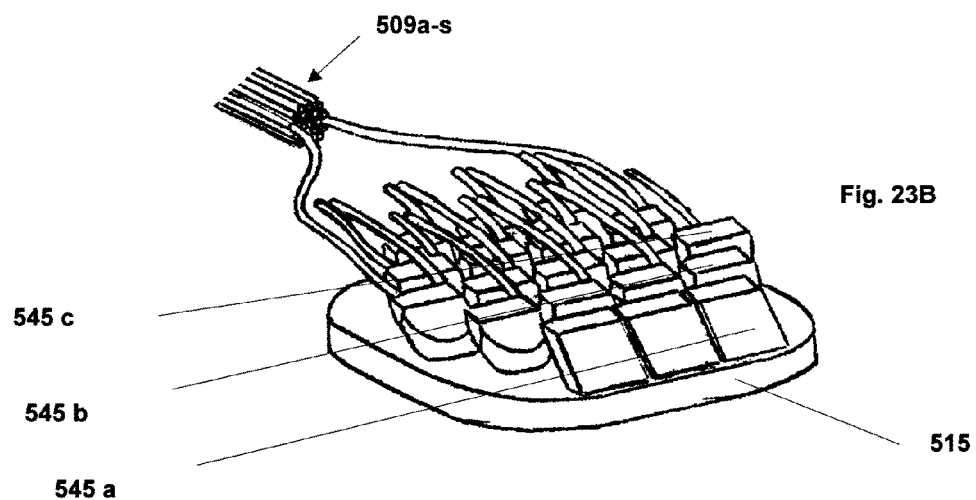
Figure 23C:
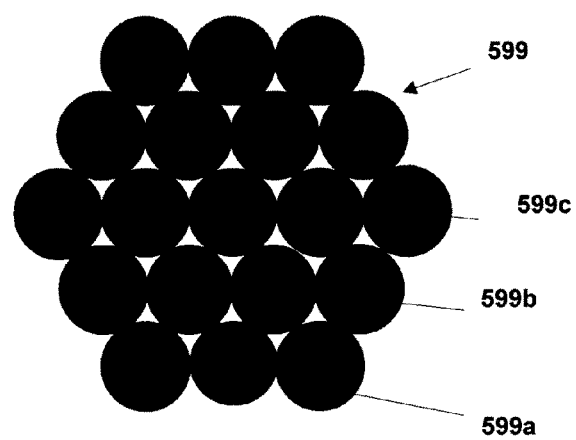

FIG. 23A-C is a semi-schematic depiction of another embodiment of the invention. As shown in FIGS. 23A and B, light is reflected by mirrors, however in this embodiment there is a separate mirror for each individual fiber from a fiber bundle. In this embodiment the mirrors are not considered elongated. Rather, several short mirrors are arranged side by side to span across the length of the optical assembly, as shown in FIG. 23B. The window 515 is a square with edge length 12.5 mm and rounded corners. There are nineteen mirrors 545a-s and nineteen individual fibers 509a-s, arranged to produce circular irradiated segment areas 599a-s of diameter about 2.5 mm each. The irradiated areas on surface form a hexagonally shaped area of substantially uniform irradiation, with dimension D approximately 12.5 mm. Distal ends of fibers 509a-s are disposed within the spaces between the mirrors, to further reduce total thickness to a very thin 3.5 to 4.0 mm. For active cooling capability without increased thickness, coolant fluid may be circulated within the housing, either around the individual mirrors, or in channels produced by setting the mirrors in partitions made of Ultem or other laser-resistant material to guide fluid flow, with insertion holes in said partitions for the distal ends of fibers 509a-s to be placed between mirrors.

As may be appreciated, the irradiation pattern and array size and shape at the contact surface can be readily changed by repositioning the mirrors, and by increasing or decreasing the number of mirrors. An advantage of the reflective optics design is flexibility in producing handpieces with a wide range of contact surface areas and shapes, using a limited number of standardized optical components, for example the mirrors, fibers, and a window. The housing of the embodiments of the invention shown in FIGS. 20-23 may be any biocompatible material known in the art that can be molded or machined, including metals or plastics. The interior of the housing may be coated for reflectivity, or may be uncoated. An advantageous material for the housing includes Ultem, or other such laser-resistant plastic material.

In order to an achieve advantageously thin assembly of optical components within the housing attached to the handpiece distal ends, it is found that a plurality of reflecting devices, for example either prisms or mirrors, may be used. As found using the reflective optics design described herein, the thickness of the housing containing the optical elements may be as small as about 3.5 mm. Irradiated areas of light-transmitting surfaces may be increased to any size, without an increase in thickness, by increasing the number of reflecting devices. A reflective optics design of the present invention also has the important advantage of high transmission efficiency from light source to light-transmitting contact surface. For the design of FIG. 23 A-C with antireflection coatings, losses including Fresnel reflections, absorption of the mirror, and a 9% loss associated with the fiber bundle, yield a total transmission of 86.5% with air cooling. With proper choice of cooling fluid, for example the highly transparent perfluorocarbons, a liquid cooled design may have similar high transmission.

In a reflective optics design, light is transmitted in segments from the light source to the light-transmitting contact surface. The total light at the contact surface is in the form of an array or combination of individual segment areas, each segment area corresponding to a reflecting surface or an area on a reflecting surface. For example, in FIGS. 21B and C the twenty-five segment areas 499a-y correspond to reflecting areas 498a-y on the mirrors, and in FIG. 20A, the two segment areas 399a and 399b correspond to reflections on prisms 340 and 339. As described previously, uniformity of irradiance at the light transmitting contact surface of the apparatus is an objective of the invention. For an apparatus using reflective optics as described herein, uniformity is influenced by several factors, including the placement or pattern of individual segment areas within the contact surface area, the number of individual segment areas, the uniformity of light within each segment area, the amount of overlap between segment areas, and the amount of unirradiated surface in areas between individual segment areas. Also, although the embodiments described herein each have had individual segment areas of a uniform size, a reflective optics design may be implemented to produce an array consisting of segment areas of different size, and/or carrying different amounts of light. A simple and practical method of defining uniformity is therefore to consider the average irradiance within any single circular region located within the total area of the contact surface, said circular region comprising no less than a quarter of the total surface area, regardless of the shape of the total surface area. For any such single region on the contact surface comprising a quarter of the total area, the average irradiance should be no less than 50% above or 50% below the average irradiance over the entire contact surface, for an advantageous device. A more advantageous device has an average irradiance for any single region of one quarter the total surface area that is no less than 25% above or 25% below the average irradiance over the entire contact surface. Most advantageously, the device has an average irradiance for any single region of one quarter the total surface area that is no less than 10% above or 10% below the average irradiance over the entire contact surface.

In an embodiment of the invention in which an optical assembly with the above-described reflective design is used to produce an array of irradiated segment areas within a light-transmitting contact surface area, it may be advantageous to adapt a grid element for contact with said surface by having grid open areas centered, for example, in locations corresponding to the centers of said segment areas.

As demonstrated herein, a reflective optics design has been found which meets the objectives of thinness, uniformity of irradiation, cooling capability, and large light-transmitting surface area.

Diffusive Optics Design

In this section, alternative embodiments of the invention are described, in which the optical assembly comprises a diffusing element In particular, a method and apparatus are described for irradiation using a handpiece with optical components comprising a light guide plate, and having a light-transmitting contact surface. In particular, a method and apparatus are described for transmitting the light output of an optical fiber to a lateral input surface of a light guide plate of the apparatus, such that said light output propagates transversely within the light guide plate, in a direction that is substantially parallel to the tissue surface. The light output of an optical fiber is distributed over a contact surface of an optical element of the apparatus, such that when said contact surface is placed adjacent to the area of tissue to be irradiated, said surface transmits light to irradiate said area of tissue. Said contact surface is substantially parallel to the light guide plate.

The optical elements exposed to light from the optical fiber, including light guide plate, windows, and other optical components, as well as air gaps and fluid layers located between said optical components, and as positioned and contained within the housing of the apparatus, are collectively referred to as the optical stack, for the embodiments of the invention described in this section, said embodiments also referred to as diffusive optics embodiments. An optical stack contains at least one optical component. Herein, for any optical component of the optical stack, said component having two opposing surfaces, the component surface that is closer to the light-transmitting contact surface of the device, or which is a light-transmitting contact surface, is referred to as the distal surface of said component. Likewise, the component surface that is further from the a light-transmitting contact surface of the device is referred to as the proximal surface of said component. The optical stack has a proximal end boundary which is a substantially reflective surface. In some embodiments said substantially reflective boundary surface is an interior surface of the housing. In other embodiments the substantially reflective boundary surface is a light reflecting plate. The device of the invention may comprise one or more optical stacks. The optical stack may be contained in a housing that is attached to a distal portion of the handpiece. Herein, an optical assembly is an optical stack or a housing containing an optical stack.

The optical assembly and at least one optical stack it comprises may take various forms and configurations in the diffusive optics embodiments of the present invention, but in each the optical stack comprises a substantially rigid light guide plate. A substantially rigid light guide plate is a plate made of quartz or sapphire for example. A light guide plate made of an optical plastic, for example acrylic or polycarbonate, is also an example of a substantially rigid light guide plate. The light guide plate accepts light at a lateral edge from an optical fiber and provides a path for transverse propagation by TIR. The light guide plate is transparent to light emitted by the light source of the system, and may be composed of a rigid material or it may be a fluid layer or flexible layer bounded and constrained by adjacent rigid optical components. The optical assembly also comprises a light-transmitting contact surface, which is a surface in contact with tissue when said optical assembly is irradiating a tissue surface. In some embodiments, light is transmitted from the distal surface of the light guide plate to a contact surface of a window element that is in contact with the tissue and that is substantially parallel to the light guide plate. In some embodiments the contact surface is a surface of the light guide plate. The light guide plate may be planar, with plane parallel distal and proximal surfaces, or said plate may have planar surfaces formed at an angle for a wedged shape. In other embodiments, one or both of the distal and proximal surfaces of the light guide plate may be nonplanar, having a convex, concave, or any other advantageous shape, such that the area of each of said surfaces is large compared to the output surface of the distal end of the optical fiber, and such that the propagation of light from the lateral input edge is substantially parallel to the tissue surface. The optical assembly of present invention provides a substantially rigid light guide plate, such that the transmission efficiency and uniformity of irradiance from the optical assembly are not affected by the conformation of tissue surface being treated.

The light guide plate of the optical assembly of the invention has extraction features that serve to disrupt TIR during transverse propagation and distribute light over the contact surface with substantial uniformity. Extraction features may be formed over all or part of the light guide plate by removal of material from the light guide plate, for example as etched, ground, milled, or ablated areas, dots, spots, lines, or grooves, or may be formed by application of material to the surface of the light guide plate, for example scattering or diffusive material applied to said surface in areas or a pattern or distribution of dots, spots, lines or grooves. Said applied materials may comprise paints and/or formulations of a substance or substances with index of refraction equal to or higher than the index of the material of the light guide plate, and which are substantially reflective of and substantially non-absorbent of the wavelength or wavelengths of light emitted from the optical fiber. Such substances may include barium sulfate, titanium dioxide, silicon dioxide, tantalum oxide, magnesium oxide, aluminum oxide, calcium carbonate, sulfur, polytetrafluoroethylene, polymethylmethacrylate, polycarbonate, glass, and the like, and mixtures of these substances. The applied material may also include a binder for mechanical stability. The binder may be an organic or inorganic substance. The applied material, including reflective substance and binder, is substantially reflective at the wavelength or wavelengths of the light source of the system. Preferably, the applied material of the extraction features, has a reflectivity of at least approximately 95%, at the wavelength or wavelengths of the light source of the system. Alternatively, the extraction features of the light guide plate may be made by a molding process, or by a combination of molding, removal, and/or application of material.

In an aspect of the invention, the size, shape, pattern or distribution of extraction features is selected to produce a substantially uniform irradiance at the contact surface. In another aspect of the invention, the pattern or distribution of extraction features is selected to produce high transmission efficiency and a substantially uniform irradiance at the contact surface. Preferably, transmission efficiency is 50% or higher. Most preferably, transmission efficiency is 80% or higher. Preferably, irradiance at the contact surface has uniformity of approximately +25% to −25% or better. Most preferably, said irradiance has uniformity of approximately +10% to −10% or better.

The contact surface of the optical assembly is in thermal contact with the tissue surface during irradiation with the optical assembly. Heat generated in the tissue by absorption of light during irradiation may be transferred from the tissue to one or more elements of the optical stack of the optical assembly, in a passive process. The optical element of the contact surface of a passively cooling optical assembly is advantageously made of a material that has high thermal conductivity. Most advantageously, the optical element of the contact surface of a passively cooling optical assembly is made of sapphire.

In preferred embodiments, the apparatus of the invention comprises a cooling device, and the optical assembly contains a coolant layer. The coolant layer may be an element of the optical stack or may be external to the optical stack. The coolant layer actively cools one or more elements of the optical stack and the tissue being irradiated. The coolant layer is adapted for the flow of a cooling fluid, which may be either a gas or a liquid. The temperature of the cooling fluid is maintained approximately at or below the physiological temperature of 37° C. by the cooling device, which is connected to the optical assembly and which circulates coolant fluid into and out of the coolant layer of the optical assembly. An aspect of the invention is that the cooling fluid is biocompatible and nontoxic. In preferred embodiments, the coolant layer is external to the optical stack. In advantageous embodiments, the cooling fluid comprises water or air. Preferably, the optical element of the contact surface of an actively cooling optical assembly is made of a material that has moderate to high thermal conductivity. Preferably, the optical element of the contact surface of an actively cooling optical assembly is made of quartz, fused silica, or sapphire, or the like.

In some embodiments of the invention, the optical stack of the optical assembly comprises one or more heat transfer layers. Said heat transfer layer comprises fluid with high thermal conductivity and substantial transparency at the wavelength or wavelengths of light emitted by the light source. In some embodiments, the at least one heat transfer layer is disposed between optical components of the optical stack, such as between two window elements or between a window element and the light guide plate. In other embodiments of the invention, a heat transfer layer is disposed between an optical component and a reflecting plate at the proximal boundary of the optical stack. In other embodiments of the invention, the extraction features of the light guide plate are configured to transfer heat from the light guide plate through an air gap to a reflecting plate at the proximal boundary of the optical stack.

In an aspect of the invention, the housing is made of a substantially rigid moldable or machinable biocompatible material, for example, Ultem In another aspect of the invention, the interior surface of the housing does not substantially absorb wavelength or wavelengths of the source connected to the optical fiber. In another aspect of the invention, all or part of the interior surface of the housing is specularly or diffusely reflective. In some embodiments of the invention, all or part of the interior surface is coated with a material that is diffusely reflective of the wavelength or wavelengths of light being transmitted by the optical fiber. In some embodiments of the invention, all or part of the interior surface has a coating made of gold or other reflective material. In some embodiments of the invention, some or all of the lateral edges of one or more optical components of the optical stack are polished or coated.

According to an aspect of the invention, the light guide plate and/or optical stack is made as thin as possible. In addition to reducing the thickness of the optical assembly, minimizing the thickness of the light guide plate and/or optical stack also reduces the number of scattering events and mean pathlength of photons between the optical fiber distal end and the contact surface, resulting in improved efficiency of the optical assembly.

The objectives of the invention, namely thinness, large light-transmitting contact surface area, surface cooling, and uniformity of irradiance are met by the diffusive optics strategy of the present invention, as is shown here. The elements of the optical stack and optical assembly are configured in a novel manner, to achieve this combination of advantageous qualities relating to shape, and optical and thermal performance. The aspects and advantages of the present invention can be further understood from the following detailed description of the embodiments.

The diffusive optics design has an additional advantage of particular importance The output from the light-transmitting contact surface may be Lambertian, or nearly Lambertian, that is, with rays randomly oriented and highly divergent. Light rays may be transmitted orthogonally at the contact surface, or have any angle including a grazing angle that is approximately parallel to the contact surface. By contrast, the reflective optics design of the previous section may produce light that is more highly directed and less randomly oriented, for example a nearly collimated beam, a divergent beam, or an array of multiple slightly divergent beams. In the reflective design, rays are transmitted in a direction that is substantially orthogonal to the contact surface, an arrangement that is more similar to the collimated irradiation of the mathematical model calculations presented previously herein. Commonly, a collimated or a divergent or convergent beam that is not randomly directed as in a diffuse or Lambertian beam is seen as advantageous in phototherapy. Such a beam may be readily focused, and may provide the greatest depth of penetration in tissue. A collimated or divergent/convergent beam or beams such as produced by the reflective optics design of the previous section are therefore well suited for treatment of tonsils and other soft tissues, by the methods and apparatus of the present invention.

A Lambertian or diffuse output has previously unrecognized advantages, however. In the present invention a tonsil may be held and compressed between two light-transmitting contact surfaces. If the tonsil as held extends beyond the edges of said surfaces, at least one portion of the tonsil may not be subjected to irradiation. Either the handpiece will need to be reapplied to the at least one portion of the tonsil that was not irradiated, or, more advantageously, a handpiece having optical assemblies with contact surfaces large enough to treat the entire tonsil is used.

If however, the contact surfaces are sufficiently large that the surfaces extend beyond the edges of a tonsil held and compressed between the surface, for example if a relatively small tonsil is held by a handpiece with optical assemblies having contact surfaces sufficiently large to treat an entire very large tonsil with one application of irradiation, then the small tonsil will be subject to light on a portion of mucosal surface on its medial side that is between the contact surfaces but not touching said surfaces. Light transmitted from the portion of the contact surfaces that extend beyond the edges of the small tonsil being will impinge upon said uncontacted tonsil mucosal surface portion. Because said tonsil mucosal surface portion is uncontacted, it is uncooled by the contact surfaces. Therefore, a potential exists for light to heat the uncontacted mucosal surface portion of a smaller tonsil that is held in handpiece with optical assemblies that are appropriate for larger tonsils. The light may intersect with the uncontacted mucosal tissue in a primarily glancing angle, so that actual damage to the mucosal surface may not occur. However, such considerations suggest that it may be desirable to use handpieces with a set of optical assemblies with more than one contact surface area, for tonsil of different size ranges.

The diffusive optics design of the invention provides an advantageous method of treating tonsils of various designs. Tissue exposed to radiation from a Lambertian source at a distance will receive less light than tissue exposed to a collimated source. With a collimated source, the density of light at the tissue surface at a distance is unchanged, whereas for a Lambertian source, the density of light decreases as the square of the distance. This property of Lambertian sources has been used in the development of eye safe lasers for dermatology, to avoid eye injury when a laser or other light source is accidentally directed towards the eye. According to the present invention, however, a Lambertian, nearly Lambertian, or similar diffuse beam may be used in intentional treatment of tissue such that tissue at a distance from a light transmitting contact surface is not subjected to excess light. Specifically, if a smaller tonsil is held and gently compressed between two light-transmitting contact surfaces, each with Lambertian, nearly Lambertian, or diffuse output, where said contact surfaces extend beyond the medial mucosal surface of the small tonsil, then the light density in the space between extending portions of the two contact surfaces will fall off significantly before impinging on the medial mucosal surface of the tonsil, thus sparing said surface potential unwanted heating, even if high irradiation powers are used.

Consequently, the diffusive optics design of the present invention provides a method and apparatus for tonsil treatment that reduces or eliminates the need for multiple optical assemblies to provide treatment for a wide range of tonsil sizes. As noted above, the depth of penetration of light in tissue is maximized by using a collimated beam with light rays normal to the tissue surface. However, a photon of light will have lost its original orientation after about $(1-g)^{-1}$ scattering events, which in tonsils is about 1 mm into the tissue. Therefore, the diffusive optical design may be used with similar results within contacted tissue as the reflective optics design, particularly if slightly enhanced cooling is provided to compensate for the slightly increase distribution of light at the surface of tonsil tissue in contact with the light-transmitting contact windows during irradiation. Because the cooling requirements of tonsil tissue according the present invention are not aggressive, a very slight enhancement of cooling, for example by a few degrees, may suffice. In this section, for simplicity, the optical design is depicted in drawings showing optical components associated with a single handpiece distal portion, with the understanding that a handpiece will comprise two such distal portions.

In the embodiments described below, the optical assembly of the apparatus include a light diffusing element, thereby enabling the device to emit diffuse radiation. In addition, the optical element of the optical assembly or optical assemblies includes a light guide plate having a lateral light input surface at a lateral surface such that light traversing the light guide plate propagates through the light guide plate in a direction that is substantially parallel to the tissue surface. The light diffusing element includes extraction features on a proximal surface of the light guide plate such that light reflected from the extraction features is transmitted through the light-transmitting contact surface in a substantially uniform distribution. The extraction features may be present on one or both sides of the light guide plate. The apparatus may be furnished with a housing enclosing at least a portion of the light guide plate. The housing may have an opening at the lateral light input surface of the light guide plate.

From an understanding of the embodiments described below, it will be apparent that many other embodiments are possible.

First Embodiment

FIGS. 24A and B are a schematic depiction of a simple first embodiment of the device of the invention. As will be described in detail below, in this embodiment, the distal surface of the light guide plate serves as the light-transmitting contact surface. The optical element includes an air gap adjacent to a proximal surface of the light guide plate. The air gap is enclosed by the base interior surface and the lateral interior surface of the optical assembly housing.

FIG. 24A shows the circular contact surface 611 of the optical assembly. The contact surface 611 is flush with the edge surface 612e of the device housing 612. An optical fiber 609 is attached at or near its light-emitting distal end to the housing 612 with a connector 608. The proximal end of the optical fiber is attached to a laser or other light source (not shown).

FIG. 24B is a schematic cross-section depiction of the housing and optical stack of this embodiment. Inside the housing 612 is a light guide plate 600 with proximal surface 600a, and distal or contact surface 611. The housing 612 has an opening 612a for entry of light from the optical fiber 609. The opening 612a is positioned so that the output of the optical fiber is substantially transmitted to the light guide plate 600 through lateral input surface 600c of said light guide plate. The housing provides a small space or air gap 650 between its base interior surface 612d and the proximal surface 600a of the light guide plate. Extraction features 600e are applied to all or part of the proximal surface 600a of the light guide plate, in patterns or distributions that vary spatially over said surface. Light transmitted from the optical fiber through the lateral surface of the light guide plate is internally reflected within the light guide plate, and is scattered by the extraction features on the proximal surface of said light guide plate so that said light is substantially emitted from the distal surface of said light guide plate. The base interior surface 612d and lateral interior surface 612f of the housing is coated, covered, or made with a substantially reflective material.

All or part of the lateral surfaces of the light guide plate, with the exception of the lateral input surface 600c adjacent to the output face of the optical fiber, may be optically polished and coated with gold, or left unpolished and coated with a diffusively reflecting substance such as barium sulfate paint. The lateral input surface 600c may be polished or unpolished but is not reflective.

The light emitted from the light guide plate distal surface 600b is substantially Lambertian, that is, with rays randomly directed. The irradiance at said surface is substantially uniform. For clarity, FIG. 24B shows the irradiated area 699 at a distance from the distal surface of the light guide, or contact surface. The irradiated area 699 on a tissue surface in contact with the light guide plate distal surface is substantially the same shape and area as the light guide plate distal surface.

Figure 25A:
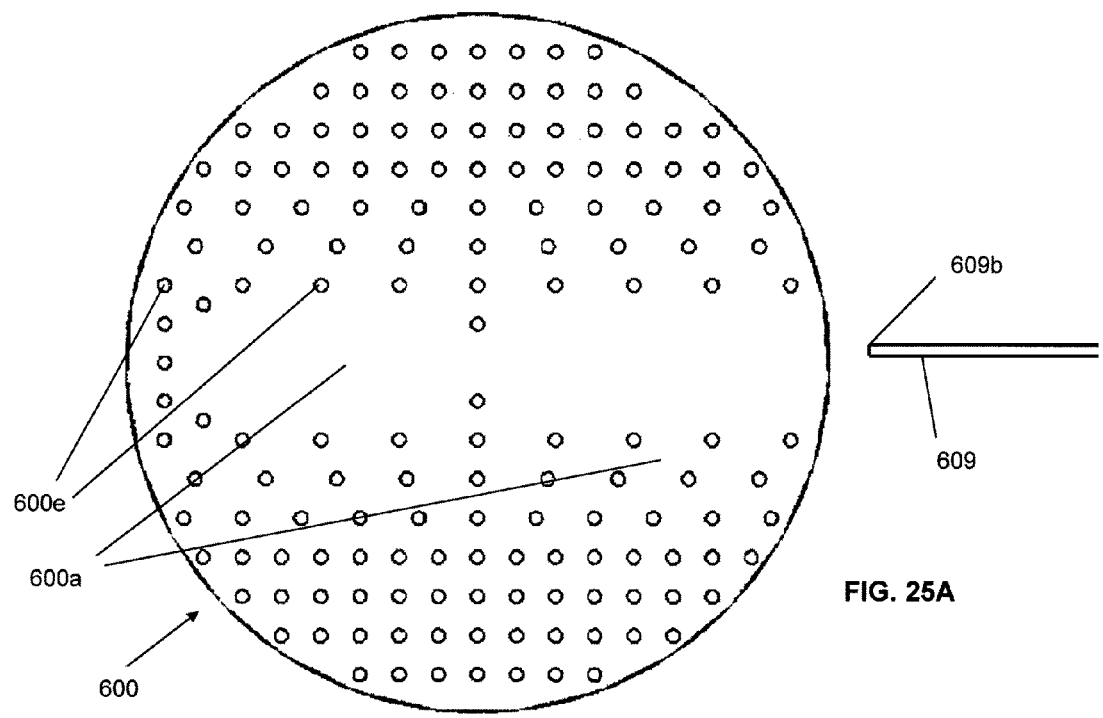
FIGS. 25 A and B are schematic views of a light guide plate with extraction features on one surface.
Figure 25B:
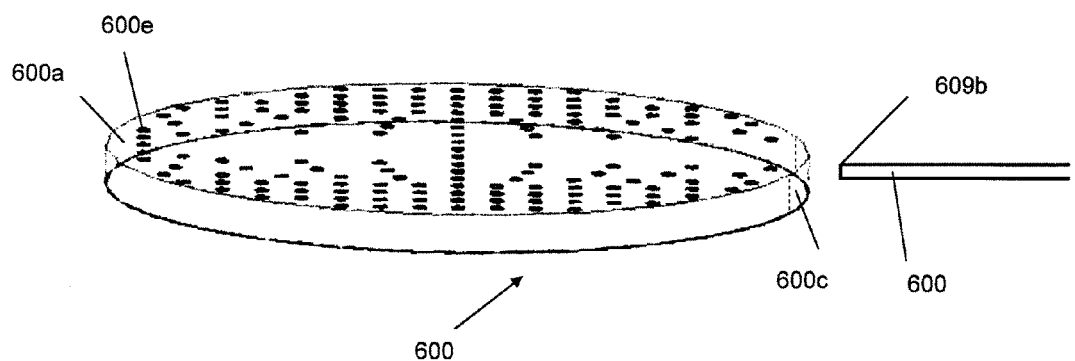

The extraction features 600e on the proximal surface 600a of the light guide plate 600 are shown in greater detail in the schematic views of FIGS. 25A and B. FIG. 25A shows the proximal surface of the light guide plate. The optical fiber 609 exit face 609b is in close proximity to the light guide plate lateral input surface. The tilted view of FIG. 24B shows the light input area 600c on the light guide plate lateral surface.

The extraction features shown in 40e are greatly enlarged and arbitrarily distributed for clarity in FIGS. 25A and B, and are not intended to depict an actual pattern or size of extraction features. The pattern and distribution of extraction features corresponding to an optical assembly with high uniformity of light distribution and high output efficiency depend on the optical materials and geometry of a optical stack, and a general pattern and distribution that would be optimal for the optical stack of all devices does not exist. The extraction features of the light guide plate in this embodiment are on the proximal surface of said plate. In other embodiments, extraction features may be on both the proximal and distal surfaces of said plate.

The thickness of the air gap 650 is greater than approximately twice the wavelength or wavelengths of light from the light source, or sufficient to allow TIR at the light guide plate proximal surface.

An aspect of the first embodiment is that the light guide plate is made of a rigid material that has a higher index of refraction than air. Examples of suitable materials include glass, fused silica, quartz, acrylic, and sapphire. Preferably the light guide plate has a thickness that is sufficient for coupling substantially all of the light emitted from an optical fiber of given numerical aperture (NA) and distance from the light guide input surface. Preferably the light guide plate is not substantially thicker than is necessary for flexure strength and resistance to breakage, and for coupling substantially all of the light emitted from the optical fiber.

This simple first embodiment of the invention is an optical assembly that passively cools the tissue surface by conduction of heat by the light guide plate in thermal contact with said tissue surface. Passive cooling capability may be enhanced by using a light guide plate made of a sapphire. Sapphire is an highly advantageous material for the contact element of the invention, due to its very high thermal conductivity of 58 W/m K, high flexure strength of 1200 MPa, resistance to scratching (hardness 1370 kg/mm$^2$), and very high transmission from 190 nm into the infrared. When sapphire is used as the light guide plate, it is found that the strength of this material allows a minimum thickness of approximately 1 mm to be used for light emitting surfaces of up to about 4 cm diameter.

Sapphire cannot be molded. Because of its hardness sapphire is relatively resistant to etching. Extraction features may also be made by applying diffusive material, for example by screen printing. Suitable diffusive materials include paints or formulations of reflective substances, with some binder to provide mechanical stability, as described previously. Suitable materials include barium sulfate paints commercially available for reflectance coatings, such as Duraflect, Spectraflect, and Labsphere 6080 (Labsphere, North Sutton, N.H.), or formulated according to published methods.

When the light guide plate is fused silica, glass, quartz, or acrylic or other transparent plastic, extraction features may be made by screen printing, as is the case with sapphire. Alternatively, the extraction features may be made in these materials by an etching or molding process. Molding is a less expensive process in volume, but is limited to features on an approximately millimeter scale. Use of these larger scale features may limit the uniformity of irradiance, depending on the size and shape of the light guide plate. Etching can be performed to produce smaller, denser, and more complex extraction features. An optical assembly of this first embodiment with light guide plate made of fused silica, glass, plastic, or quartz will provide passive cooling of tissue, although to a lesser extent than sapphire. All of these materials have higher thermal conductivity than air: quartz has a value of 7.5 W/m K, fused silica 1.4 W/m K, glasses between 0.51 and 1.28 w/m K, and polymethylmethacrylate approximately 0.2 W/m K. Quartz, fused silica and glass are highly transmissive in the visible and near infrared. However, with these substances, the thickness of the light guide should be sufficient to prevent breakage, or at minimum approximately 2 mm or more. Plastics (acrylics, polystyrenes, and polycarbonates) have absorption bands beginning at approximately 1100 nm which makes them less efficient for use with wavelengths of approximately 1100 nm or longer. Plastics typically have lower transmission in the visible and near-infrared wavelengths shorter than approximately 1100 nm than sapphire, quartz, fused silica, or glass, and their use as a light guide plate material will result in relatively poor efficiency for the optical assembly. Because of the relatively low thermal conductivity of plastics (0.1 to 0.3 W/m K), a system of the first embodiment with a plastic light guide plate will provide relatively inefficient passive cooling. For these reasons of poor efficiency and poor cooling, and because plastic optical components may be damaged by high power light sources, plastic has relatively limited utility in the optical assembly of this embodiment. More advantageous light guide plates are sapphire with applied extraction features comprising reflective substance such as barium sulfate, or quartz, fused silica, and glass with etched or molded extraction features.

Advantages of the first embodiment are simplicity for phototherapeutic applications requiring only passive cooling. In some cases, the optical assembly of the first embodiment can be precooled by placing it in contact with ice, cold water, or chilled air prior to use, to enhance passive cooling.

Second Embodiment

As will be described in detail below, in this embodiment, the optical element of the apparatus includes an air gap adjacent to a proximal surface of the light guide plate. The air gap is enclosed by the base interior surface and the lateral interior surface of the optical assembly housing. The optical element also includes a cooling layer adjacent to the distal surface of the light guide plate. The contact window has a proximal surface adjacent to the cooling chamber and an exposed distal surface that serves as the light transmitting contact surface of the optical assembly.

Figure 26A:
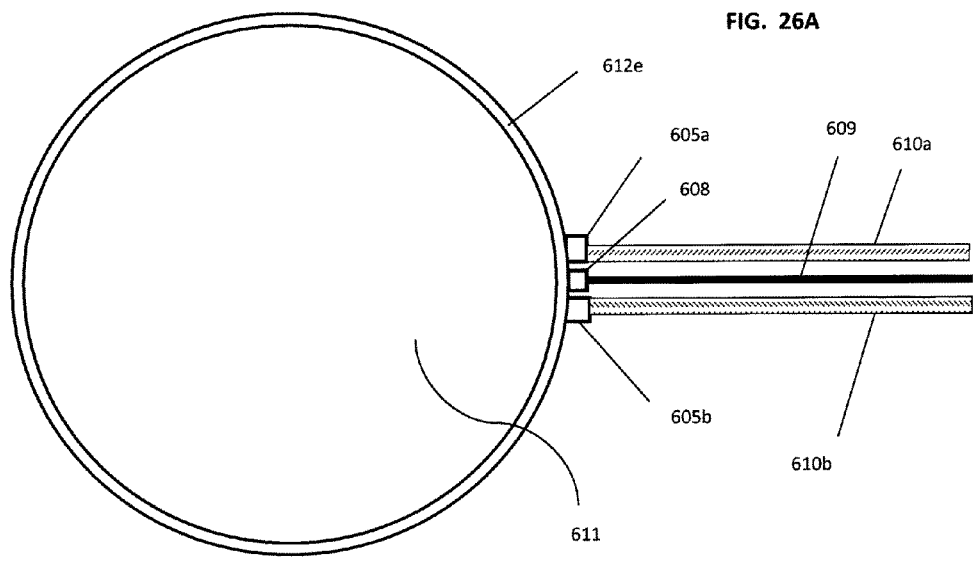
FIGS. 26 A and B depict an optical assembly comprising a light guide plate and a cooling layer.

FIGS. 26 A and B are a schematic depiction of an embodiment of the invention that includes active cooling capability. FIG. 5A shows the circular light-transmitting distal surface 611 of a contact window. The contact surface 611 is flush with the edge surface 612e of the device housing 612. An optical fiber 609 is attached at or near its light-emitting distal end to the housing 612 with a connector 608. The proximal end of the optical fiber is attached to a laser or other light source (not shown). The device also has inlet 610*a* and outlet 610*b* lines for flow of coolant fluid, connected to the housing 612 with inlet 605*a* and outlet 605*b* tubing connectors. The other ends of the coolant lines are connected to a cooling device (not shown). The cooling device may be a recirculating chiller with coolant fluid reservoir, or a cold air producing device.

Figure 26B:
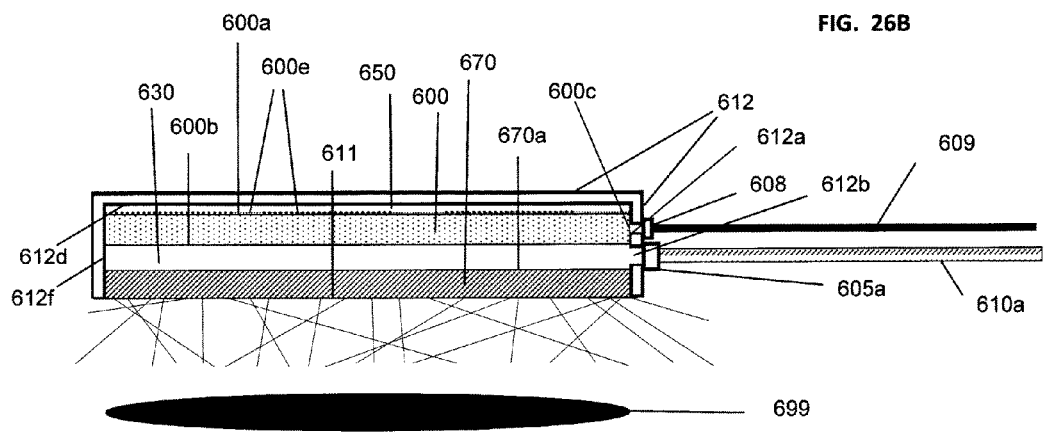

FIG. 26B is a schematic cross-section depiction of the housing and optical stack of this embodiment. Inside the housing 612 are a light guide plate 600, cooling layer 630, and contact window 670. The light guide plate 600 has a proximal surface 600*a* and distal surface 600*b*. The housing 612 has an opening 612*a* for entry of light from the optical fiber 609. The opening 612*a* is positioned so that the output of the optical fiber is substantially transmitted to the light guide plate 600 through lateral input surface 600*c* of said light guide plate. The openings in the housing for the coolant flow tubes are positioned so that coolant flows into and out of the cooling layer 630. The inlet opening 612*b* is depicted. The housing provides a small space or air gap 650 between its base interior surface 612*d* and the proximal surface 600*a* of the light guide plate. The contact window 670 has a proximal surface 670*a* in contact with coolant in the cooling layer 630, and distal contact surface 611. Extraction features 600*e* are applied to all or part of the proximal surface 600*a* of the light guide plate, in patterns or distributions that may vary spatially over said surface. Light transmitted from the optical fiber through the lateral input surface of the light guide plate is internally reflected within the light guide plate, and is scattered by the extraction features on the proximal surface of said light guide plate so that said light is substantially transmitted from the distal surface of said light guide plate. The base interior surface 612*d* and lateral interior surface 612*f* of the housing is coated, covered, or made with a substantially scattering material.

Coolant flowing into the cooling layer 630 cools the contact window and extracts heat from tissue in contact with said window. Coolant flow also may reduce any heating of other components of the device resulting from internal scattering and absorption of light by optical elements and reflective surfaces including the housing interior surface. In an aspect of this embodiment of the invention, the fluid is substantially non-absorbent of light being transmitted through the coolant chamber. In another aspect of this embodiment, the fluid absorbs less than approximately 25% of the light being transmitted through the coolant chamber. Preferably, the fluid absorbs less than approximately 10% of said light. Most preferably, the fluid absorbs approximately 5% or less of said light. Examples of suitable fluids include water, saline, perfluorocarbon such as Fluorinert™ (3M, Minneapolis, Minn.), and air, depending on the light source wavelength or wavelengths. For example, at a wavelength region where water has an absorption of greater than 5 or 10% over the cooling layer thickness, a more advantageous cooling fluid may be perfluorocarbon or air. The cooling capability of the optical assembly is determined by the heat transfer properties of the fluid, the temperature of the fluid, and the rate of flow of fluid within the cooling layer.

The light transmitted from the contact window distal surface 611 is substantially Lambertian, that is, with rays randomly directed. The irradiance at said surface is substantially uniform. The irradiated spot 699 on a tissue surface in contact with the contact window distal surface is substantially the same shape and area as the contact window.

Another aspect of this embodiment is that the contact window is made of a rigid material that is substantially transparent to the light of the source connected to the optical fiber. Examples of suitable materials for the contact window include fused silica, quartz, glass, acrylic, and sapphire. Preferably, the contact window material has moderate to high thermal conductivity. The contact window material may be quartz, fused silica, glass or sapphire. An advantageous contact window material has both a high thermal conductivity and high flexure strength. Most advantageously, the contact window material is sapphire.

In an aspect of the invention, the interior surface of the housing does not substantially absorb light of the source connected to the optical fiber. In a advantageous aspect of the invention, all or part of the interior surface is coated with a material that is highly reflective of the wavelength or wavelengths of light being transmitted by the optical fiber.

An aspect of the second embodiment is that the light guide plate is made of a material that has a higher index of refraction than the cooling fluid. Examples of suitable materials include fused silica, quartz, acrylic, and sapphire, depending on the cooling fluid. Preferably the light guide plate has a thickness that is sufficient for coupling substantially all of the light emitted from an optical fiber of given NA and distance from the light guide input surface. Preferably the light guide plate is not substantially thicker than is necessary for flexure strength and resistance to breakage, and for coupling substantially all of the light emitted from the optical fiber. If the contact window is sapphire, a light guide plate made of quartz, fused silica, or glass may be protected from damage by said window and the thickness of said light guide plate may be reduced, compared to the first embodiment in which the light guide plate is exposed.

A sapphire light guide plate of the second embodiment will have applied extraction features, and a quartz, silica, acrylic or glass light guide may have applied molded, or etched features, as describe previously for the case of the first embodiment. Also as in the first embodiment, the thickness of the air gap 650 is greater than approximately twice the wavelength or wavelengths of light from the light source, or sufficient to allow TIR at the light guide plate proximal surface.

In this embodiment, the thickness of the light guide plate and optical stack are minimized. The light guide plate thickness is determined by coupling efficiency with the light source, and the contact window by strength requirements. The cooling layer may be approximately 1 mm in thickness, for cooling with water, perfluorocarbon, or air.

Third Embodiment

As will be described in detail below, in this embodiment, the optical element includes a first air gap adjacent to a proximal surface of the light guide plate. The first air gap is enclosed by the base interior surface and the lateral interior surface of the optical assembly housing. The optical element further includes a second air gap between the distal surface of the light guide plate and the proximal surface of a coolant layer window. A coolant layer is between the coolant layer window and the proximal surface of a contact window. The exposed distal contact surface serves as the light-transmitting contact surface.

Figure 27:
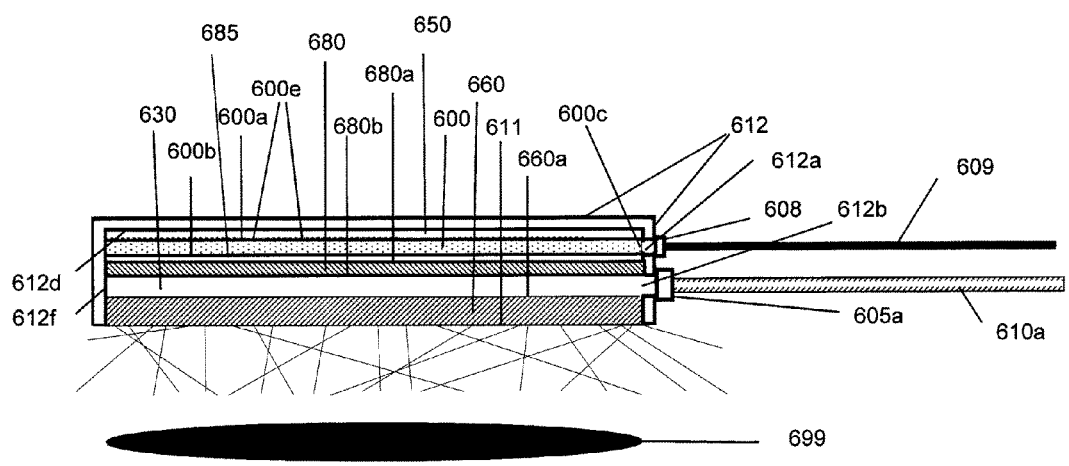
FIG. 27 depicts an optical assembly comprising a light guide plate, a cooling layer, and a cooling layer window.

FIG. 27 is a schematic cross-section depiction of the housing and optical stack of a third embodiment of the invention. As in the second embodiment, the third embodiment has active cooling capability, however the optical stack has a minimal air gap between the light guide plate and a cooling layer window, to reduce scattering within the optical stack and thereby improve efficiency, compared to an optical stack of the second embodiment with approximately the same thickness.

Inside the housing 612 are a light guide plate 600, a cooling layer window 680, a cooling layer 630, and a contact window 660. The light guide plate 600 has a proximal surface 600*a* and distal surface 600b. The housing 612 has an opening 612a for entry of light from the optical fiber 609. The opening 612a is positioned so that the output of the optical fiber is substantially transmitted to the light guide plate 600 through an input area 600c on the lateral surface of said light guide plate. The openings of the housing for the coolant flow tubes are positioned so that coolant flows into and out of the cooling layer 630. The inlet opening 612b is depicted. The housing provides a small space or first air gap 650 between its base interior surface 612d and the proximal surface 600a of the light guide plate. The cooling layer window 680 has a distal surface 680b in contact with cooling fluid in the cooling layer 630, and a proximal surface 680a in contact with air. The cooling layer window proximal surface 680a is separated from the light guide plate distal surface 600b by a space or second air gap 685 of at least 2 microns thickness, or at least twice the wavelength or wavelengths of the light source. The contact window 660 has a proximal surface 660a in contact with coolant in the cooling layer 630 and distal contact surface 611. Extraction features 600e are formed by application or removal of material, or molding, to all or part of the proximal surface 600a of the light guide plate, as described previously. Light transmitted from the optical fiber through the lateral input surface of the light guide plate is propagated by TIR within the light guide plate in a direction that is substantially parallel to the light guide plate proximal 600a and distal surfaces 600b. TIR is partially disrupted by the extraction features 600e on the proximal surface of said light guide plate, such that light is scattered and emitted from the distal surface 600b of said light guide plate. Said emitted light is propagated through the second air gap 685, cooling layer window 680, cooling layer 630, and contact window 660, to irradiate an area 699 on the tissue surface in contact with the contact window. The base interior surface 612d and lateral interior surfaces 612f of the housing is partially or completely coated, covered, or made with a substantially reflective material. All or part of the lateral surfaces of the coolant window and contact window may be coated or covered with a diffusively or specularly reflective material. All or part of the light guide plate lateral surfaces, with the exception of the lateral input surface, may be coated or covered with a diffusively or specularly reflective material.

In an aspect of this embodiment of the invention, the fluid is substantially transparent to light being transmitted through the cooling layer. In another aspect of this embodiment, the fluid absorbs less than approximately 20% of the light being transmitted through the cooling layer. Preferably, the fluid absorbs less than approximately 10% of said light. Most preferably, the fluid absorbs approximately 5% or less of said light. Examples of suitable fluids include water, saline, perfluorocarbon, and air, depending on the wavelength or wavelengths of the light source.

An aspect of the third embodiment is that the light guide plate is made of a material that has a higher index of refraction than air. Examples of suitable materials include fused silica, quartz, acrylic, and sapphire. Preferably the light guide plate has a thickness that is sufficient for coupling substantially all of the light emitted from an optical fiber of given NA and distance from the light guide input surface. Preferably the light guide plate is not substantially thicker than is necessary for flexure strength and resistance to breakage, and for coupling substantially all of the light emitted from the optical fiber. If the contact window and/or cooling layer window is sapphire, a light guide plate made of quartz, fused silica, or glass may be protected from damage by said window and the thickness of said light guide plate may be reduced.

The light transmitted from the contact window distal surface 611 is substantially Lambertian, that is, with rays randomly directed. The irradiance at said surface is substantially uniform. The irradiated area 699 on a tissue surface in contact with the contact window distal surface is substantially the same shape and area as the contact surface.

In an aspect of this embodiment of the invention, the pattern or distribution of extraction features on the light guide plate is selected to produce a substantially uniform irradiance at the distal surface of the contact window. In another aspect of this embodiment of the invention, the pattern or distribution of extraction features is selected to produce high transmission efficiency and a substantially uniform irradiance at the distal surface of the contact window. Preferably, transmission efficiency is 50% or higher. Most preferably, transmission efficiency is 80% or higher. Preferably, irradiance at the distal surface of the contact window has uniformity of approximately +25% to −25% or better. Most preferably, said irradiance has uniformity of approximately +10% to −10% or better.

Fourth Embodiment

In a fourth embodiment of the invention, the cooling layer may be disposed between the proximal surface of the light guide plate and the interior surface of the housing. Specifically, the cooling layer is adjacent to a proximal surface of the light guide plate, and is enclosed by the base interior surface and the lateral interior surface of the optical assembly housing. An advantage of this embodiment of the invention is that the light guide plate is also the contact window, so that the thickness of the optical stack is reduced while providing active cooling. Reducing the thickness of the optical stack reduces internal scattering and increases transmission efficiency, as well as making the device advantageously thin. In this embodiment, a distal surface of the light guide plate serves as the light-transmitting contact surface.

Figure 28:
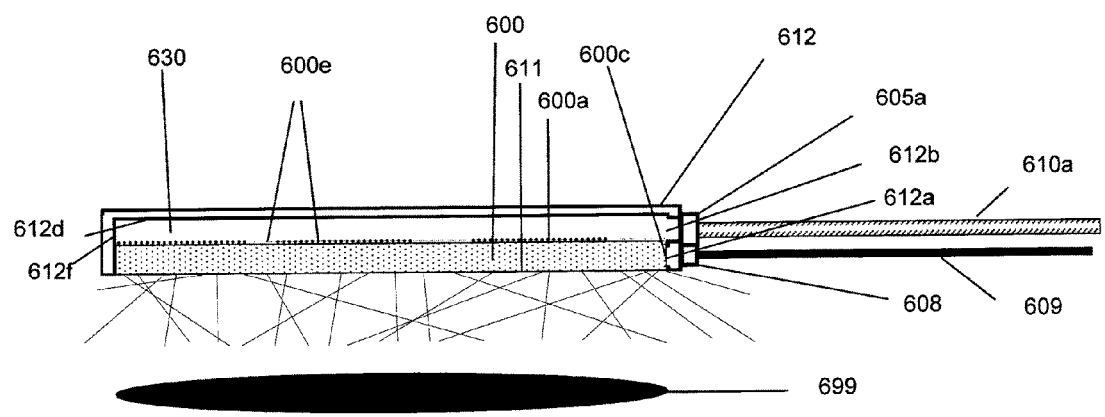
FIG. 28 depicts an optical assembly comprising a light guide plate, with cooling layer disposed adjacent to light guide plate proximal surface.

FIG. 28 is a schematic cross-sectional depiction of the housing and optical stack of this embodiment. Inside the housing 612 is a light guide plate 600 and a cooling layer 630. The light guide plate 600 has a proximal surface 600a and distal contact surface 600b. The housing 612 has an opening 612a for entry of light from the optical fiber 609. The opening 612a is positioned so that the output of the optical fiber is substantially transmitted to the light guide plate 600 through lateral input surface 600c of said light guide plate. The openings of the housing for the coolant flow tubes are positioned so that coolant flows into the cooling layer 630. The inlet opening 612c is depicted. Extraction features 600e are applied to all or part of the proximal surface 600a of the light guide plate, in patterns or distributions that vary spatially over said surface. Light transmitted from the optical fiber through the lateral surface of the light guide plate is propagated transversely by TIR within the light guide plate, and is scattered by the extraction features on the proximal surface of said light guide plate so that said light is substantially emitted from the distal or contact surface 611 of said light guide plate. The base interior surface 612d and lateral interior surface 612f of the housing is coated, covered, or made with a substantially reflecting material. The irradiated spot 699 on a tissue surface in contact with the contact window distal surface is substantially the same shape and area as the contact window.

In an aspect of this third embodiment of the invention, the coolant fluid is substantially transparent to light being transmitted through the coolant chamber. The fluid may be a liquid or a gas. In another aspect of this embodiment, the fluid absorbs less than approximately 20% of the light being transmitted through the optical assembly. Preferably, the fluid absorbs less than approximately 10% of said light. Examples of suitable fluids include water, saline, perfluorocarbon, air, or nitrogen gas, depending on the wavelength of the light source.

An aspect of the present embodiment is that the light guide plate is made of a material that has a higher index of refraction than the coolant fluid in the cooling chamber. Examples of suitable materials include fused silica, quartz, acrylic, and sapphire. The light guide plate may have a thickness that is sufficient for coupling substantially all of the light emitted from the optical fiber. Preferably the light guide plate is not substantially thicker than is necessary for coupling substantially all of the light emitted from the optical fiber and for strength. Preferably the light guide plate material has a moderate to high thermal conductivity. An advantageous he light guide plate is sapphire, and the extraction features of the light guide plate are a diffusing material applied in the form of an adherent paint or pigment that is resistant to the fluid of the cooling layer. For example, the diffusing material is barium sulfate applied in the form of Duraflect coating material (Labsphere, North Sutton, N.H.), and the cooling fluid is water, saline, perfluorocarbon, air or nitrogen gas, depending on source wavelength. The diffusing material may be in a form that may not be highly resistant to flowing liquid, for example barium sulfate pain applied in the form of Labsphere 6080 coating material (Labsphere, North Sutton, N.H.), in which case an advantageous cooling fluid is air or nitrogen gas. Another advantageous light guide plate material is quartz, fused silica, or glass, and the extraction features are formed by application or removal of material, or molding. If extraction features are formed by etching or molding, the light guide plate can be exposed to flowing liquid or gas in the cooling layer. The quartz, fused silica, or glass light guide plate is of sufficient thickness to provide adequate resistance to breakage. The present embodiment of the invention requires cooling fluid substantially free of particulate impurities and may also include a filtration system to minimize contamination of the extracting features of the light guide plate.

In another aspect of this embodiment of the invention, the pattern or distribution of extraction features is selected to produce high transmission efficiency and a substantially uniform irradiance at the distal surface 611 of the light guide plate.

Fifth Embodiment

In a fifth embodiment of the invention, a reflecting plate is disposed between the cooling layer and the proximal surface of the light guide plate. Specifically, the cooling layer is enclosed by a base interior surface and a lateral interior surface of the optical assembly housing, and the reflecting plate The reflecting plate and an extraction space are present between the cooling layer and a proximal surface of the light guide plate. The extraction space is adjacent to the proximal surface of the light guide plate. An advantage of this reflective plate is that extraction features on the light guide plate proximal surface are protected from erosion or dissolution by, or contamination or reaction with, the flowing coolant of the cooling layer. A further advantage of the reflective plate is that the cooling layer is not part of the optical stack and is not exposed to light. The coolant fluid is therefore not limited to gases or liquids that are substantially transparent light of the wavelength or wavelengths emitted from the optical fiber. Consequently, water, an advantageous coolant fluid because its good heat transfer capability, low cost, and biocompatibility, can be used in this embodiment of the invention even at wavelengths where there is substantial absorption of light by water In this embodiment, the distal surface of the light guide plate serves as the light-transmitting contact surface.

Figure 29:
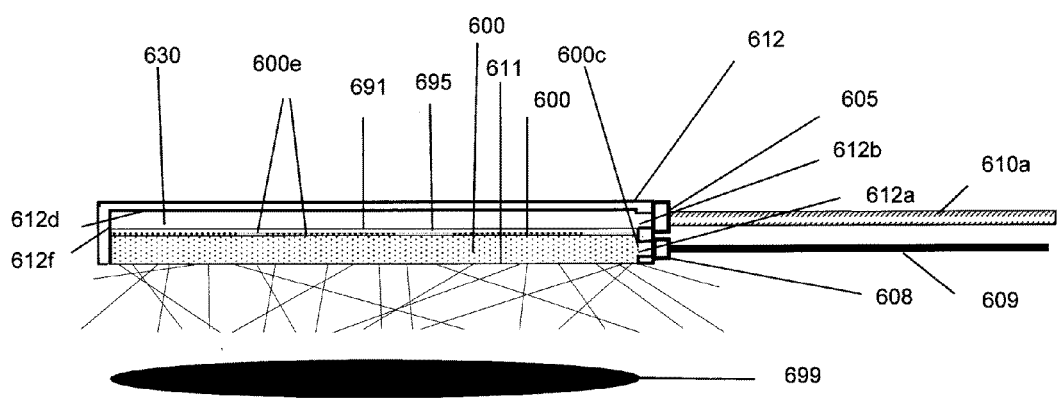
FIG. 29 depicts an optical assembly comprising a light guide plate and a reflecting plate, with cooling layer disposed adjacent to the reflecting plate.

FIG. 29 is a schematic cross-sectional depiction of the housing and optical stack of the fifth embodiment. Inside the housing 612 is a light guide plate 600 and a cooling layer 630. The light guide plate 600 has a proximal surface 600a and distal contact surface 611. A thin reflective plate 691 is disposed adjacent to but not in contact with the proximal surface 600a of the light guide plate. An extraction space 695 is provided between the light guide plate 600 and the reflective plate 691. The extraction space 695 is at least 2 μm in thickness, or at least twice the wavelength of the light source. The housing 612 has an opening 612a for entry of light from the optical fiber 609. The opening 612a is positioned so that the output of the optical fiber is substantially transmitted to the light guide plate 600 through lateral input surface 600c of said light guide plate. The openings of the housing for the coolant flow tubes are positioned so that coolant flows into the cooling layer 630. The inlet opening 612b is depicted. Extraction features 600e are applied to all or part of the proximal surface 600a of the light guide plate, in patterns or distributions that vary spatially over said surface. Said light transmitted from the optical fiber through the lateral surface of the light guide plate is propagated transversely by TIR within the light guide plate, and is scattered by the extraction features 600e on the proximal surface of said light guide plate so that said light is substantially transmitted from the distal or contact surface 611 of said light guide plate. The base interior surface 612d and lateral interior surface 612f of the housing is coated, covered, or made with a substantially non-absorbent material. The irradiated spot 699 on a tissue surface in contact with the contact window distal surface is substantially the same shape and area as the contact window.

In another aspect of the fifth embodiment of the invention, the extraction space 695 may contain a substantially static amount of air, gas, or liquid that is substantially transparent to the light transmitted by the optical fiber, and with refractive index lower than the light guide plate. It is advantageous for the extraction space to contain a liquid with high thermal conductivity, for example perfluorocarbon (Fluorinert™, 3M, Minneapolis Minn.). The perfluorocarbon preferably has a boiling point well above room temperature and relatively low vapor pressure, such as Fluorinert™ FC-43 or FC-70, among others. Fluorinert™ fluids typically increase in volume by 1% for every 10° C. temperature increase. An aspect of this embodiment is that the thin reflective plate 691 is metallic and sufficiently thin to provide for change in volume with temperature of the fluid in the extraction space 695. Circulation in the cooling layer of a fluid maintained at 2° C., an approximately minimum temperature required to prevent ice formation or tissue freezing at the contact surface, reduces the temperature of a static fluid in the extraction space 695 originally at room temperature by approximately 20° C. The flexibility of a thin metal reflective plate can adequately adapt to an approximately 2% change in liquid volume without distortion and possible bubble formation within the extraction space. The reflective plate may be polished or coated with a diffusively reflective material on all or part of its surface in contact with the extraction layer.

An aspect of the present embodiment is that the light guide plate is made of a material that has a higher index of refraction than the material within the extraction space 695. Examples of suitable materials include fused silica, quartz, acrylic, and sapphire. The light guide plate may be sapphire with applied extraction features, or quartz, fused silica or glass with etched or molded extraction features. When the difference between refractive indices of fluid of the extraction space and the light guide plate is relatively small, for example if the fluid is Fluorinert and the light guide plate is etched quartz, fused silica or glass, etched feature are created of sufficient depth to effectively scatter and extract light from the light guide plate.

In an aspect of this fifth embodiment of the invention, the pattern or distribution of extraction features is selected to produce a substantially uniform irradiance at the distal surface of the light guide plate. In another aspect of this embodiment of the invention, the pattern or distribution of extraction features is selected to produce high transmission efficiency and a substantially uniform irradiance at the distal surface of the light guide plate, as defined previously.

The present embodiment has many advantages, as it contains only one optical component in the optical stack for minimal thickness, has a cooling layer outside the optical stack to eliminate light absorption by cooling fluid and allow use of water as coolant, and can be configured with components having high thermal conductivity for excellent cooling capability.

Sixth Embodiment

As will be described in detail below, in this embodiment the optical element includes a cooling layer enclosed by a base interior surface and a lateral interior surface of the optical assembly housing. The optical element further includes a reflecting plate between the coolant chamber and the light guide plate. The reflecting plate has a surface that is in contact with the extraction features on the proximal surface of the light guide plate. The optical element still further includes at least one extraction space enclosed by the reflective plate, the proximal surface of the light guide plate, and the extraction features.

In the sixth embodiment, the reflective plate 691 is in thermal contact with the extraction features on the light guide plate proximal surface. The extraction features comprise a material with both substantially high thermal conductivity and substantially high reflectance at the source wavelength or wavelengths. The extraction features are in thermal contact with the reflective plate, providing efficient heat transfer from the light guide plate to the coolant chamber without fluid in the extraction space. Preferably, the reflective plate 691 is made of metal. Preferably, the reflective plate is polished or has a diffusive reflective coating on the side in contact with the extraction features. Most preferably, the reflective plate has a diffusive reflective coating on the side in contact with the extraction features, for good thermal contact.

Figure 30A:
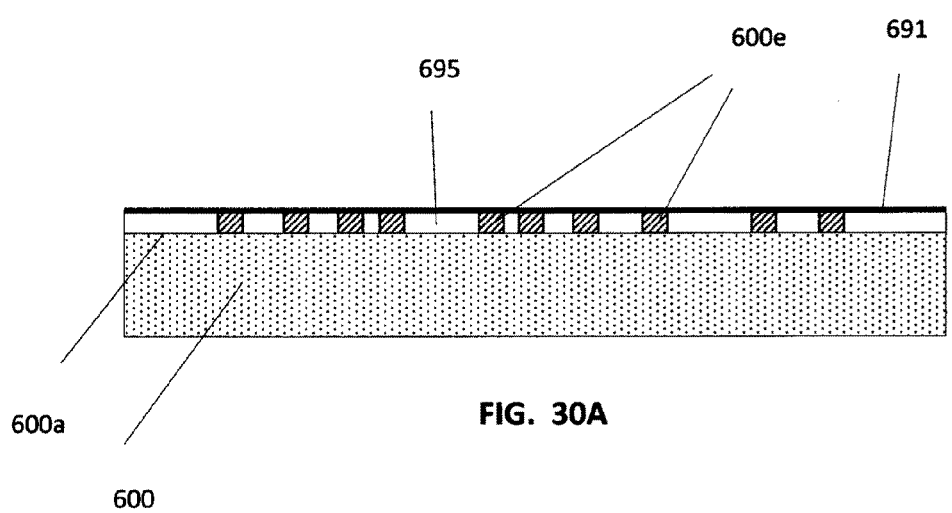
FIGS. 30 A and B depict extraction features of a light guide plate in contact with a reflecting plate or a coating on a reflecting plate.
Figure 30B:
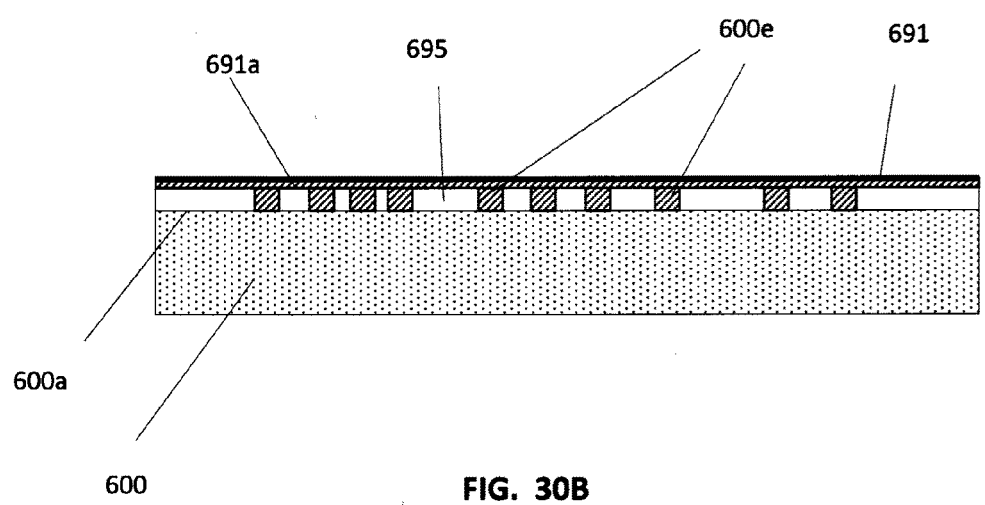

FIGS. 30A and B are schematic depictions of this embodiment. In FIG. 30A the extraction features 600*e* of the proximal surface 600*a* of a light guide plate 600 are in contact with the reflective plate. In FIG. 30B the extraction features 600*e* are in contact with a coating 691*a* of the reflective plate 691.

According to the sixth embodiment of the invention, the extraction features serve the purpose of both disrupting TIR in the light guide plate, and of transferring heat from the coolant layer through the reflective plate to the light guide plate. An advantage of this embodiment is that no liquid needs to be contained in the extraction space 695 to achieve good heat transfer between coolant fluid outside the optical stack, and the contact window. Extraction features formed of applied material, such as paint applied by screen printing, may have thickness on the order of tens to hundreds of microns, which is more than sufficient to provide an air gap between light guide proximal surface 600*a* and reflective plate of at least 2 microns when the reflective plate is in contact with the top surface of the dots.

An important aspect of this embodiment of the invention are the thermal characteristics of the extraction features. Formulations used for creation of extraction features are typically composed of reflective material, binder, and solvent. Solvent will evaporate as the formulation dries, leaving a printed array of features composed of reflective material and binder. In this embodiment, the reflective substance is substantially reflective at the wavelength or wavelengths of the light source, and a substance with thermal conductivity substantially greater than that of the surrounding air in the extraction space (0.024 W/(mK)). Examples include barium sulfate, titanium dioxide, and zirconium oxide. The reflective substance may have a reflectivity of greater than approximately 90%. Higher thermal conductivities are more advantageous.

Seventh Embodiment

In this embodiment of the invention, the optical assembly is adapted to emit light in a more directed manner. An advantage of this embodiment that may be useful in certain applications is that light that is more collimated or directed will have a greater depth of penetration in tissue.

Figure 31:
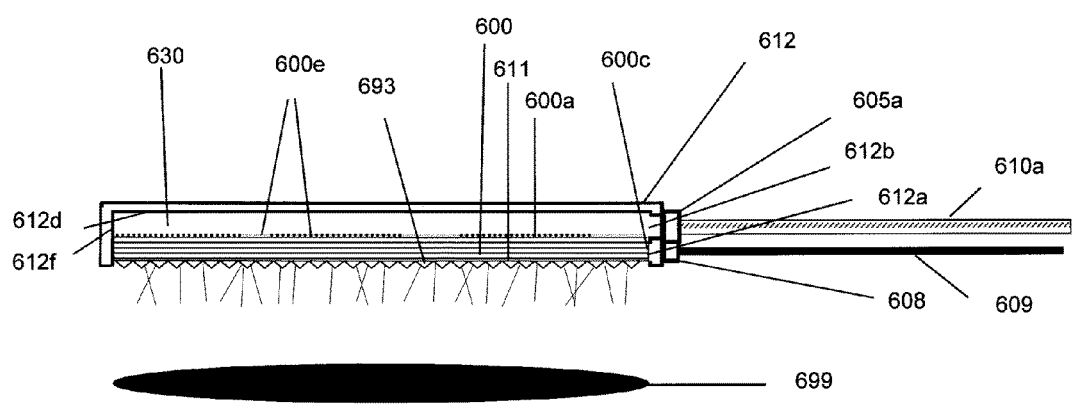
FIG. 31 depicts an optical assembly with a light guide plate and focusing features.

FIG. 31 is a schematic depiction of the seventh embodiment. This Figure is similar to FIG. 7, and for brevity the features of this embodiment that are the same as the fifth embodiment are given the same numbers and their description is not repeated here. The new aspect of this embodiment are the collimating features 693 of the light-transmitting surface 611 shown in FIG. 31. The focusing features may be a series of ridges, grooves, lens arrays, and the like, to focus and make less divergent the transmitted light. In this embodiment, the focusing features at the distal surface of the light guide plate serve as the light-transmitting contact surface.

Alternatively, the focusing features may be in the form of a grid element, having ridges, grooves, lenslet array, and the like, that is attached to a light-transmitting contact surface that does not have those features.

In either case, whether the focusing features are part of an element of the optical assembly or are part of a grid element, the features may be located over all or part of the light transmitting contact surface. For example, the features may be located near the center of the contact surface, so that light transmitted from the remainder of the contact surface is still Lambertian or nearly Lambertian.

Chromophore Elements

The mathematical model laser-tissue interaction calculations described previously have shown that tonsils of the range of size that are removed in tonsillectomy procedures, and with various composition corresponding to vascularity and fibrosis, can be heated to target temperatures for thermal injury in irradiation periods of several minutes or less, according to the invention as has been disclosed herein. In general, it is desirable to reduce as much as possible the total operative time including the irradiation period. With this objective, as a further improvement, the present invention includes embodiments having a chromophore element that is inserted in the tonsil tissue prior to irradiation and removed after treatment is complete. This chromophore element may also advantageously modifying the heat distribution in the tissue, as will be shown below.

Figure 32:
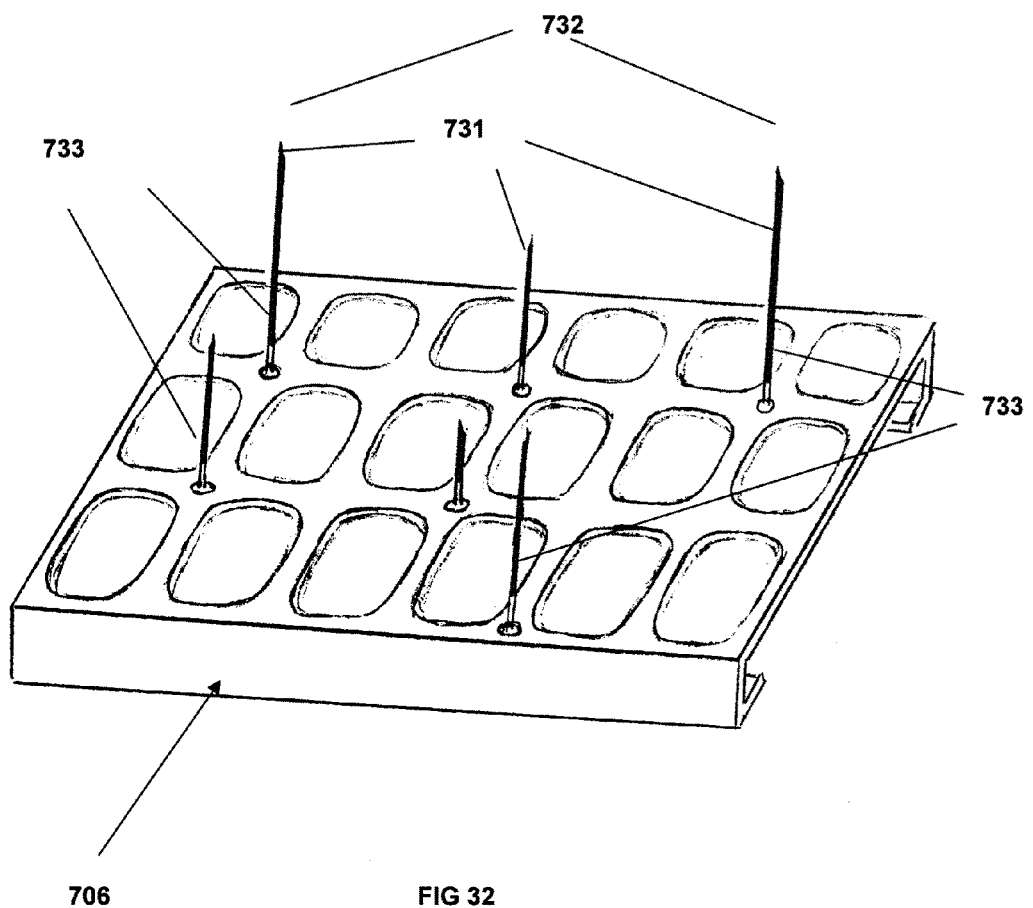
FIG. 32 depicts a grid element with attached chromophore needles.

According to an embodiment of the invention, a grid element 706 has attached needles 731 that are made of or have as a component, a light-absorbing chromophore, as shown schematically in FIG. 32. These needles are chromophore elements of the invention, and have a proximal end 733 and a distal end 732. Any number of chromophore needle elements may be used, and may be used in combination with sensor needles on a single grid element. It is advantageous for the proximal end 733 of the chromophore needle to have a surface that substantially reflects light. For example, the proximal end of the chromophore needle should reflect light so that the mucosal surface of the tonsil tissue in contact with said needle proximal end is not thermally injured by said proximal end. The reflecting proximal end of the chromophore needle should be at least as long as the mucosal surface thickness, or approximately 200 μm long. It is more advantageous for the reflecting proximal end to be longer than the mucosal surface thickness, for example about 0.5 mm or 1 mm long.

Figure 33:
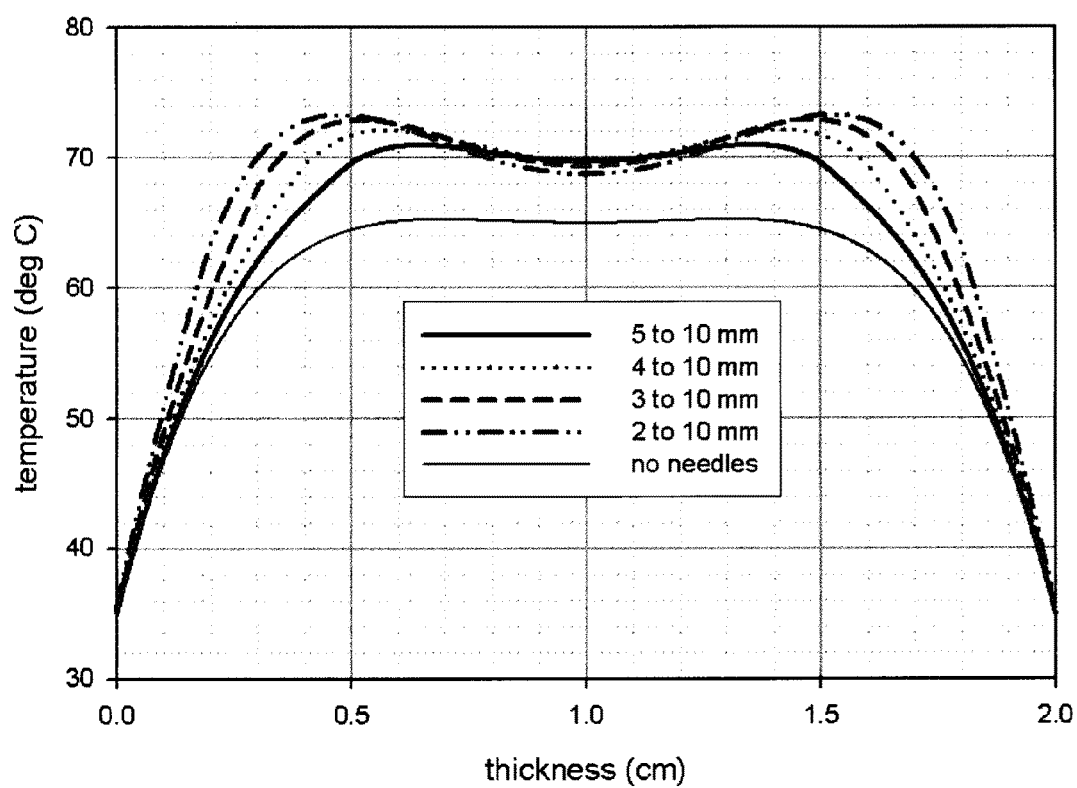
FIG. 33 shows the results of model calculations for tonsil treatment with chromophore needles having differing amounts of chromophore coating.

FIG. 33 shows the results of model calculations for tonsils of average size removed in tonsillectomy. In these calculations, the contact element is 2.6 cm in diameter, which corresponds to approximately the full diameter of a 14 g tonsil when compressed to a thickness of 2.0 cm. In the model, there are 21 chromophore needles in a cubic pattern with edge length of 4 mm. Each chromophore needle is 1 mm in diameter. Also, in this example, chromophore needles are each 10 mm in length, and have a light absorbing chromophore coating on the distal end, and a light-reflecting coating on the proximal end. In the model calculations, the length of the distal end that is coated by chromophore is varied from 5 to 8 mm. Light is absorbed by both the tonsil tissue and the distal surface of the chromophore needle, specifically, the portion of the surface that is coated with light-absorbing chromophore. The chromophore absorption coefficient is 1000 cm$^{-1}$ in these calculations. The tonsil tissue at the depth of the needle distal end is heated in the regions between the needles during irradiation because the irradiation time is orders of magnitude greater than the thermal relaxation time of the chromophore needle. The expression $t_r = d^2/16\tau$, where $\tau$ is thermal diffusivity and d is diameter, gives the thermal relaxation time for a cylinder. If made of stainless steel, the thermal relaxation time for a cylindrical needle of diameter 200 microns, 500 microns, or 1 mm is 0.6, 3.8, and 15 ms, respectively. If the needle is made of titanium, the respective thermal relaxation times are 0.3, 1.8, and 7 ms. Each needle is thermally isolated from other needle or sensor elements by the grid to which it is attached at its proximal end. The needle may be made of or contain different materials, in order to select its thermal mass, heat transfer coefficient, and heat capacity as required to optimize heat transfer to the surrounding tissue for a particular application.

As seen in FIG. 33, the calculations indicate that the heat distribution within the tonsil when treated according to the present invention using chromophore needles will depend on the location of the light-absorbing chromophore on the needle. Here, tonsil tissue closer to the surface of the tonsil can be heated more by extending the chromophore coating closer towards the proximal end of the chromophore needle.

Figure 34:
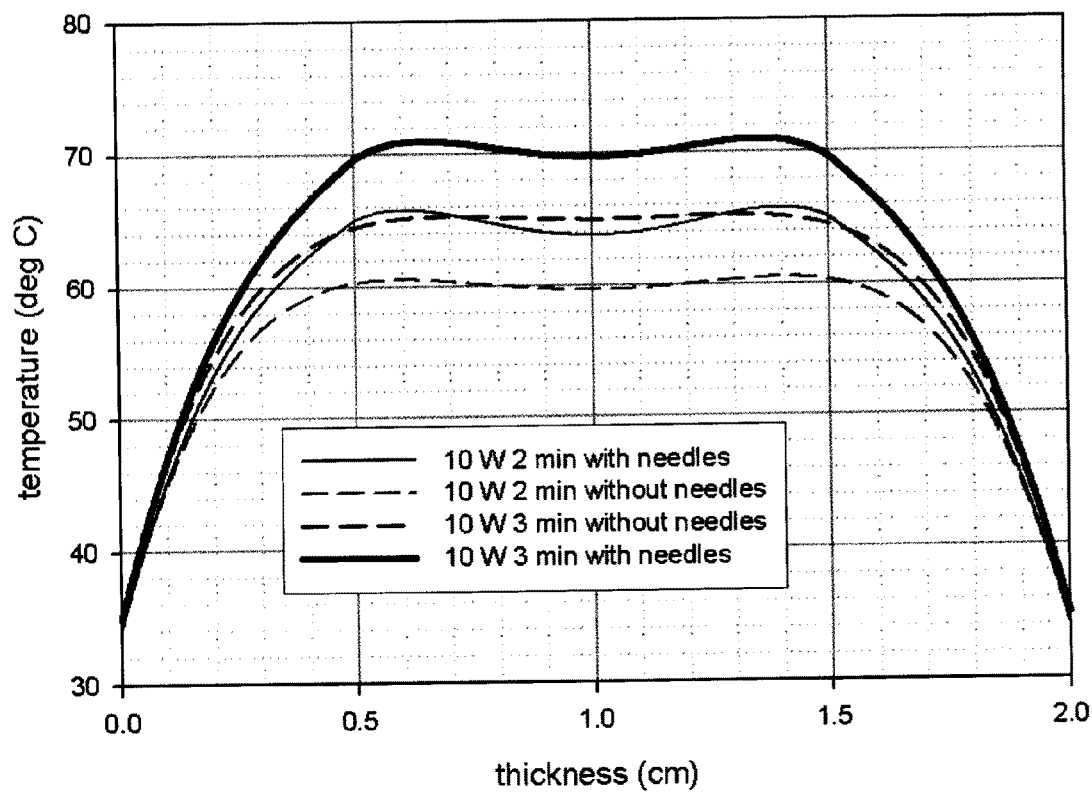
FIG. 34 shows the results of model calculations for tonsil treatment with and without chromophore needles.

As can be seen in FIG. 34, the presence of the needles allows the tonsil tissue to be heated in a time period that is substantially shorter than when no needles are used, for example in a time period that is 33% less than when no needles are used. A decrease in irradiation time is of significant advantage in reducing total operative time.

According to an embodiment of the invention, the grid with chromophore needles is attached to the optical assemblies of the handpiece with the longitudinal axes of the needles normal to the light-transmitting contact surface of the optical assembly, or at an angle that facilitates grasping of the tonsil, for example, at an angle of 45 degrees or less from normal. The chromophore needles are long enough that when the tonsil is held and compressed by the contact surfaces, the distal end of the chromophore needle will be inserted to a position within the tonsil at a depth below the mucosal layer. Preferably, the chromophore needle is between 0.2 mm and 20 mm in length. More preferably the chromophore needle is between 1 and 10 mm in length. According to an aspect of the invention, chromophore needles of different lengths may be attached to a single grid element. According to an aspect of another embodiment, the chromophore needles attached to the grid of one surface element may be of a different length or lengths from the chromophore needles attached to the grid of a second surface element.

In another embodiment, the chromophore needles are oriented with their axes parallel to the contact elements. In yet another embodiment of the invention, the chromophore needles are attached to a collar element that is attached to the handpiece, such that the chromophore needles are oriented with their axes parallel to the contact elements.

Also according to the invention, the chromophore needles have a diameter between approximately 100 microns and 3 mm. Preferably, the chromophore needles have a diameter of approximately 200 microns and 1 mm. The diameter of the chromophore needle may vary as a function of distance from proximal tip to distal tip. In a preferred embodiment, the diameter is substantially constant over the length of the chromophore needle. In another preferred embodiment, the diameter of the distal end of the chromophore needle is substantially larger than the diameter of the proximal end. The chromophore needle may be substantially straight, or with an angle of curvature over all or part of its total length.

According to the invention, the chromophore needles are made of a biocompatible material that has sufficient strength and rigidity to penetrate the tonsil with minimal risk of breakage. In a preferred embodiment, the chromophore needles are made of medical grade stainless steel (316, 316L or vacuum melted type 316L). In another preferred embodiment, the chromophore needles are made of medical grade titanium (unalloyed commercially pure CP grades 1-4) or titanium alloys (including Ti-6Al-4V ELI, Ti-6Al-4V, Ti-6Al-7Nb, Ti-3Al-2.5V, Ti-13Nb-13Zr, Ti-12Mo-6Zr-2Fe, Ti-15Mo.) Other metallic materials that can be used to make the chromophore needles include gold, silver, platinum, tantalum, niobium, zirconium and zirconium alloys, shape memory alloys based on the nickel-titanium binary system, tungsten and tungsten bronzes, and cobalt alloys (Elgiloy and MP35N). In an aspect of the preferred embodiment, the metal or metal alloy that is used to make the chromophore needle is coated with a chromophore that absorbs NIR light. In another aspect of the preferred embodiment, the chromophore coating is applied to the surface of a distal portion of the chromophore needle. (The term distal is used herein to describe the portion of a element or component that is further from the light source, for example the laser cavity). In an aspect of another preferred embodiment, the chromophore coating is applied to the entire surface of the chromophore needle. In another preferred embodiment, a coating that substantially reflects light is applied to the surface of a proximal portion of the chromophore needle.

The chromophore needles may also be made of ceramic materials. In a preferred embodiment, the chromophore needles are made of ceramic doped with iron oxide, most preferably iron oxide in the form of magnetite.

The distal end of the chromophore needle is shaped to allow insertion into the tonsil parenchyma with minimal force and minimal tissue trauma. Distal end tip shapes may include points, angles, bevels, and any other penetrating or cutting tip shape used for hypodermic needles and known to the art. Chromophore needles may be either hollow, or solid. In a preferred embodiment, chromophore needles are solid. In another preferred embodiment, a hollow chromophore needle is used and includes a thermocouple or other temperature sensor within its shaft.

In a most preferred embodiment of the present invention, the chromophore coating of the chromophore needle is carbon or a carbon material. Suitable carbons or carbon materials have properties that include high absorption coefficients for visible and near infrared light, and biocompatibility. Numerous carbons and carbon materials have been synthesized for engineering applications, and have a wide range of physical properties. The materials that are preferred for the present application are identified by first considering the properties of natural crystalline carbon allotropes. Graphite, in which carbon atoms are $sp^2$ hybridized, has a very high and nearly constant absorption coefficient of approximately $2 \times 10^5$ cm$^{-1}$ over the wavelength range of 600 nm to at least 2 microns, this is in contrast to the diamond allotrope which consists of $sp^3$ hybridized carbons and which is transparent in the visible and NIR spectral range. The use of pyrolytic carbon as a surface material for prosthetic implants is well known in the art.

Figure 35:
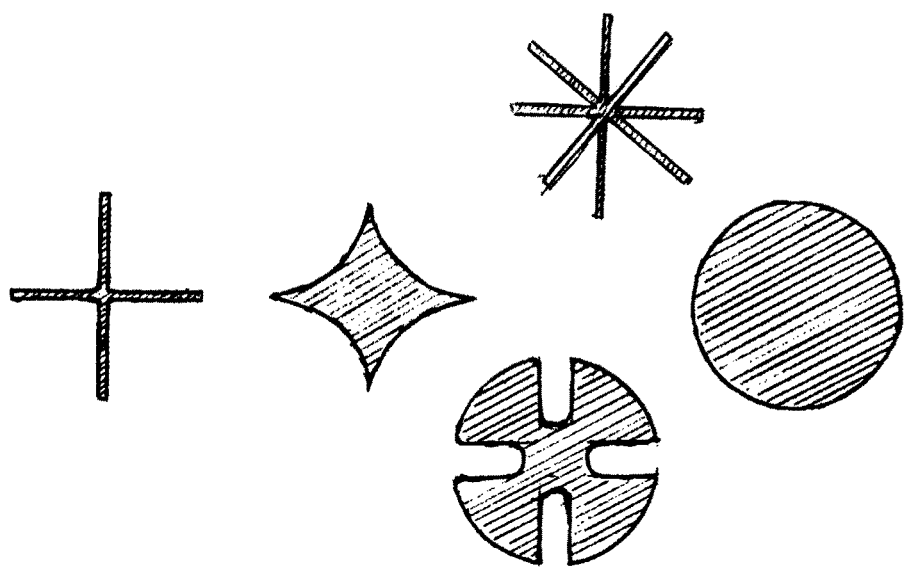
FIG. 35 shows examples of needle cross sectional shapes for increased surface area.

With pyrolytic carbon coating, most of the light reaching the chromophore needle will be absorbed by the first micron thickness of the coating. Consequently, the amount of heat generated by the chromophore needles will be proportional to the surface area of the needles. Therefore, while cylindrical chromophore needles with circular cross sections may be used according to the invention, it may be advantageous to use needles with shapes corresponding to larger relative surface areas. Some of these needle shapes are shown in FIG. 35. For example, a flat blade with sharp distal point and sharp edges may be used. Alternatively, needles with grooves cut in a cylindrical body may be used. A preferred embodiment may use needles that have a cross-shaped or star-shaped cross sectional area, such that there are three to six extending edges along the needle length. It may be noted that such edges may have different lengths relative to the length of a particular needle.

Figure 36:
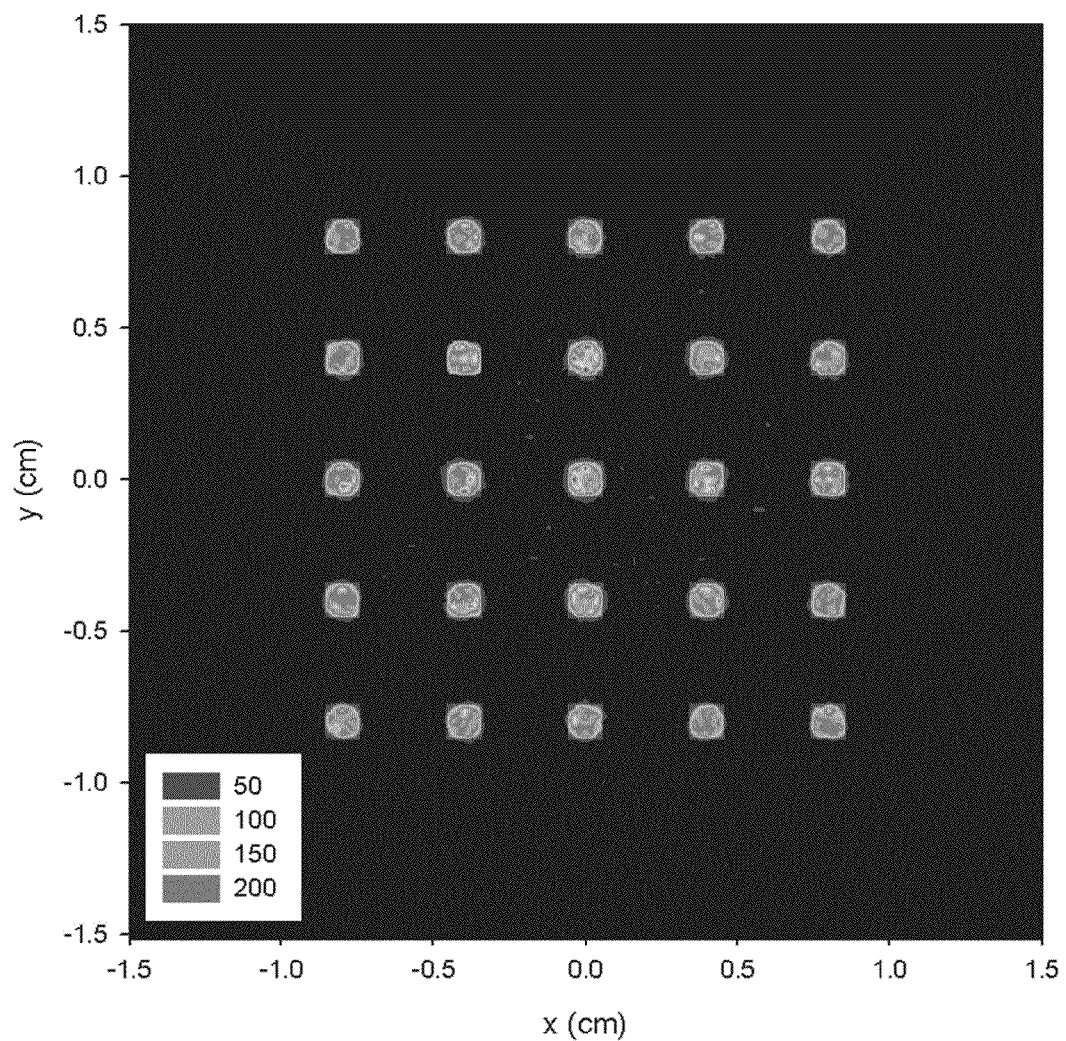
FIG. 36 shows the results of model calculations for tissue treatment with chromophore needles producing a fractional injury.

In another embodiment of the present invention, light may be emitted at relatively high power and short pulse duration, such that heating is substantially localized in the vicinity of the tonsil. FIG. 36 is a contour plot of the results of model calculations for the case of tonsil tissue irradiated with a single 5 ms, 40.6 J pulse of light at 1120 nm, with 25 chromophore needles in an irradiated spot of 28 mm diameter. This embodiment produces a fractional injury to the tissue. In still another embodiment, fractional injury can be combined with substantial injury to the remainder of the tonsil parenchyma by combining short/high power light pulses with lower power/longer light exposures.

Use of exogenous chromophore in the form of needles coated with pyrolytic carbon and fixed in position relative to the light-emitting contact elements enhances absorption of radiation by tonsils with precise localization of a known amount of chromophore, and eliminates the potential safety or toxicity problems associated with injecting dye or chromophore solutions into the tissue. Unlike dyes such as indocyanine green which absorb strongly only within a relatively narrow wavelength range, pyrolytic carbon has a very high absorption coefficient of a very wide range of wavelengths, making it a suitable chromophore for use with lasers operating throughout the visible and near infrared wavelength range so that the operating wavelength can be selected on the basis of optimal tissue penetration depth and extent of absorption by endogenous chromophores such as blood.

The focusing features of the embodiment may also be used to provide enhanced ability to grasp and hold the tonsil.

EXAMPLES OF THE INVENTION

Example 1

In a first example, an apparatus of the invention comprises a 20 W CW quantum dot diode laser operating at 1120-1125 nm coupled to a 275 µm core diameter 0.22 NA silica optical fiber. This laser light source is commercially available as LD-1120-MCP-20W Multichip Laser Diode Module from Innolume GmbH (Dortmund, Germany). The distal end of the optical fiber is attached to a 1×2 fiber optic beamsplitter for 1120-1130 nm with a 50/50 nonpolarizing beamsplitter cube (Oz Optics, Ottawa, ON, Canada). The two output fibers from the beamsplitter are 550/600 µm, 0.22 NA fibers each carrying up to 10 W.

Both output fibers are attached using SMA connectors to optical assemblies attached to a handpiece. Each optical assembly consists of a concave input lens, a hexagonal beamshaper, 19 optical fibers each having diameter of about 0.3 mm and NA of 0.34, a sapphire window with length 18 mm, width 8 mm, and thickness 1 mm, and 3 rectangular mirrors 18 mm long and with height of approximately 2.5 mm. The 19 optical fibers are each 15 to 20 mm long and are combined as a hexagonally shaped bundle without cladding at their proximal ends, to accept light from the hexagonal beamshaper. The three mirrors are placed at evenly spaced locations on the sapphire window, with mirror long axes parallel to each other and to the window long axis. The mirrors are tilted at a 45 degree angle relative to the plane of the window. The distal ends of 6 of the optical fibers are each positioned along a long edge of the sapphire window to be reflected on evenly spaced areas on the first mirror, 7 optical fibers are positioned along the long edge of the window to be reflected on evenly spaced areas on the second mirror, and the remaining 6 fibers are positioned likewise for reflections on the third mirror, to produce an array of 19 irradiated circular spots each 2.5 mm diameter, with overall array shape of approximately 18 mm by 8 mm, on the surface of the sapphire window. The housings containing the optical components have a 45 degree bend between the long axis of the hexagonal beamshaper and the short axis of the sapphire window. The distal surface of the sapphire window is the light-transmitting contact surface of the optical assembly. The thickness of the optical assembly is about 4 to 5 mm. The housing has inlet and outlet connections for coolant flow lines from a recirculating chiller type cooling device (ThermoCube 300, Solid State Cooling Systems, Pleasant Valley N.Y.). The cooling fluid used is Fluorinert™ FC-43 (3M, Minneapolis, Minn.), and is circulated through a channels formed by the elongated mirrors of the optical assemblies to cool the sapphire windows. A sterile flexible transparent sleeve is placed over the distal portions of the handpiece and Ultem grids, each with a 6 mm thermocouple needle probe attached to an approximately central location, are then attached to the contact surfaces by snap fitting over the sterile sleeve, such that the needle probes are perpendicular to the contact surfaces.

A patient requiring treatment for recurrent tonsillitis is treated with the apparatus of the example in an office setting. The subject remains in a seated position, and the oropharynx and tongue is be sprayed with a 20% benzocaine spray for topical anesthesia. Two to 5 ml of 0.5% lidocaine with epinephrine (1:200,000) is injected in the plane between the lateral capsule of the tonsil and the pharyngeal musculature for local anesthesia. The cooling device is activated and the temperature is set to 35° C. The first tonsil is grasped and gently compressed between the contact surfaces of the handpiece with the thermocouple needle probes inserted into the tonsil parenchyma. The laser is activated and the tonsil heated while the thermocouple probe temperature is monitored for the temperature of approximately 65° C. or other appropriate target temperature. At that time, the laser is turned off, and cooling device fluid temperature is reduced to 5° C. Contact cooling is continued with the handpiece until the thermocouple probes indicate that the tonsil has returned to physiologic temperature or is chilled. The opposite tonsil is then treated in the same manner.

Example 2

In a second example, an apparatus of the invention comprises a handpiece with two light-transmitting contact surfaces each of approximately 18 mm length by 8 mm width, and a CW quantum dot diode laser operating at 1120 to 1125 nm, with two output connectors and two 200 μm core diameter, 0.53 NA optical fibers (Ceramoptic WF 200/220 HT 53). In this example the optical assembly is of a diffusing optics design, rather than the reflective optics design of example 1.

Figure 37A:
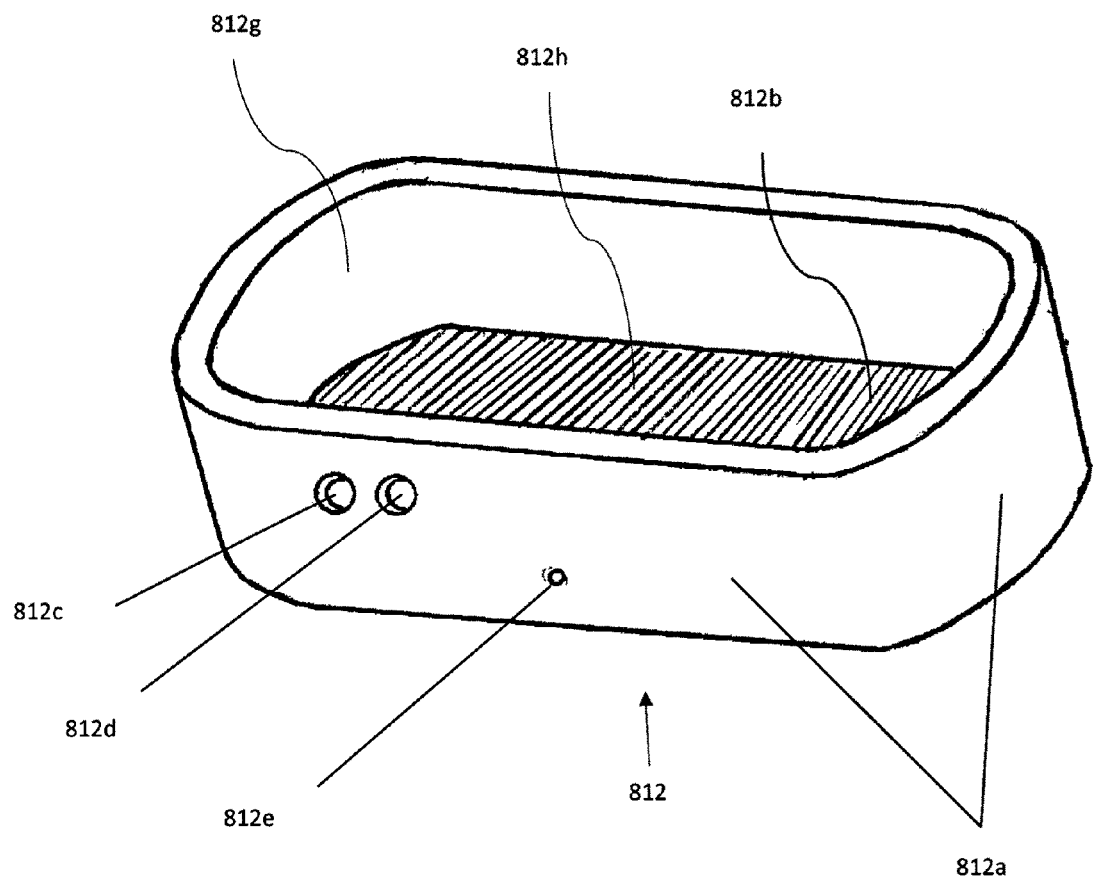
FIG. 37A depicts the housing of an optical assembly of the second example.

FIG. 37A depicts the housing of the device of this example. The housing 812 has lateral walls 812a and base 812b that are approximately 1 mm in thickness. The housing has interior dimensions of 18 mm length and 8 mm width, with a 3 mm radius fillet on the corners, and a height of approximately 5 mm. On the lateral wall of the housing are adjacent openings 812c, 812d for entrance and exit of coolant fluid. These openings are 1 mm in diameter, and are positioned near the end of a flat segment of the lateral wall. Near the center of the same flat segment of the lateral wall is a 0.55 mm diameter opening 812e for entrance of light from the optical fiber of the laser. The base interior surface 812h of the housing is completely coated with Labsphere 6080 barium sulfate paint (Labsphere, North Sutton, N.H.), and the lateral wall interior surface 812g has an optically specular polish with protective gold coating.

Figure 37B:
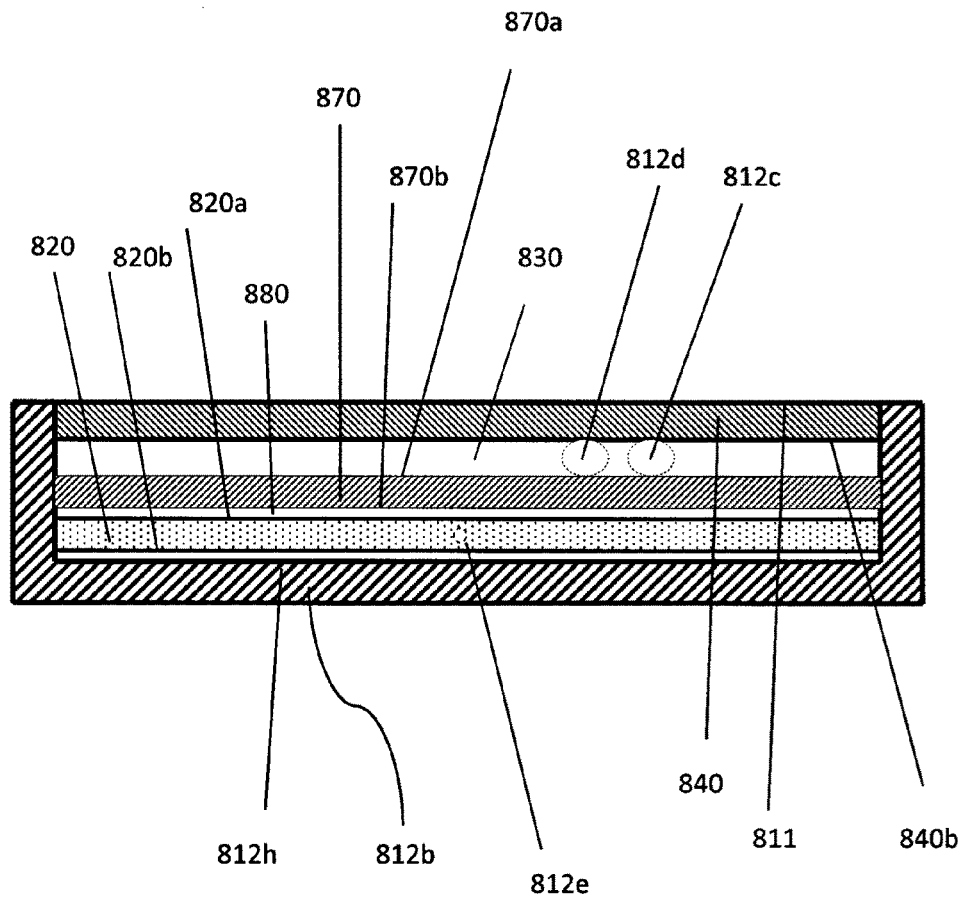
FIG. 37B depicts the elements of the optical stack of an optical assembly of the second example.

FIG. 37B is a cross sectional diagram of the optical stack and housing of the device of this example. The placement of the coolant flow openings 812c, 812d are indicated as projections in this diagram. In near proximity to base interior surface 812h of the back of the housing 812b is the proximal surface 820b of a 1 mm-thick light guide plate 820. The proximal surface 870b of a 1 mm-thick window plate 870 is separated from the distal surface 820a of the light guide plate 820 by an airspace 880 of at least 2 microns thickness. A 1 mm-thick tissue contacting surface optic 840 has a tissue contacting distal surface 811 and a coolant contacting proximal surface 840b. The light guide plate 820 and coolant window plate 870 are made of quartz, and the tissue contacting window 840 is sapphire. The proximal surface 840b of the sapphire window is separated from the distal surface 870a of the coolant window plate by a 1 mm space that serves as a coolant flow layer 830. The quartz light guide plate 820, quartz coolant window 870, and sapphire contact window 840 are plane parallel windows. In the device of this example, the quartz light guide plate 820 and quartz window 870 are identical. The quartz light guide plate, quartz window and sapphire window are held fixed in contact with the housing lateral wall so that they are parallel to each other.

The entrance in the lateral wall for the optical fiber 812e, projected in FIG. 37B, is positioned so that light exiting the fiber is centered on the quartz light guide plate lateral edge. The coolant entrance and exit holes in the housing lateral walls are aligned with the coolant flow chamber 830. When coolant fluid enters the chamber 830 at hole 812c it fills the chamber and flows out at exit hole 812d. In the device of this example, the fluid is perfluorocarbon, for example FC-43 (Fluorinert™, 3M, Minneapolis, Minn.).

Figure 37C:
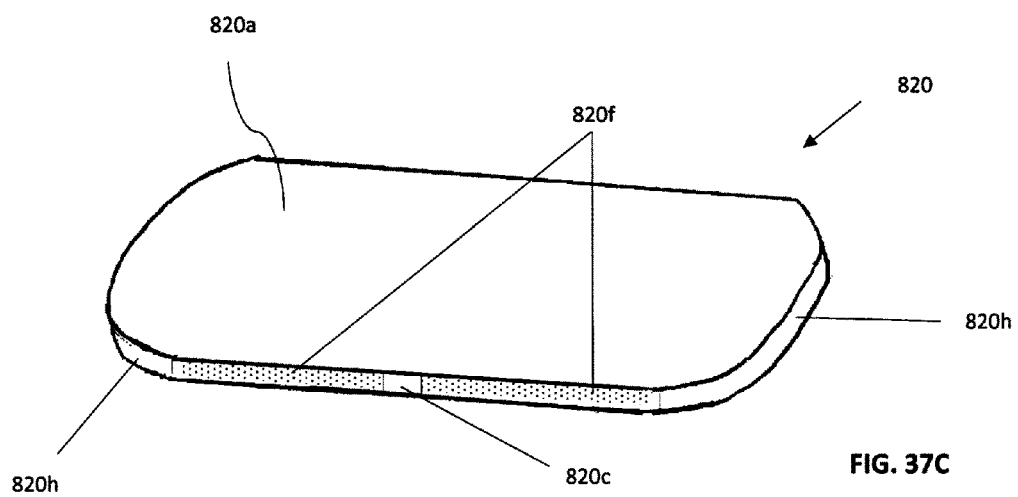
FIGS. 37C and D depict the light guide plate with coatings of the lateral walls.
Figure 37D:
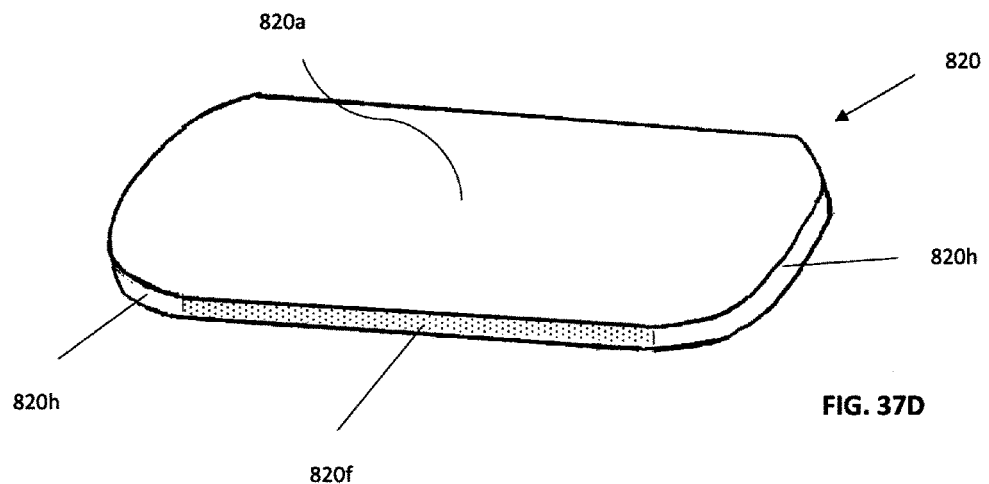
FIG. 37E depicts the extraction features of the light guide plate of an optical assembly of the second example.
FIG. 37F shows the irradiance diagram for an optical assembly of the second example.

The lateral edges of the sapphire contact window and quartz coolant window are optically smooth polished. The lateral walls of the light guide plate 820 have protected gold coating on flat segments 820f parallel to the long axis, with the exception of a small (1 mm by 1 mm) uncoated area 820c where light from the fiber enters the light guide plate (FIG. 37C, rotated view FIG. 37D). The surfaces of the lateral walls at the ends of the light guide plate 820h are coated with Labsphere 6080 paint. The gold coated lateral edges of the light guide plate are optically smooth and the paint coated end edges are unpolished.

Figure 37E:
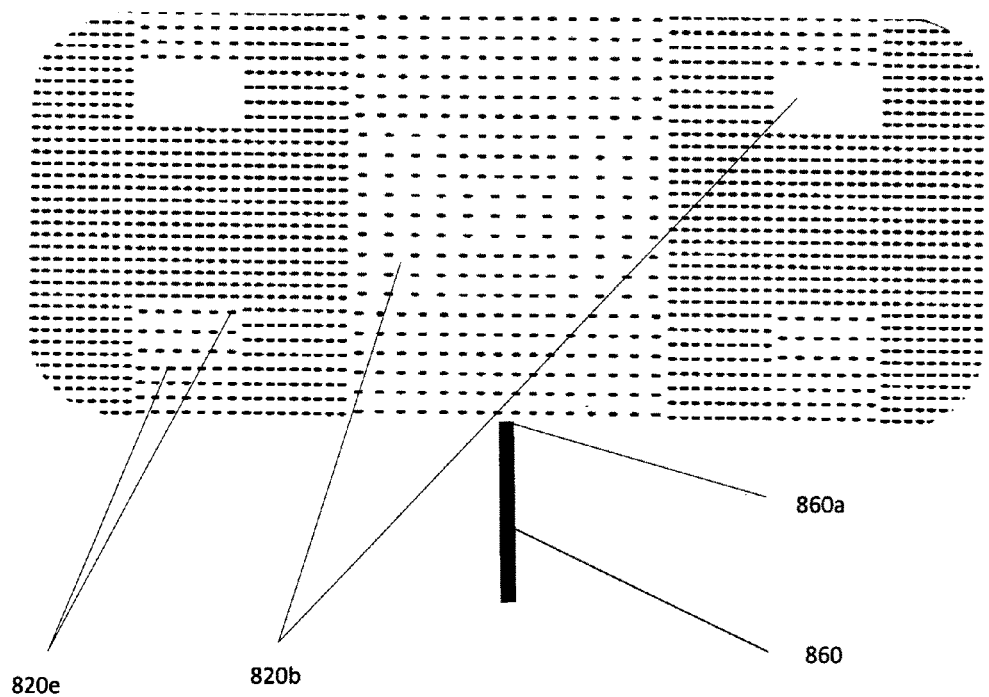

The proximal surface 820b of the light guide plate has extraction features 820e in the form of Labsphere 6080 paint dots (200 micron dot diameter). The pattern of paint dots is schematically indicated in FIG. 37E, with the size of the dots enlarged for visibility. The pattern was selected on the basis of Monte Carlo ray trace calculations (Optical Research Associates, Pasadena, Calif.), for efficiency and uniformity of output.

Figure 37F:
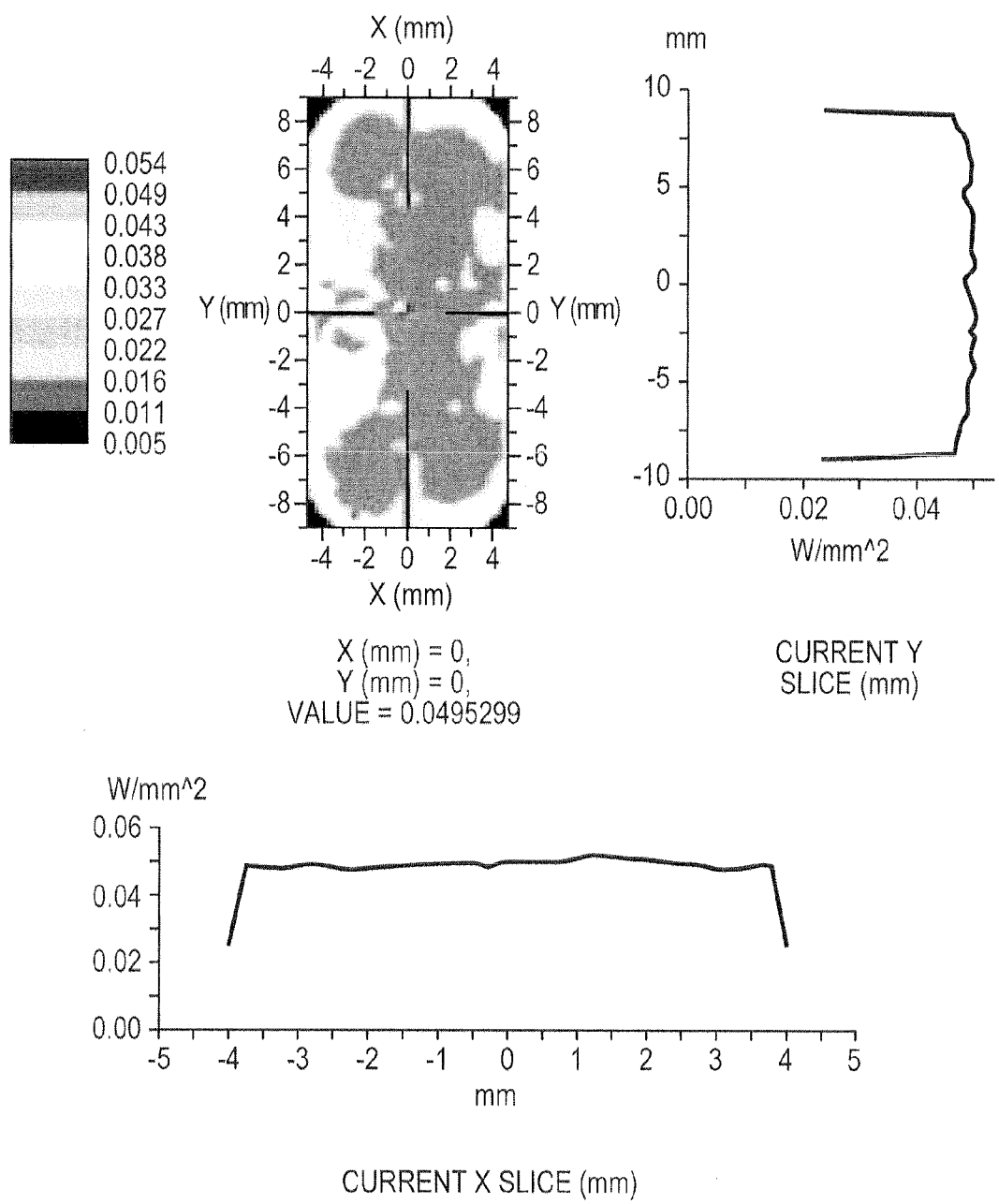

The results of the model calculations for the optical assembly of the apparatus of this example are shown in FIG. 37F. The efficiency of the optical assembly is 67%. With a 10 W input at each optical assembly, the maximum and minimum irradiance is 0.054 and 0.044 W/mm$^2$, respectively. The average irradiance is 40 mW/mm$^2$. Uniformity is +10.5%, −9.5%. The intensity profile is substantially Lambertian.

Example 3

In this example, a apparatus of the invention with light-transmitting surface of circular shape is described. The light-emitting surface has a diameter of 13.5 mm, making that surface area approximately equal to the light-emitting surface of the 18 mm×8 mm device of the previous examples. The laser is an 1120-1125 nm dot laser (Innolume, Dortmund, Germany) coupled to two 200 micron core diameter, 0.53 NA optical fibers (Ceramoptic WF 200/220 HT 53).

Figure 38A:
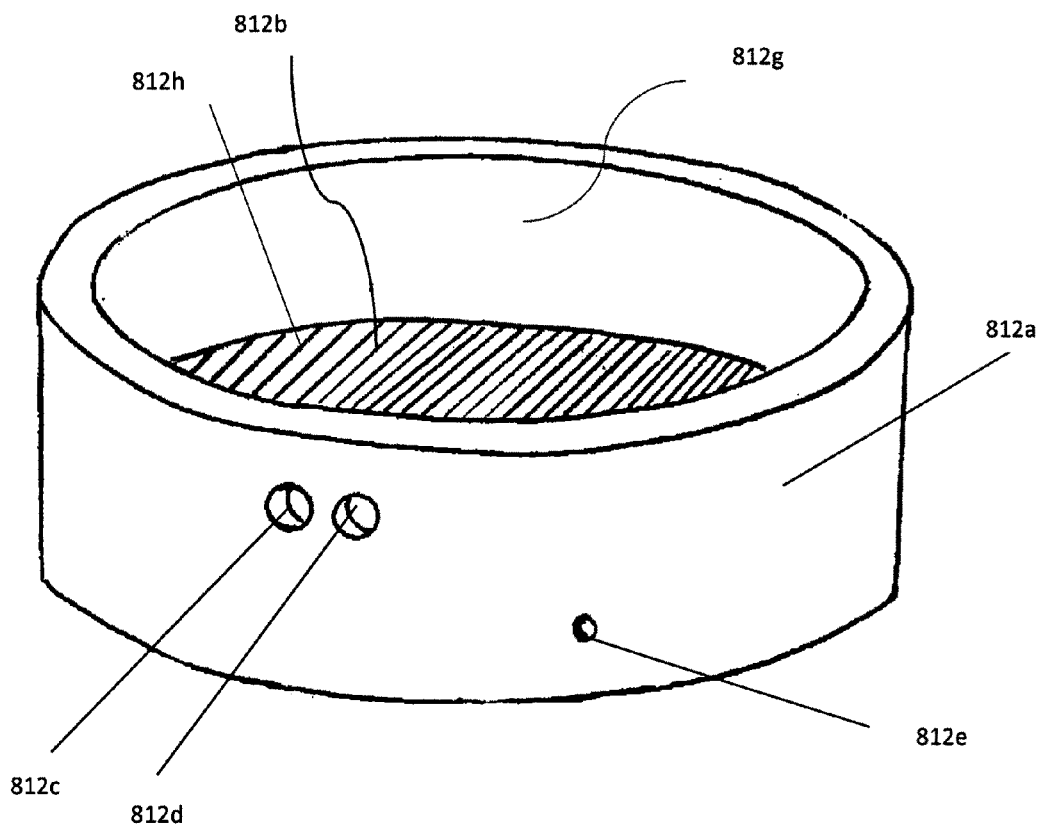
FIG. 38A depicts a housing of an optical assembly of the third example.

FIG. 38A depicts the housing of the device of this example. The housing 812 has lateral walls 812a and base 812b that are approximately 1 mm in thickness. The housing has interior diameter of 13.5 mm, and a height of approximately 5 mm. On the lateral wall of the housing are adjacent openings 812c, 812d for entrance and exit of coolant fluid. These openings are 1 mm in diameter. Also on the lateral wall is a 0.55 mm diameter opening 812e for entrance of light from the optical fiber of the laser. The base interior surface 812h of the housing is completely coated with Labsphere 6080 barium sulfate paint (Labsphere, North Sutton, N.H.), and the lateral wall interior surface 812g has an optically specular polish with protective gold coating.

Figure 38B:
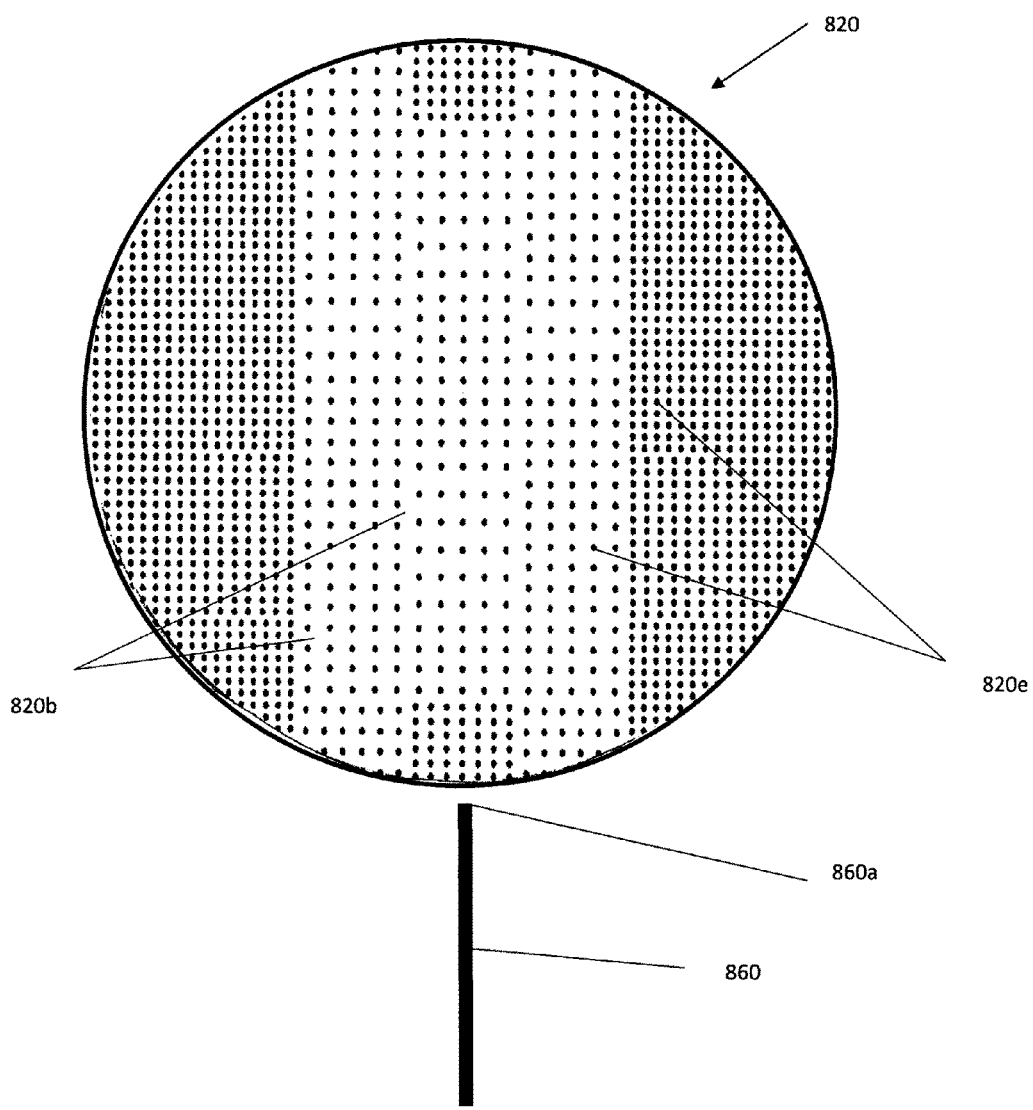
FIG. 38B depicts the light guide plate with extraction features of an optical assembly of the third example.

The optical assembly of the present example is the same as in example 3 with the exception of the shape of the components, and the distribution and arrangement of extraction feature. FIG. 38B is a schematic depiction of the extraction features 820e on the proximal surface 820b of the quartz light guide plate 820. The exit face 860a of the optical fiber 860 is adjacent to the lateral edge of the light guide plate. The extraction features are paint dots applied by screen printing using Labsphere 6080 paint. Each paint dot is 200 microns in diameter and is expanded in size in the for visibility. The arrangement of the paint dots was selected on the basis of Monte Carlo ray tracing (Optical Research Associates, Pasadena, Calif.).

Figure 38C:
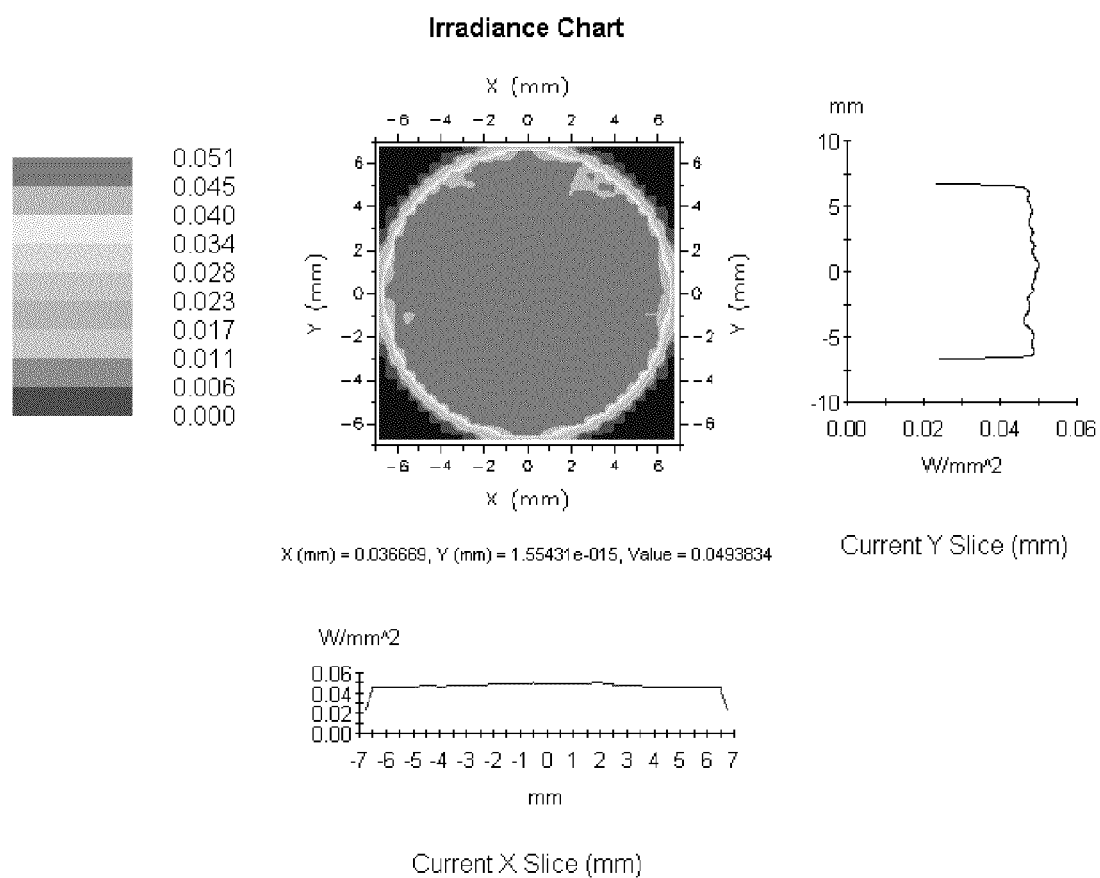
FIG. 38C shows the irradiance diagram of an optical assembly of the third example.

The results of the model calculations for the device of this example are shown in FIG. 38C. The optical characteristics are similar to those of the device of Example 2, which has similar design and approximately the same surface area. The efficiency of the device of this example is 68%. With a 10 W input at each optical assembly, the maximum and minimum irradiance is 0.051 and 0.043 W/mm$^2$, respectively. The average irradiance is 47 mW/mm². Uniformity is +7%, −9%. The intensity profile is substantially Lambertian.

Example 4

Previous examples employed an 1120 nm diode laser. In this example, an optical assembly of the design of Example 2 having 18 mm×8 mm light transmitting contact surface area is used with an 808 nm diode laser from JENOPTIC Laserdiode GmbH (Jena, Germany). The 808 nm laser is coupled to a 200 micron core diameter, 0.53 NA optical fiber (Ceramoptic WF 200/220 HT 53), which is in turn coupled to the optical assembly. As in Example 2, the fluid is perfluorocarbon FC-43 (Fluorinert™, 3M, Minneapolis, Minn.). Thus, the handpiece, including the pattern of paint dot extraction features, is completely unchanged from Example 2 and the only difference is the light source.

Figure 39:
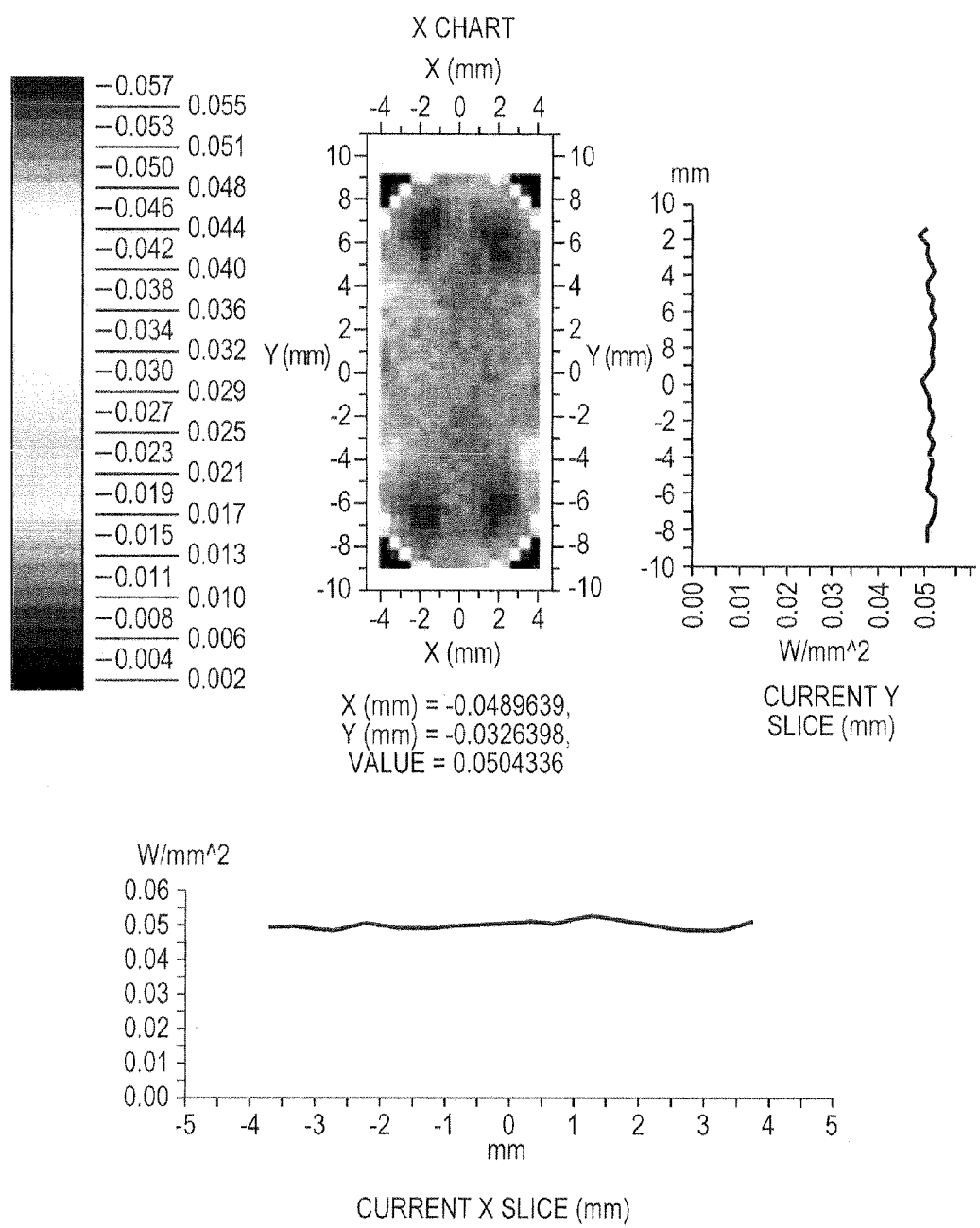
FIG. 39 shows the irradiance diagram for the optical assembly of the fourth example.

Results of the Monte Carlo ray trace calculation of irradiance at the sapphire contact window distal surface is shown in FIG. 39. It is found in the calculation of this example that despite the wavelength change of 300 nm, the irradiance distribution remains highly uniform. This example demonstrates the finding that a device of the invention may be used with different wavelengths without further modification being necessary. Water may also be used as coolant fluid with an apparatus of the present example.

The present invention has been described in detail for the treatment of palatine tonsils, but has many other additional uses in the treatment of soft tissue. For example, the invention may be adapted to treat lingual tonsils at the base of the tongue, or to remove the appendix. Other important additional uses include the phototherapeutic treatment of solid tumors, and blood vessel ligation.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for light treatment of soft tissue, comprising at least two opposed optical assemblies, each coupled by an optical transmission device to a light source, wherein each assembly comprises:
    a) a light-transmitting contact surface adapted to transmit the light to the soft tissue;
    b) a light guide plate having a light input surface at a lateral surface, said light guide plate adapted to receive light from the optical transmission device, the light propagating through the light guide plate;
    c) extraction features formed on a proximal surface of the light guide plate by application of material to the proximal surface of the light guide plate;
    d) a reflecting plate separated from the proximal surface of the light guide plate, said reflecting plate being in direct physical contact with the extraction features on the proximal surface of the light guide plate; and
    e) an extraction space defined by the proximal surface of the light guide plate and the reflecting plate,
    wherein the light guide plate, the extraction features, the reflecting plate, and the extraction space are adapted to transmit light reflected from the extraction features to the soft tissue through the light-transmitting contact surface in a substantially uniform distribution, and are housed in an optical assembly housing, the assembly further comprising:
    f) a cooling layer adjacent to a base interior surface of the optical assembly housing, and adjacent to a lateral interior surface of the optical assembly housing, such that heat is conducted from the light-transmitting contact surface through the extraction features to the cooling layer.

2. The apparatus of claim 1, wherein the substantially uniform distribution of light has a wavelength within the range of about 700 nm to about 1350 nm.

3. The apparatus of claim 2, wherein the substantially uniform distribution of light has a wavelength within the range of about 1100 nm to about 1140 nm.

4. The apparatus of claim 1, further comprising a handpiece to which the at least two opposed optical assemblies are attached, the handpiece being adapted to move the light-transmitting contact surfaces to cooperate together to hold and compress soft tissue therebetween.

5. The apparatus of claim 4, further comprising a disposable element.

6. The apparatus of claim 5, wherein the disposable element comprises a grid element.

7. The apparatus of claim 6, wherein the grid is removably attached to the optical assembly.

8. The apparatus of claim 7, wherein the grid element is removably attached to the optical assembly by a snap fitting or a slide and groove.

9. The apparatus of claim 6, wherein the grid element is coated with a reflective material.

10. The apparatus of claim 6, wherein the grid element comprises a moldable or machinable biocompatible plastic.

11. The apparatus of claim 6, wherein the grid element comprises a laser resistant plastic.

12. The apparatus of claim 6, wherein the grid element is made of polyetherimide resin or polycarbonate resin.

13. The apparatus of claim 6, wherein the grid element comprises channels or holes for temperature sensor lead wires.

14. The apparatus of claim 13, wherein the channels or holes include a reflective surface to shield said wires from light.

15. The apparatus of claim 6, wherein the grid element comprises open areas through which at least one of the light-transmitting contact surfaces is exposed.

16. The apparatus of claim 5, wherein the disposable element comprises a collar attached to at least one distal portion of the handpiece.

17. The apparatus of claim 5, further comprising at least one needle, the needle being affixed to the disposable element at a proximal end of the needle and having distal tip.

18. The apparatus of claim 17, wherein the needle is a chromophore needle.

19. The apparatus of claim 18, chromophore needle is capable of substantially absorbing light.

20. The apparatus of claim 19, wherein the chromophore needles have different lengths.

21. The apparatus of claim 19, wherein chromophore needles comprise temperature sensors.

22. The apparatus of claim 19, wherein chromophore needles are coated with a carbon material.

23. The apparatus of claim 19, wherein chromophore needles are coated with pyrolytic carbon.

24. The apparatus of claim 18, wherein the chromophore needle is capable of reflecting light.

25. The apparatus of claim 24, wherein the chromophore needle is coated with a chromophore that absorbs near infrared light.

26. The apparatus of claim 18, further comprising a plurality of chromophore needle arranged in a pattern.

27. The apparatus of claim 18, wherein the chromophore needle is hollow or solid.

28. The apparatus of claim 18, wherein the chromophore needle has a cross sectional shape to maximize a surface area of the chromophore needles.

29. The apparatus of claim 18, wherein the chromophore needle comprises a material with a substantially high thermal conductivity.

30. The apparatus of claim 17, wherein the needle is a temperature sensor needle comprising at least one temperature sensor.

31. The apparatus of claim 30, further comprising a plurality of temperature needles having various lengths.

32. The apparatus of claim 30, wherein the temperature sensor needle has a u-shaped curved base or angled base at the proximal end.

33. The apparatus of claim 30, wherein exterior and/or interior surfaces of the sensor needle is made of or coated by a material that substantially reflects light.

34. The apparatus of claim 30, wherein the temperature needle sensors have a time constant on the order of about 0.1 second or less.

35. The apparatus of claim 4, wherein the optical assembly comprises at least one reflecting device.

36. The apparatus of claim 35, wherein the at least one reflecting device is a prism or a mirror.

37. The apparatus of claim 36, wherein the optical assembly comprises a plurality of reflecting devices, each reflecting device corresponding to a segment area of light distributed at the light-transmitting contact surface.

38. The apparatus of claim 37, further comprising a cooling device configured to provide cooling fluid to at least one of the optical assemblies, wherein the cooling fluid is brought in direct contact with the plurality of reflecting devices.

39. The apparatus of claim 38, further comprising at least one channel for cooling fluid flow in direct contact with the plurality of reflecting devices.

40. The apparatus of claim 35, further comprising a cooling device configured to provide cooling fluid to the optical assembly to remove heat from the light transmitting contact surface of the at least two opposed optical assemblies.

41. The apparatus of claim 4, wherein the handpiece comprises at least two distal portions, wherein each of the opposed optical assemblies is affixed to one of the distal portions and wherein at least one of the distal portions is movable relative to the other.

42. The apparatus of claim 1, wherein the light is provided from a light source selected from the group consisting of fiber lasers, semiconductor lasers, and neodymium doped yttrium aluminum garnet lasers.

43. The apparatus of claim 1, further comprising a cooling device configured to provide cooling fluid to the optical assembly to remove heat from the light transmitting contact surface of at least one of the at least two opposed optical assemblies.

44. The apparatus of claim 1, wherein the extraction features are arranged in a pattern.

45. The apparatus of claim 1, wherein the extraction features are on one or both sides of the light guide plate.

46. The apparatus of claim 1, further comprising an optical assembly housing enclosing at least a portion of the light guide plate and having an opening at the lateral light input surface of the light guide plate.

47. The apparatus of claim 46, wherein the housing has a thickness sufficiently small such that a substantial portion of a tonsil parenchyma can be disposed between the light-transmitting contact surfaces when the tonsil is retracted in a medial direction and held by the light-transmitting contact surfaces of the handpiece.

48. The apparatus of claim 47, wherein the housing has a thickness sufficiently small such that substantially all of the tonsil parenchyma can be disposed between light-transmitting contact surfaces when the tonsil is retracted in a medial direction and held by said light-transmitting contact surfaces of the handpiece.

49. The apparatus of claim 47, wherein the housing has a thickness less than about 6 mm.

50. The apparatus of claim 46, wherein the surface area of each of the light-transmitting contact surfaces is sufficiently large such that light transmitted from the surfaces irradiates a substantial portion of a tonsil gently compressed between the surfaces.

51. The apparatus of claim 50, wherein each of the light-transmitting surfaces has a surface area of at least about 20 $mm^3$ up to about 1250 $mm^3$.

52. The apparatus of claim 51, wherein each of the light-transmitting surfaces has a surface area between about 100 $mm^3$ and about 1250 $mm^3$.

53. The apparatus of claim 51, wherein each of the light-transmitting surfaces has a geometric or non-geometric shape.

54. The apparatus of claim 51, wherein each of the light-transmitting surfaces has a circular or ovular shape.

55. The apparatus of claim 1, wherein the light-transmitting contact surface comprises a distal surface of the light guide plate and the optical element further comprises an air gap adjacent to the proximal surface of the light guide plate, a base interior surface of the optical assembly housing, and a lateral interior surface of the optical assembly housing.

56. The apparatus of claim 1, wherein the optical assembly further comprises:
an air gap adjacent to the proximal surface of the light guide plate, a base interior surface of an optical assembly housing, and a lateral interior surface of the optical assembly housing;
a cooling layer adjacent to the distal surface of the light guide plate; and
a contact window having a proximal surface adjacent to the cooling layer, wherein the light-transmitting contact surface comprises a distal contact surface of the contact window.

57. The apparatus of claim 1, wherein the optical assembly further comprises:
a first air gap adjacent to the proximal surface of the light guide plate, a base interior surface of an optical assembly housing, and a lateral interior surface of the optical assembly housing; and
a second air gap adjacent to a distal surface of the light guide plate, a proximal surface of a cooling layer window and a lateral interior surface of the optical assembly housing;
a cooling layer adjacent to a distal surface of the cooling layer window; and
a contact window having a proximal surface adjacent to the cooling layer, wherein the light-transmitting contact surface comprises a distal contact surface of the contact window.

58. The apparatus of claim 1, further comprising a cooling layer adjacent to the proximal surface of the light guide plate, a base interior surface of an optical assembly housing, and a lateral interior surface of the optical assembly housing, wherein the light-transmitting contact surface comprises a distal surface of the light guide plate, and wherein the light guide plate has a higher index of refraction than that of a cooling fluid in the cooling layer.

59. The apparatus of claim 1, further comprising
- a cooling layer adjacent to a base interior surface of an optical assembly housing, a lateral interior surface of the optical assembly housing and a reflecting plate; and
- an extraction space between the reflecting plate and the proximal surface of the light guide plate, wherein the light-transmitting contact surface comprises a distal surface of the light guide plate.

60. The apparatus of claim 59, wherein the extraction space comprises a heat transfer fluid having a refractive index lower than the light guide plate.

61. The apparatus of claim 1, wherein the reflecting plate comprises a diffusive reflective coating on the surface of the reflecting plate in contact with the extraction features.

62. The apparatus of claim 1, wherein the light-transmitting contact surface comprises focusing features.

\* \* \* \* \*

UNITED STATES PATENT AND TRADEMARK OFFICE
CERTIFICATE OF CORRECTION

PATENT NO. : 8,685,010 B2  Page 1 of 1
APPLICATION NO. : 12/625335
DATED : April 1, 2014
INVENTOR(S) : Kathleen McMillan et al.

It is certified that error appears in the above-identified patent and that said Letters Patent is hereby corrected as shown below:

In the Claims:

In Column 58, Claim 51, lines 24-25, delete "20 mm$^3$" and insert --20 mm$^2$--.
In Column 58, Claim 51, line 25, delete "1250 mm$^3$" and insert --1250 mm$^2$--.
In Column 58, Claim 52, lines 27-28, delete "100 mm$^3$" and insert --100 mm$^2$--.
In Column 58, Claim 52, line 28, delete "1250 mm$^3$" and insert --1250 mm$^2$--.

Signed and Sealed this
Eighth Day of July, 2014

Michelle K. Lee
*Deputy Director of the United States Patent and Trademark Office*